(12) United States Patent
Seltzer et al.

(10) Patent No.: US 6,447,644 B1
(45) Date of Patent: Sep. 10, 2002

(54) INHIBITION OF PULP AND PAPER YELLOWING USING NITROXIDES, HYDROXYLAMINES AND OTHER COADDITIVES

(75) Inventors: Raymond R. Seltzer, New City, NY (US); Jean-Pierre Wolf, Courtaman (CH); Cyril Heitner, Pierrefonds (CA); John A. Schmidt, L'ile Bizard (CA); Peter F. McGarry, L'ile Bizard (CA); Glen T. Cunkle, Stamford, CT (US); Randall B. Nelson, Seattle, WA (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/974,382

(22) Filed: Oct. 10, 2001

Related U.S. Application Data

(62) Division of application No. 09/573,401, filed on May 18, 2000, which is a division of application No. 09/119,567, filed on Jul. 20, 1998, now Pat. No. 6,254,724.
(60) Provisional application No. 60/054,968, filed on Aug. 7, 1997, and provisional application No. 60/053,489, filed on Jul. 23, 1997.

(51) Int. Cl.$^7$ .......................... D21F 11/00; D21H 23/00
(52) U.S. Cl. .......................... 162/158; 162/70; 162/71; 162/76; 162/77; 162/81; 162/160; 162/162; 162/164.6; 162/164.7; 162/165; 162/166; 162/167
(58) Field of Search .......................... 162/158, 70, 71, 162/76, 77, 81, 160, 162, 164.6, 164.7, 165, 166, 167

(56) References Cited

U.S. PATENT DOCUMENTS

| | | | |
|---|---|---|---|
| 3,832,277 A | 8/1974 | Smith et al. | 162/70 |
| 5,360,515 A | 11/1994 | Francis et al. | 162/135 |
| 5,443,634 A | 8/1995 | Francis et al. | 106/465 |
| 5,529,896 A | 6/1996 | Hioki et al. | 430/572 |
| 5,538,840 A | 7/1996 | Van Toan et al. | 430/52 |
| 5,658,431 A | 8/1997 | Janson et al. | 162/135 |

FOREIGN PATENT DOCUMENTS

| | | |
|---|---|---|
| CA | 0717143 | 6/1996 |
| CA | 2164394 | 6/1996 |
| EP | 0309401 | 3/1989 |
| EP | 0389429 | 9/1990 |
| FR | 2636358 | 3/1990 |
| JP | 361004045 | 1/1986 |
| WO | 96/29311 | 9/1996 |
| WO | 97/36041 | 3/1997 |

OTHER PUBLICATIONS

Polymer Science USSR, vol. 29, No. 3, pp. 688–694, (1987).
Sykr et al, Journal of the Association of Paper and Pulp Technology: 29, pp. 135–140, (3/90), Studies on Brightness Reversion of Pulps (V) ,On the brightness stabilization of bleached kraft pulp with metallic salts and organic acids.
De Violet et al, Cellulose Chem. Technol., 24, pp. 225–235, (1990).
$6^{th}$ International Sumposium on Wood and Pulping Chemistry, vol. 1, (1991); AGNEMD pp. 631–637.
Journal of the Association of Paper and Pulp Technology: 48, pp. 1388–1394, (11/93), Manuscript received on Apr. 20, 1993 The Effect of Chemical Additives on the Light Reversion of Mechanical Pulp, Omari et al.
The $8^{th}$ International Symposium on Wood and Pulping Chemistry, Jun. 6–9, 1995, vol. III, Photostabilization of Paper made from High–Yield Pulps by Acetylation.
Z.–H. Wu et al, Mechanochemistry of Lignin. XVIII, A Novel Approach to Improve Brightness Stability of $H_2O_2$–Bleached High–Yield Pulps by Addition of Radical Scavengers to the Pulping Process, pp. 400–404.
C. Dence et al, Pulp Bleaching, Section III: The Chemistry of Bleaching and Brightness Reversion, Chapter 5: Chemistry of Brightness Reversion and Its Control, pp. 185–212.
Chem. Abstr. 119:238039v (1993).
Heitner et al., ACS Symposium Series 531, "Photochemistry of Lignocellulosic Materials", pp. 1–25, (1993).

*Primary Examiner*—Steven P. Griffin
*Assistant Examiner*—Mark Halpern
(74) *Attorney, Agent, or Firm*—Tyler A. Stevenson; Luther A. R. Hall

(57) ABSTRACT

Pulps or papers, especially chemimechanical or thermomechanical pulps or papers, which still contain lignin, have enhanced resistance to yellowing when they contain an effective stabilizing amount of a hindered amine compound which preferably is a nitroxide, a hydroxylamine or an ammonium salt thereof. This performance is often further enhanced by the presence of one or more coadditives selected from the group consisting of the UV absorbers, the polymeric inhibitors, the nitrones, the fluorescent whitening agents, metal chelating agents, sulfur containing stabilizers, metal salts and diene compounds. Combinations of nitroxides, hydroxylamines or their salts, benzotriazole or benzophenone UV absorbers and a metal chelating agent are particularly effective. Selected derivatives of 1-oxyl-2,2,6, 6-tetramethylpiperidin-4-ol and selected hydroxylamine salts are novel compounds and are surprisingly effective for this purpose.

34 Claims, No Drawings

INHIBITION OF PULP AND PAPER YELLOWING USING NITROXIDES, HYDROXYLAMINES AND OTHER COADDITIVES

This application is a divisional of application Ser. No. 09/573,401, filed May 18, 2000, which is a divisional of application Ser. No. 09/119,567, filed Jul. 20, 1998, now U.S. Pat. No. 6,254,724, issued Jul. 3, 2001, which claims the benefit under 35 USC 119(e) of U.S. provisional application Nos. 60/053,489 and 60/054,968, filed on Jul. 23, 1997 and on Aug. 7, 1997 respectively.

The instant invention pertains to a method for preventing the loss of brightness and for enhancing resistance to yellowing in pulp or paper which still contains lignin by the addition of nitroxides, hydroxylamines or their salts and other coadditives. The instant invention also pertains to novel compounds which are selected derivatives of 1-oxyl-2,2,6,6-tetramethylpiperidin-4-ol or which are their hydroxylamine salts.

BACKGROUND OF THE INVENTION

High-yield and ultra-high yield wood pulps undergo rapid light-induced discoloration, particularly when they are exposed to near ultraviolet light (wave lengths 300–400 nm) in indoor fluorescent light and daylight. This characteristic restricts their use to short-life, low-value paper products. High-yield and ultra-high yield wood pulps can be bleached to a high level of whiteness. If this whiteness could be stabilized against discoloration, these bleached high-yield pulps could displace significant amounts of more expensive fully-bleached, low-yield chemical pulps.

This discoloration is ascribed to the substantial lignin content of high-yield pulps totaling about 20–45% by mass. Phenoxy radicals are the key intermediates in the reaction mechanism. Several light-induced reactions have been proposed to account for their formation such as abstraction of a hydrogen atom from phenolic groups, cleavage of the aryl ether bond of phenacyl aryl ether groups, or breakdown of ketyl radicals formed from saturated aryl-glycerol β-aryl ether structures in lignin. The phenoxy radicals are oxidized by other oxygen-centered radicals (alkoxy, peroxy, hydroxy and perhydroxy) to form yellow chromophores. (C. Heitner in "Photochemistry of Lignocellulosic Materials", C. Heitner, J. C. Scaiano, eds,: ACS Sym. Ser. 531, 1–25 (1993).)

I. E. Arakin et al., Khymiya drevesiny (Chemistry of Wood), 1982, No.2,114 and A. D. Sergeev et al., ibid, 1984, No. 5, 20 disclosed that the use of iminoxyl radicals such as TEMPO (1-oxyl-2,2,6,6-tetramethylpiperidine) is useful in the delignification of wood using the one-stage oxygen-soda (alkaline) process, but made no mention or suggestion of any activity provided by TEMPO on preventing light-induced discoloration of paper or pulp made from such treated wood.

EP 717,143 and WO 97/36041 describe a multicomponent system for changing, reducing or bleaching lignin and lignin-containing materials which comprise a oxidation catalyst, and a N-hydroxyl mediator compound such as a N-hydroxyphthalimide or a dialkylhydroxylamine. These references are aimed at the delignification of wood. There is no mention or suggestion of any activity provided by the N-hydroxyl compounds in preventing the light-induced discoloration of paper or pulp made from such treated wood.

V. I. Khodyrev et al., Vysokomol soyed, A29, No. 3, 616 (1987) [Polymer Sci. U.S.S.R., 29, No. 3, 688 (1987)] show that the photoinitiated oxidation by oxygen causes weathering of cellulosic textile materials such as flax or cotton. The UV absorbers offer no protection, and are actually detrimental. The authors noted that the stable nitroxyl radical 1-oxyl-2,2,6,6-tetra-methyl-4-hydroxypiperidine interacts with alkyl radicals in the cellulose to afford its salubrious stabilizing activity. There is no suggestion by the authors that this stabilizing activity could be applied successfully in lignin-containing pulp and/or paper made therefrom.

M-K. Syker et al., J. Assn. Paper Pulp Tech, 29, 135 (1990) show that selected metal salts such as magnesium sulfate and lower alkanoic acids inhibit color reversion in bleached pulp.

P. Fornier de Violet et al., Cellulose Chem. Tech., 24, 225 (1990) show that the use of UV absorbers and hydrogen donor agents such as thiols, ascorbic acid, etc. help prevent the photoinduced discoloration of hydrogen peroxide bleached wood pulp, but that chain breakers such as hindered phenols and hindered amines (having >N—H or >N—$CH_2$— moieties) had no or even a detrimental effect on preventing photoinduced discoloration.

R. Agnemo et al., Holzforschung (1991), 45 (Suppl), 101, confirmed that free hydroxyl radicals plus lignin lead to undesirable photoyellowing in pulp and paper.

S. Omori et al., J. Assn. Paper Pulp Tech, 48, 1388 (1993) describes the effect of antioxidants and UV absorbers on light reversion and concludes that the combination of an antioxidant and UV absorber prevents color reversion and has a synergistic effect in that activity.

M. Paulsson et al., Nordic Pulp Pap. Res. J., (1995), 10 (1), 62–67, show that efficient photostabilization of unbleached paper or hydrogen peroxide bleached TMP pulp can be achieved by acetylation.

There have been a number of different approaches proposed to inhibiting the yellowing of mechanical pulps. These include: radical scavengers and antioxidants; UV screens; elimination of chromophores after their formation; chemical modification of lignin by alkylation or acetylation; polymeric inhibitors; and two types of coadditives used in combination. Z-H. Wu et al., Holzforschung, 48, (1994), 400 discuss the use of radical scavengers like phenyl-N-tert-butylnitrone to reduce the formation of chromophores during mechanical pulping and give a more light-stable pulp.

C. Heitner, "Chemistry of Brightness Reversion and It Control, Chapter 5", in Pulp Bleaching-Principles and Practice, C. W. Dence, D. W. Reeve, eds., TAPPI Press, Atlanta, 1996, pp 183–211, summarizes the state of the art in the thermal and light-induced yellowing of lignin-containing pulps such as thermomechanical (TMP) and chemithermomechical (CTMP) pulps, showing the seriousness of these undesirable effects discusses generally the then current prior art methods used to attack this problem. These include bleaching, the use of phosphites, UV absorbers, polyalkylene glycols and free radical scavengers such as ascorbic acid, thiols, thioethers, dienes and aliphatic aldehydes and chelating agents such as ethylene-diaminetetraacetic acid (EDTA). The author concluded that, although much progress had been made, much still remains to be done before a successful and practical solution to this loss of brightness and undesirable yellowing of lignin-containing pulp and/or paper is found.

The instant invention described in detail below provides such a solution where the use of selected hindered amine nitroxides, hindered amine hydroxylamines or their salts in combination with selected UV absorbers and metal chelating agents is seen to prevent loss of brightness and to enhance resistance to yellowing in pulp or paper still containing lignin.

DETAILED DESCRIPTION OF THE INVENTION

The addition of hydroxylamines or nitroxide free radicals to high-yield pulp paper either alone or in combinations with UV absorbers, metal chelating agents, fluorescent whitening agents and/or stabilizing polymers effectively achieves light and thermal stability which is similar to that found in papers made from kraft pulps.

Hydroxylamines and nitroxides are known to be efficient free radical traps and may limit the production of o-quinones; UV absorbers limit photochemistry in the underlying substrate to which they are applied, and ultimately reduce the production of free radicals. UV absorbers and nitroxides are each effective at stemming some of the free radical chemistry leading to paper yellowing when used singly. However, when they are used together, hydroxylamines or nitroxides and UV absorbers can effectively stop photochemical yellowing of lignin containing papers which are exposed 24 hours a day under ambient fluorecent lighting conditions for at least 200 days. Both of these types of stabilizers show enhanced inhibiting activity when combined with a metal chelating agent such diethylenetriaminepentaacetic acid, or polymeric inhibitors such as polyethylene glycol.

More particularly the instant invention pertains to a composition having reduced loss of brightness and enhanced resistance to yellowing which comprises (a) a pulp or paper which still contains lignin, and
(b) an effective stabilizing amount of a hindered amine compound of formula I or II

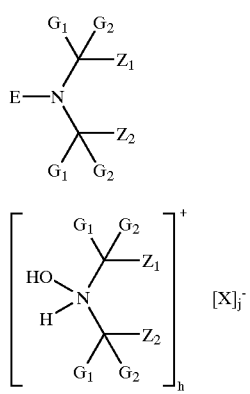

where
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group,
E is oxyl, hydroxyl, hydrogen, alkyl, alkyl substituted by hydroxyl, oxo or carboxy or interrupted by oxygen or carboxy; alkenyl, alkynyl, cycloalkyl, cycloalkenyl, bicycloalkyl, alkoxy, alkoxy substituted by hydroxyl, oxo or carboxy or interrupted by oxygen or carboxy, cycloalkoxy, alkenyloxy, cycloalkenyloxy, aralkyl, aralkoxy, acyl, R(C=O)O—, RO(C=O)O—, RN(C=O)O— or chloro, where R is an aliphatic or aromatic moiety,
X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j, and with the proviso that the compound of formula I is not bis(2,2,6,6-tetramethylpiperidin-4-yl) sebacate or the polycondensation product of 1-(2-hydroxyethyl)-2,2,6,6-tetramethyl-4-hydroxypiperidine and succinic acid.

Preferably, the compositions are those where in the compound of component (b), E is oxyl, hydroxyl, alkenyloxy, aralkoxy, alkyloxy or alkyl substituted by oxo or interrupted by carboxy, especially wherein E is oxyl or hydroxy; most especially wherein E is hydroxy.

Most preferably, X is chloride, bisulfite, bisulfate, sulfate, phosphate, nitrate, ascorbate, acetate, citrate or carboxylate of ethylenediaminetetraacetic acid or of diethylenetriaminepentaacetic acid; most especially wherein X is bisulfate or citrate.

Preferably, the hindered amine compounds of component (b) are those of formulas A to EE and A* to EE*

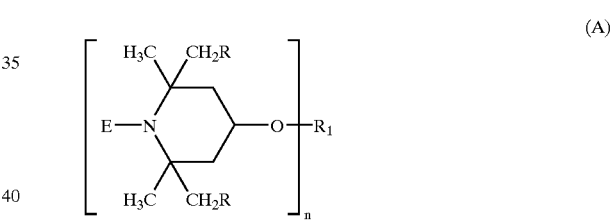

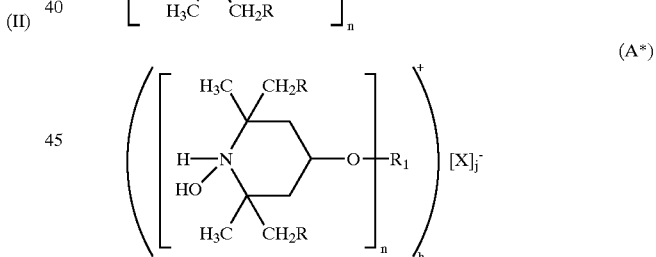

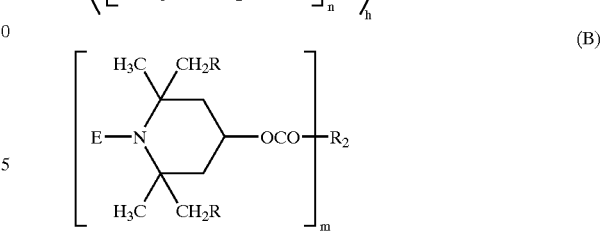

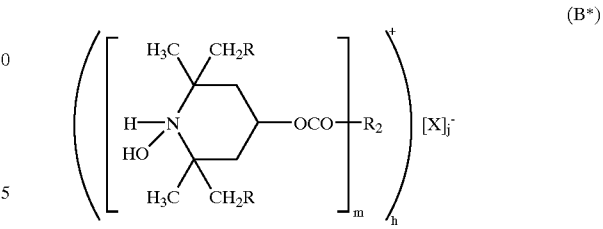

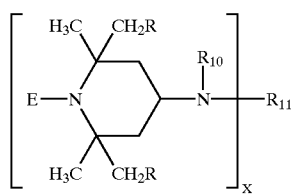
(C)
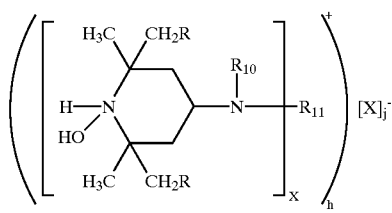
(C*)
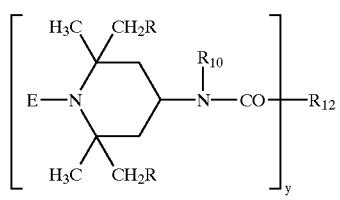
(D)
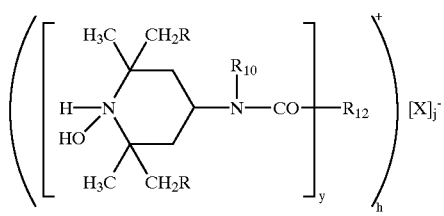
(D*)
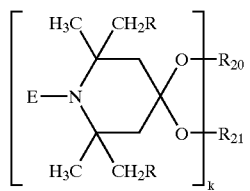
(E)
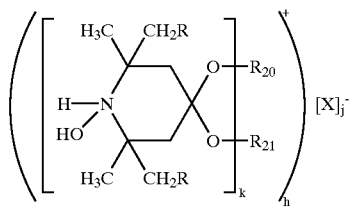
(E*)
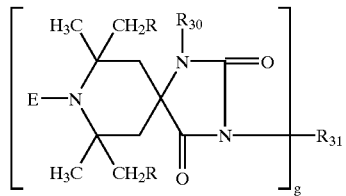
(F)
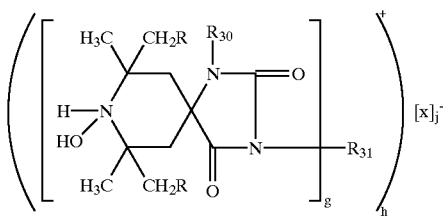
(F*)
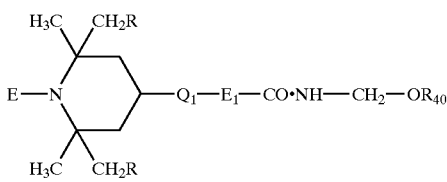
(G)
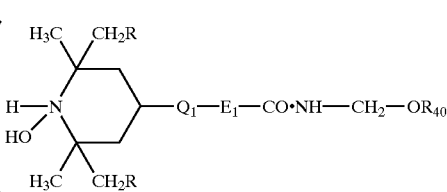
(G*)
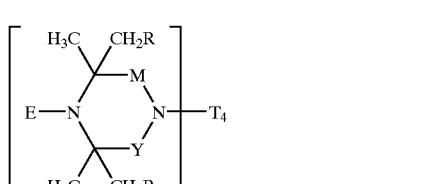
(H)
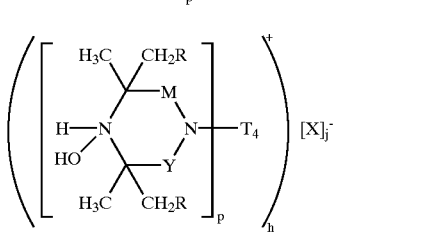
(H*)
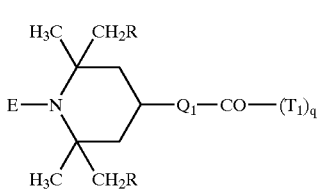
(I)
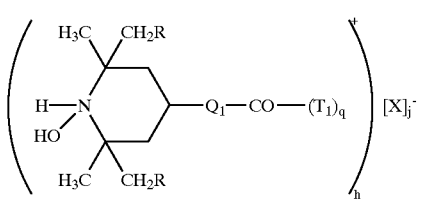
(I*)
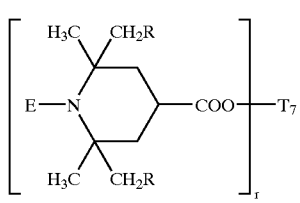
(J)

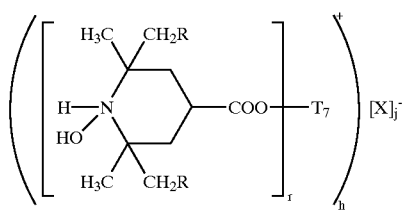
(J*)
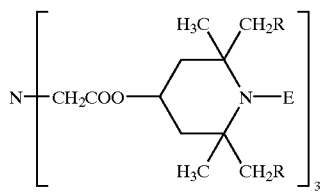
(K)
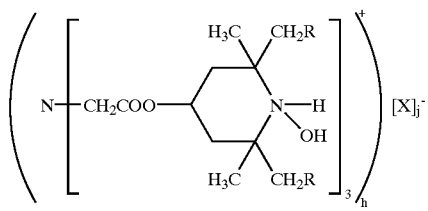
(K*)
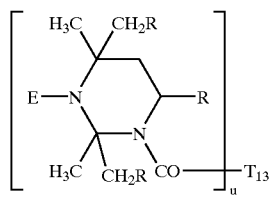
(L)
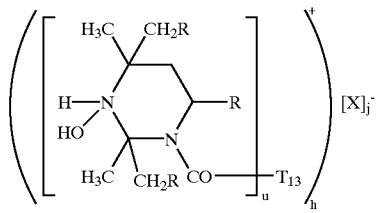
(L*)
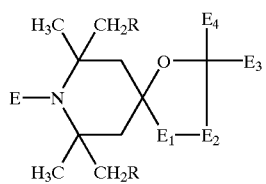
(M)
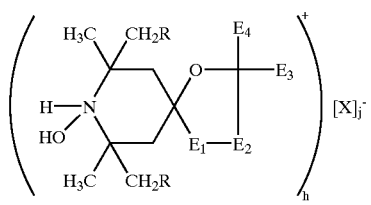
(M*)
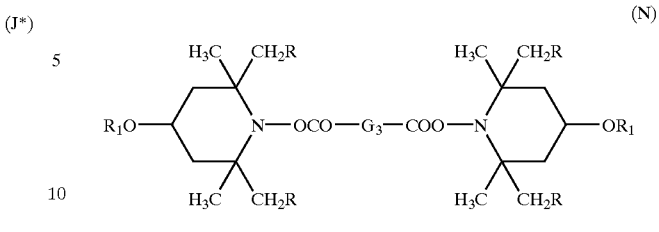
(N)
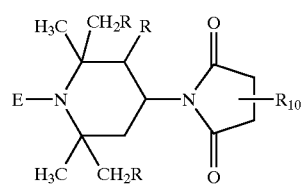
(O)
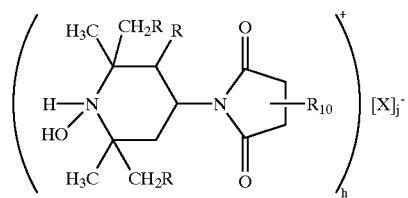
(O*)
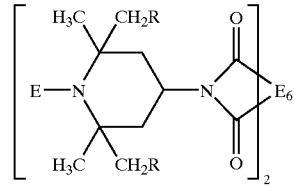
(P)
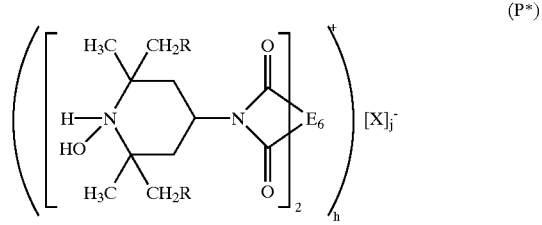
(P*)
(Q)
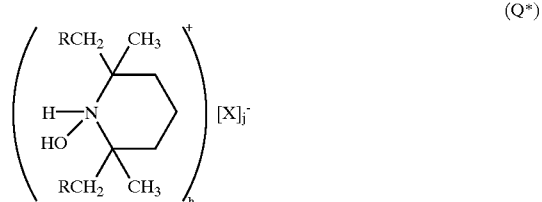
(Q*)
(R)

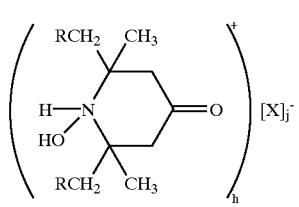 (R*)
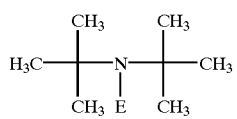 (S)
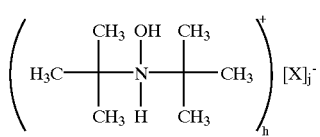 (S*)
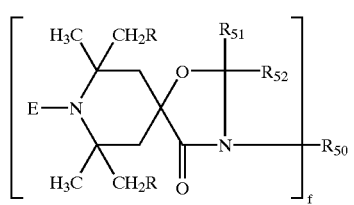 (T)
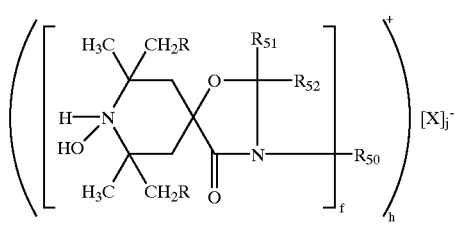 (T*)
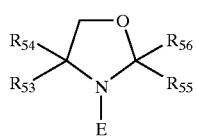 (U)
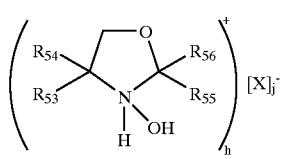 (U*)
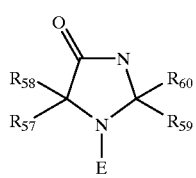 (V)
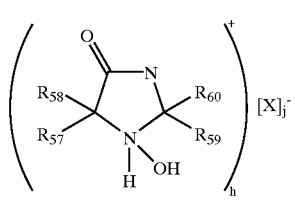 (V*)
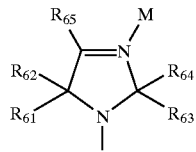 (W)
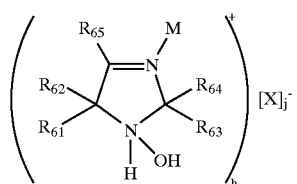 (W*)
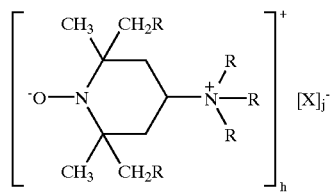 (X)
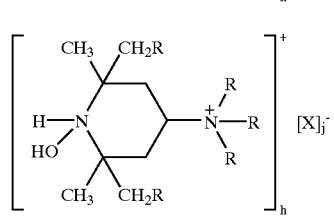 (X*)
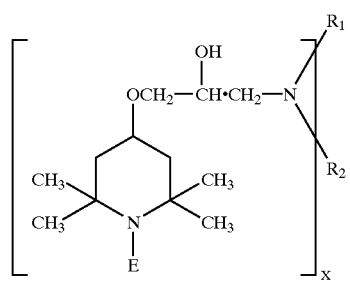 (Y)
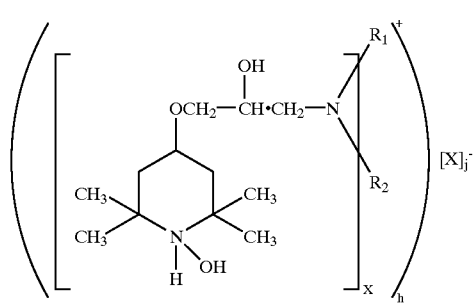 (Y*)
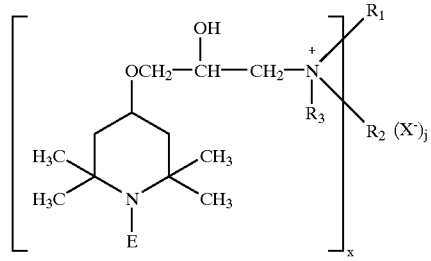 (Z)

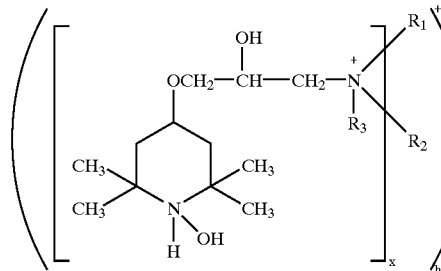 (Z*)

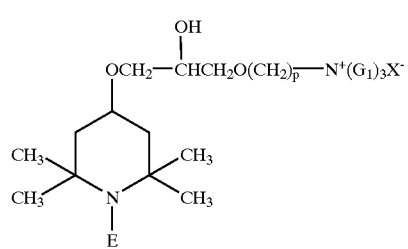 (AA)

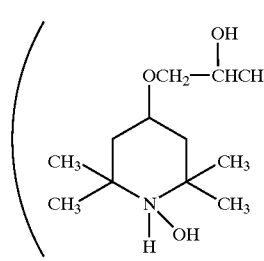 (AA*)

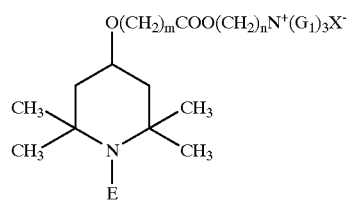 (BB)

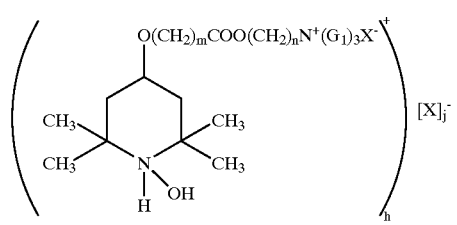 (BB*)

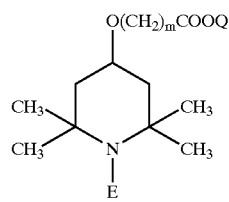 (CC)

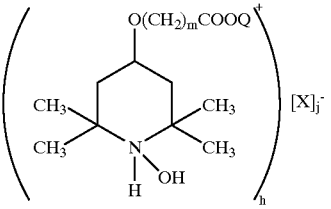 (CC*)

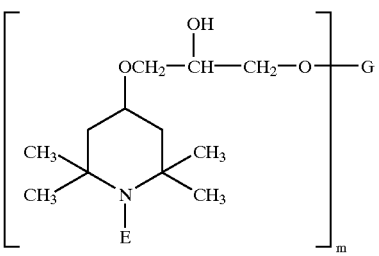 (DD)

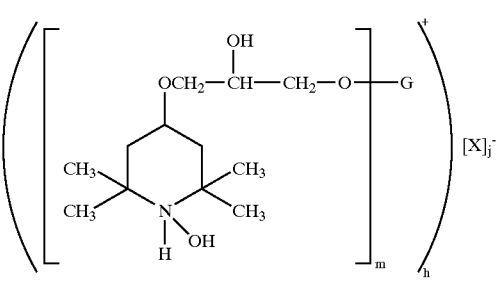 (DD*)

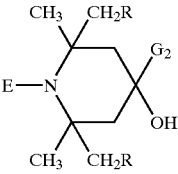 (EE)

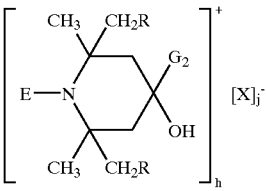 (EE*)

wherein

E is oxyl, hydroxyl, hydrogen, alkyl of 1 to 18 carbon atoms, alkyl of 2 to 12 carbon atoms substituted by one to three hydroxyl or said alkyl interrupted by one to four oxygen atoms, or said alkyl both substituted by said hydroxyl groups and interrupted by said oxygen atoms, alkenyl of 2 to 18 carbon atoms, alkynyl of 2 to 12 carbon atoms, cycloalkyl of 5 to 12 carbon atoms, cycloalkenyl of 5 to 12 carbon atoms, bicycloalkyl of 6 to 10 carbon atoms, alkoxy of 1 to 18 carbon atoms, alkoxy of 2 to 12 carbon atoms substituted by one to three hydroxyl groups or said alkoxy interrupted by one to four oxygen atoms or said alkoxy substituted by —COOZ where Z is hydrogen or alkyl of 1 to 4 carbon atoms, cycloalkoxy of 5 to 12 carbon atoms, cycloalkenyloxy of 5 to 12 carbon atoms, alkenyloxy of 2 to 18 carbon atoms, aralkyl of 7 to 15 carbon atoms, aralkoxy of 7 to 15 carbon atoms, alkanoyl of 2 to 12 carbon atoms, alkenoyl of 2 to 12 carbon atoms, benzoyl, or R(C=O)O—, RO(C=O)O—, RN(C=O)O—, where R is alkyl of 1 to 6 carbon atoms or phenyl, R is hydrogen or methyl, in formula A and A*, n is 1 or 2, when n is 1, $R_1$ is hydrogen, alkyl of 1 to 18 carbon atoms, alkenyl of 2–18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1–3 and M is a metal ion from the 1st, 2nd or 3rd group of the periodic table or is Zn, Cu, Ni or Co, or M is a group N$^{n+}$(R$_2$)$_4$ where $R_2$ is alkyl of 1 to 8 carbon atoms or benzyl, when n is 2, $R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula B and B*, m is 1 to 4, when m is 1, $R_2$ is alkyl of 1 to 18 carbon atoms, alkyl of 3 to 18 carbon atoms interrupted by —COO—, or $R_2$ is —CH$_2$(OCH$_2$CH$_2$)$_n$OCH$_3$ where n is 1 to 12, or $R_2$ is cycloalkyl of 5 to 12 carbon atoms, aryl of 6 to 12 carbon atoms, or said aryl substituted by one to four alkyl groups of 1 to 4 carbon atoms, or $R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —N(R$_3$)$_2$ where $R_3$ is as defined above, when m is 2, $R_2$ is alkylene of 1 to 12 carbon atoms, alkenylene of 4 to 12 carbon atoms, xylylene, alkylene of 2 to 12 carbon atoms interrupted by —COO—, or $R_2$ is —CH$_2$(OCH$_2$CH$_2$)$_n$OCH$_2$— where n is 1 to 2, or $R_2$ is cycloalkylene of 5 to 12 carbon atoms, aralkylene of 7 to 15 carbon atoms or arylene of 6 to 12 carbon atoms, or $R_2$ is —NHR$_4$NH— where $R_4$ is alkylene of 2 to 18 carbon atoms, cycloalkylene of 5 to 12 carbon atoms, aralkylene of 8 to 15 carbon atoms or arylene of 6 to 12 carbon atoms, or $R_2$ is —N(R$_3$)R$_4$N(R$_3$)— where $R_3$ and $R_4$ are as defined above, or $R_2$ is —CO— or —NH—CO—NH—, when m is 3, $R_2$ is alkanetriyl of 3 to 8 carbon atoms or benzenetriyl, or when m is 4, $R_2$ is alkanetetrayl of 5 to 8 carbon atoms or benzenetetrayl, in formula C and C*, $R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, x is 1 or 2, when x is 1, $R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1–3 and M is a metal ion from the 1st, 2nd or 3rd group of the periodic table or is Zn, Cu, Ni or Co, or M is a group N$^{n+}$(R$_2$)$_4$ where $R_2$ is hydrogen, alkyl of 1 to 8 carbon atoms or benzyl, or when x is 2, $R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula D and D*, $R_{10}$ is as defined above, y is 1 to 4, and $R_{12}$ is defined as $R_2$ above, in formula E and E*, k is 1 or 2, when k is 1, $R_{20}$ and $R_2$, are independently alkyl of 1 to 12 carbon atoms, alkenyl of 2 to 12 carbon atoms or aralkyl of 7 to 15 carbon atoms, or $R_{20}$ is also hydrogen, or $R_{20}$ and $R_{21}$ together are alkylene of 2 to 8 carbon atoms or said alkylene substituted by hydroxyl, or are acyloxy-alkylene of 4 to 22 carbon atoms, or when k is 2

$R_{20}$ and $R_{21}$ are together (—CH$_2$)$_2$C(CH$_2$—)$_2$, in formula F and F*, $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, when g is 2, $R_{31}$ is defined as $R_1$ above when n is 2, in formula G and G*, $Q_1$ is —NR$_{41}$— or —O—, $E_1$ is alkylene of 1 to 3 carbon atoms, or $E_1$ is —CH$_2$—CH(R$_{42}$)—O— where R42 is hydrogen, methyl or phenyl, or $E_1$ is —(CH$_2$)$_3$—NH— or $E_1$ is a direct bond, $R_{40}$ is hydrogen or alkyl of 1 to 18 carbon atoms, $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —$CH_2$—$CH(R_{42})$—OH where $R_{42}$ is as defined above, in formula H and H*, p is 1 or 2, $T_4$ is as defined for $R_{11}$ when x is 1 or 2, M and Y are independently methylene or carbonyl, preferably M is methylene and Y is carbonyl, in formula I and I*, this formula denotes a recurring structural unit of a polymer where $T_1$ is ethylene or 1,2-propylene or is the repeating structural unit derived from an alpha-olefin copolymer with an alkyl acrylate or methacrylate, and where q is 2 to 100, $Q_1$ is —$N(R_{41})$— or —O— where $R_{41}$ is as defined above, in formula J and J*, r is 1 or 2, $T_7$ is as defined for $R_1$ when n is 1 or 2 in formula A, preferably $T_7$ is octamethylene when r is 2, in formula L and L*, u is 1 or 2, $T_{13}$ is as defined for $R_1$ when n is 1 or 2 in formula A, with the proviso that $T_{13}$ is not hydrogen when u is 1, in formula M and M*, $E_1$ and $E_2$, being different, each are —CO— or —$N(E_5)$— where $E_5$ is hydrogen, alkyl of 1 to 12 carbon atoms or alkoxycarbonylalkyl of 4 to 22 carbon atoms, preferably $E_1$ is —CO— and $E_2$ is —$N(E_5)$—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, preferably methyl, in formula N, $R_1$ is as defined for $R_1$ in formula A when n is 1, $G_3$ is a direct bond, alkylene of 1 to 12 carbon atoms, phenylene or —NH—$G_1$—NH— where $G_1$ is alkylene of 1 to 12 carbon atoms, in formula O and O*, $R_{10}$ is as defined for $R_{10}$ in formula C, in formula P and P*, $E_6$ is an aliphtic or aromatic tetravalent radical, preferably neopentanetetrayl or benzenetetrayl, in formula T and T*, $R_{51}$ is hydrogen, alkyl of 1 to 18 carbon atoms, cycloalkyl of 5 to 12 carbon atoms, or aryl of 6 to 10 carbon atoms, $R_{52}$ is hydrogen or alkyl of 1 to 18 carbon atoms, or $R_{51}$ and $R_{52}$ together of alkylene of 4 to 8 carbon atoms, f is 1 or 2, when f is 1, $R_{50}$ is as defined for $R_{11}$ in formula C when x is 1, or $R_{50}$ is —$(CH_2)_zCOOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl,.

when f is 2, $R_{50}$ is as defined for $R_{11}$ in formula C when x is 2, in formula U and U*, $R_{53}$, $R_{54}$, $R_{55}$ and $R_{56}$ are independently alkyl of 1 to 4 carbon atoms or are together pentamethylene.

in formula V and V*, $R_{57}$, $R_{58}$, $R_{59}$ and $R_{60}$ are independently alkyl of 1 to 4 carbon atoms or are together pentamethylene.

in formula W and W*, $R_{61}$, $R_{62}$, $R_{63}$ and $R_{64}$ are independently alkyl of 1 to 4 carbon atoms or are together pentamethylene, $R_{65}$ is alkyl of 1 to 5 carbon atoms, M is hydrogen or oxygen, wherein in formulas X to CC and X* to CC* n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_kO[(CH_2)_kO]_h(CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, and
Q is an alkali metal salt, ammonium or $N^+(G_1)_4$,
in formula DD and DD*
  m is 2 or 3,
  when m is 2, G is $-(CH_2CHR-O)_rCH_2CHR-$, where r is 0 to 3, and R is hydrogen or methyl, and
  when m is 3, G is glyceryl,
in formula EE and EE*
  $G_2$ is $-CN$, $-CONH_2$ or $-COOG_3$ where $G_3$ is hydrogen, alkyl of 1 to 18 carbon atoms or phenyl,
  X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and
  where the total charge of cations h is equal to the total charge of anions j, and with the proviso that bis(2,2,6,6-tetramethylpiperidin-4-yl) sebacate or the polycondensation product of 1-(2-hydroxyethyl)-2,2,6,6-tetramethyl-4-hydroxypiperidine and succinic acid are excluded.

Most preferably, the compounds of component (b) are those of formulas A, A*, B, B*, C, C*, D, D*, Q, Q*, R, R*, S, S*, X, X*, Y, Y*, Z and Z*,
  where E is oxyl or hydroxyl,
  R is hydrogen,
in formula A and A*
  n is 1 or 2,
  when n is 1,
  $R_1$ is hydrogen, alkyl of 1 to 6 carbon atoms, alkenyl of 2–6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or
  $R_1$ is alkyl of 1 to 4 carbon atoms substituted by a carboxy group or by $-COOZ$ where Z is hydrogen or alkyl of 1 to 4 carbon atoms,
  when n is 2,
  $R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups,
in formula B and B*
  m is 1 or 2
  when m is 1,
  $R_2$ is alkyl of 1 to 4 carbon atoms or $R_2$ is $CH_2(OCH_2CH_2)_nOCH_3$ where n is 1 to 12, or
  $R_2$ is phenyl, or said phenyl substituted by one to three methyl groups,
  $R_2$ is $-NHR_3$ where $R_3$ is alkyl of 1 to 4 carbon atoms or phenyl, or said phenyl substituted by one or two methyl groups,
  when m is 2,
  $R_2$ is alkylene of 1 to 8 carbon atoms, alkenylene of 4 to 8 carbon atoms, or $R_2$ is $-CH_2(OCH_2CH_2)_nOCH_2-$ where n is 1 to 12,
  $R_2$ is $NHR_4NH$ where $R_4$ is of 2 to 6 carbon atoms, aralkylene of 8 to 15 carbon atoms or arylene of 6 to 12 carbon atoms,
  $R_2$ is $-CO-$ or $-NHCONH$,
in formula C and C*,
  $R_{10}$ is hydrogen or, alkanoyl of 1 to 3 carbon atoms,
  x is 1 or 2,
  when x is 1,
  $R_{11}$ is hydrogen, alkyl of 1 to 6 carbon atoms or glycidyl,
  $R_{11}$ is alkyl of 1 to 4 carbon atoms substituted by a carboxy group or by COOZ where Z is hydrogen or alkyl of 1 to 4 carbon atoms,
  when x is 2,
  $R_{11}$ is alkylene of 1 to 6 carbon atoms,
in formula D and D*,
  $R_{10}$ is hydrogen,
  y is 1 or 2,
  $R_{12}$ is defined as $R_2$ above,
in formula Y, Y*, Z and Z*,
  x is 1 or 2,
  when x is 1,
  $R_1$ and $R_2$ are independently alkyl of 1 to 4 carbon atoms, or $R_1$ and $R_2$ are together tetramethylene, or pentamethylene,
  $R_2$ is hydrogen or alkyl of 1 to 4 carbon atoms, said alkyl group substituted by a hydroxyl group,
  when x is 2,
  $R_1$ is hydrogen, alkyl of 1 to 4 carbon atoms, said alkyl substituted by a hydroxyl group,
  $R_2$ is alkylene of 2 to 6 carbon atoms,
  $R_3$ is as defined above.

Especially preferred, the compounds of component (b) are those of formulas A, A*, B, B*, C, C*, D, D*, Q, Q*, R and R*,
  where E is oxyl or hydroxyl,
  R is hydrogen,
in formula A and A*,
  h is 1,
  $R_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
  $R_1$ is alkyl of 1 to 4 carbon atoms substituted by $-COOZ$ where Z is hydrogen or alkyl of 1 to 4 carbon atoms,
in formula B and B*,
  m is 1 or 2,
  $R_2$ is alkyl of 1 to 4 carbon atoms or $R_2$ is $CH_2(OCH_2CH_2)_nOCH_3$ where n is 1 to 4,
  when m is 2,
  $R_2$ is alkylene of 1 to 8 carbon atoms,
in formula C and C*,
  $R_{10}$ is hydrogen or alkanoyl of 1 or 2 carbon atoms,
  x is 1 or 2,
  when x is 1,
  $R_{11}$ is hydrogen, alkyl of 1 to 4 carbon atoms or glycidyl,
  $R_{11}$ is alkyl of 1 to 4 carbon atoms substituted by COOZ where Z is hydrogen or alkyl of 1 to 4 carbon atoms,
  when x is 2,
  $R_{11}$ is alkylene of 1 to 6 carbon atoms, in formula D and D*, R₁₀ is hydrogen, y is 1 or 2, R₁₂ is defined as R₂ above.

More particularly, the hindered amine compound is (a) bis(1-oxyl-2,2-6-6-tetramethylpiperidin-4-yl) sebacate;

(b) bis(1-hydroxy-2,2-6-6-tetramethylpiperidin-4-yl) sebacate;

(c) 1-hydroxy-2,2-6-6-tetramethyl-4-acetoxypiperidinium citrate;

(d) 1-oxyl-2,2,6,6-tetramethyl4-acetamidopiperidine;

(e) 1-hydroxy-2,2,6,6-tetramethyl-4-acetamidopiperidine;

(f) 1-hydroxy-2,2,6,6-tetramethyl-4-acetamidopiperidinium bisulfate;

(g) 1-oxyl-2,2,6,6-tetramethyl-4-oxo-piperidine;

(h) 1-hydroxy -2,2,6,6-tetramethyl-4-oxo-piperidine;

(i) 1-hydroxy -2,2,6,6-tetramethyl-4-oxo-piperidinium acetate;

(j) 1-oxyl-2,2,6,6-tetramethyl-4-methoxy-piperidine;

(k) 1-hydroxy-2,2,6,6-tetramethyl-4-methoxy-piperidine;

(I) 1-hydroxyl-2,2,6,6-tetramethyl-4-methoxy-piperidinium acetate;

(m) 1-oxyl-2,2,6,6-tetramethyl-4-acetoxypiperidine;

(n) 1-hydroxy-2,2,6,6-tetramethyl-4-acetoxypiperidine;

(o) 1-oxyl-2,2,6,6-tetramethyl-4-propoxy-piperidine;

(p) 1-hydroxy-2,2,6,6-tetramethyl-4-propoxy-piperidinium acetate;

(q) 1-hydroxy-2,2,6,6-tetramethyl-4-propoxy-piperidine;

(r) 1-oxyl-2,2,6,6-tetramethyl-4-(2-hydroxy4-oxapentoxy)piperidine;

(s) 1-hydroxy-2,2,6,6-tetramethyl-4-(2-hydroxy-4-oxapentoxy)piperidinium acetate;

(t) 1-oxyl-2,2,6,6-tetramethyl-4-hydroxypiperidine;

(u) 1-hydroxy-2,2,6,6-tetramethyl-4-hydroxypiperidine;

(v) 1-hydroxy-2,2,6,6-tetramethyl-4-hydroxypiperidinium chloride;

(w) 1-hydroxy-2,2,6,6-tetramethyl-4-hydroxypiperidinium acetate;

(x) 1-hydroxy-2,2,6,6-tetramethyl-4-hydroxypiperidinium bisulfate;

(y) 1-hydroxy-2,2,6,6-tetramethyl-4-hydroxypiperidinium citrate;

(z) bis(1-hydroxy-2,2,6,6-tetramethyl-4-hydroxypiperidinium) citrate;

(aa) tris(1-hydroxy-2,2,6,6-tetramethyl-4-hydroxypiperidinium) citrate.

(bb) tetra(1-hydroxy-2,2,6,6-tetramethyl-4-hydroxypiperidinium) ethylenediaminetetraacetic;

(cc) tetra(1-hydroxy-2,2,6,6-tetramethyl-4-acetamidopiperidinium) ethylenediaminetetraacetate;

(dd) tetra(1-hydroxy-2,2,6,6-tetramethyl-4-oxopiperidinium) ethylenediaminetetraacetate;

(ee) penta(1-hydroxy-2,2,6,6-tetramethyl-4-hydroxypiperidinium) diethylenetriaminepentaacetate;

(ff) penta(1-hydroxy-2,2,6,6-tetramethyl-4-acetamidopiperidinium) diethylenetriaminepentaacetate;

(gg) penta(1-hydroxy-2,2,6,6-tetramethyl-4-oxopiperidinium) diethylenetriaminepentaacetate;

(hh) tri(1-hydroxy-2,2,6,6-tetramethyl-4-hydroxypiperidinium) nitrilotriacetate;

(ii) tri(1-hydroxy-2,2,6,6-tetramethyl-4-acetamidopiperidinium) nitrilotriacetate;

(jj) tri(1-hydroxy-2,2,6,6-tetramethyl-4-oxopiperidinium) nitrilotriacetate;

(kk) penta(1-hydroxy-2,2,6,6-tetramethyl-4-hydroxypiperidinium) diethylenetriaminepentamethylenephosphonate;

(ll) penta(1-hydroxy-2,2,6,6-tetramethyl-4-acetamidopiperidinium) diethylenetriaminepentamethylenephosphonate;

(mm) penta(1-hydroxy-2,2,6 ,6-tetramethyl-4-oxopiperidinium) diethylenetriaminepentamethylenephosphonate;

Most especially, the hindered amine compound is (a) 1-oxyl-2,2,6,6-tetramethyl4-hydroxypiperidine;

(b) 1-hydroxy-2,2,6,6-tetramethyl-4-hydroxypiperidine;

(c) 1-hydroxy-2,2,6,6-tetramethyl-4-hydroxypiperidinium chloride;

(d) 1-hydroxy-2,2,6,6-tetramethyl-4-hydroxypiperidinium acetate;

(e) 1-hydroxy-2,2,6,6-tetramethyl-4-hydroxypiperidinium bisulfate;

(f) 1-hydroxy-2,2,6,6-tetramethyl-4-hydroxypiperidinium citrate;

(g) bis(1-hydroxy-2,2,6,6-tetramethyl-4-hydroxypiperidinium) citrate;

(h) tris(1-hydroxy-2,2,6,6-tetramethyl-4-hydroxypiperidinium) citrate;

(i) tetra(1-hydroxy-2,2,6,6-tetramethyl-4-hydroxypiperidinium) ethylenediaminetetraacetate;

(j) tetra(1-hydroxy-2,2,6,6-tetramethyl-4-acetamidopiperidinium) ethylenediaminetetraacetate;

(k) tetra(1-hydroxy-2,2,6,6-tetramethyl-4-oxopiperidinium) ethylenediaminetetraacetate;

(l) penta(1-hydroxy-2,2,6,6-tetramethyl-4-hydroxypiperidinium) diethylenetriaminepentaacetate;

(m) penta(1-hydroxy-2,2,6,6-tetramethyl-4-acetamidopiperidinium) diethylenetriaminepentaacetate;

(n) penta(1-hydroxy-2,2,6,6-tetramethyl-4-oxopiperidinium) diethylenetriaminepentaacetate.

The instant compositions may additionally include an effective amount of at least one coadditive selected from the group consisting of the UV absorbers, the polymeric inhibitors, the sulfur containing inhibitors, the phosphorus containing compounds, the nitrones, the benzofuran-2-ones and the hydroxylamines and mixtures thereof.

The compositions which also include a UV absorber are especially preferred. The UV absorber is selected from group consisting of the benzotriazoles, the s-triazines, the benzophenones, the α-cyanoacrylates, the oxanilides, the benzoxazinones, the benzoates and the α-alkyl cinnamates.

Preferably, the UV absorber is a benzotriazole, an s-triazine or a benzophenone, most especially a benzotriazole UV absorber or benzophenone UV absorber.

Typical and useful UV absorbers are, for example, (a) 5-chloro-2-(2-hydroxy-3,5-di-tert-butylphenyl)-2H-benzotriazole;

(b) 2-(2-hydroxy-3,5-di-tert-butylphenyl)-2H-benzotriazole;

(c) 2-(2-hydroxy-3,5-di-tert-amylphenyl)-2H-benzotriazole;

(d) 2-(2-hydroxy-3,5-di-α-cumylphenyl)-2H-benzotriazole;

(e) 2-(2-hydroxy-3-α-cumyl-5-tert-octylphenyl)-2H-benzotriazole;

(f) 2-(2-hydroxy-5-tert-octylphenyl)-2H-benzotriazole;

(g) 3-(2H-benzotriazol-2-yl)-4-hydroxy-5-(1-methylpropyl)-benzenesulfonic acid monosodium salt;

(h) 3-tert-butyl-4-hydroxy-5-(2H-benzotriazol-2-yl)-hydrocinnamic acid and sodium salt;

(i) 12-hydroxy-3,6,9-trioxadodecyl 3-tert-butyl-4-hydroxy-5-(2H-benzotriazol-2-yl)hydrocinnamate;

(j) octyl 3-tert-butyl-4-hydroxy-5-(2H-benzotriazol-2-yl)-hydrocinnamate;

(k) 4,6-bis(2,4-dimethylphenyl)-2-(4-(3-dodecyloxy*-2-hydroxypropoxy)-2-hydroxy phenyl)-s-triazine (*is mixture of $C_{12-14}$oxy isomers);

(l) 4,6-bis(2,4-dimethylphenyl)-2-(4-octyloxy-2-hydroxyphenyl)-s-triazine;

(m) 2,4-dihydroxybenzophenone;

(n) 2,2'-dihydroxy-4,4'-dimethoxy-5,5'-disulfobenzophenone, disodium salt;

(o) 2-hydroxy-4-octyloxybenzophenone;

(p) 2-hydroxy-4-dodecyloxybenzophenone;

(q) 2,4-dihydroxybenzophenone;

(r) 2,2',4,4'-tetrahydroxybenzophenone;

(s) 4-aminobenzoic acid;

(t) 2,3-dihydroxypropyl-4-aminobenzoic acid;

(u) 3-(4-imidazolyl)acrylic acid;

(v) 2-phenyl-5-benzimidazole sulfonic acid;

(w) N,N,N-trimethyl-α-(2-oxo-3-bornylidene)-p-toluidinium methyl sulfate;

(x) 5-benzoyl-4-hydroxy-2-methoxybenzenesulfonic acid, sodium salt;

(y) 3-(4-benzoyl-3-hydroxyphenoxy)-2-hydroxy-N,N,N-trimethyl-1-propanaminium chloride;

(z) 3-[4-(2H-benzotriazol-2-yl)-3-hydroxyphenoxy]-2-hydroxy-N,N,N-trimethyl-1-propanaminium, chloride;

(aa) 2-(2-hydroxy-5-methylphenyl)-2H-benzotriazole; and (bb) 2,2'-dihydroxy-4,4'-dimethoxybenzophenone (Uvinul® 3049).

Preferred UV absorbers are (a) 3-(2H-benzotriazol-2-yl)-4-hydroxy-5-(1-methylpropyl)-benzenesulfonic acid monosodium salt;

(b) 3-tert-butyl-4-hydroxy-5-(2H-benzotriazol-2-yl)-hydrocinnamic acid and sodium salt;

(c) 2-(2-hydroxy-3,5-di-tert-butylphenyl)-2H-benzotriazole;

(d) 2-(2-hydroxy-3,5-di-tert-amylphenyl)-2H-benzotriazole;

(e) 4,6-bis(2,4-dimethylphenyl)-2-(4-(3-dodecyloxy*-2-hydroxypropoxy)-2-hydroxy phenyl)-s-triazine (*is mixture of $C_{12-14}$oxy isomers);

(f) 12-hydroxy-3,6,9-trioxadodecyl 3-tert-butyl-4-hydroxy-5-(2H-benzotriazol-2-yl)hydrocinnamate;

(g) 2,4-dihydroxybenzophenone;

(h) 2,2'-dihydroxy-4,4'-dimethoxy-5,5'-disulfobenzophenone, disodium salt;

(i) 2,2',4,4'-tetrahydroxybenzophenone;

(j) 3-(4-benzoyl-3-hydroxyphenoxy)-2-hydroxy-N,N,N-trimethyl-1-propanaminium chloride;

(k) 3-[4-(2H-benzotriazol-2-yl)-3-hydroxyphenoxy]-2-hydroxy-N,N,N-trimethyl-1-propanaminium, chloride;

(l) 5-benzoyl-4-hydroxy-2-methoxy-benzenesulfonic acid, sodium salt (m) 2-(2-hydroxy-3-α-cumyl-5-tert-octylphenyl)-2H-benzotriazole.

Other preferred compositions are those which additionally contain a metal chelating agent, i.e. those that offer thermodynamic or kinetic control of metal ions. Examples kinetic controlling chelating agents are citrates, keto acids, gluconates, heptagluconates, phosphates, and phosphonates. Examples of chelating agents that offer thermodynamic control are the aminocarboxylic acid chelates. Well known and commercially available members of this class include ethylenediaminetetraacetic acid (EDTA), diethylenetriaminepentaacetic acid (DTPA), hydroxyethylethylenediaminetriacetic acid (HEDTA), nitrilotriacetic acid (NTA) and diethylenetriaminepentamethylenephosphonic acid (DTPMPA).

Still other preferred compositions are those which contain mixtures of thermodynamic and kinetic controlling chelating agents are also preferred.

Still other preferred compositions are those which additionally contain a polymeric inhibitor; preferably poly(ethylene glycol) (PEO), poly(propylene glycol) (PPO), poly(butylene glycol) (PTHF), poly(vinyl pyrrolidone) (PVP) or thiol-capped poly(ethylene glycol) as well as copolymers such as poly(ethylene/propylene glycol).

Still other preferred compositions are those which additional contain a fluorescent whitening agent selected from a wide range of chemical types such as 4,4'-bis-(triazinylamino)-stilbene-2,2'-disulfonic acids, 4,4'-bis-(triazol-2-yl)stilbene-2,2'-disulfonic acids, 4,4'-dibenzofuranyl-biphenyls, 4,4'-(diphenyl)-stilbenes, 4,4'-distyryl-biphenyls, 4-phenyl4'-benzoxazolyl-stilbenes, stilbenyl-naphthotriazoles, 4-styryl-stilbenes, bis-(benzoxazol-2-yl) derivatives, bis-(benzimidazol-2-yl) derivatives, coumarins, pyrazolines, naphthalimides, triazinyl-pyrenes, 2-styryl-benzoxazole or -naphthoxazoles, benzimidazole-benzofurans or oxanilides.

Some preferred compositions contain a mixture of additional stabilizers such as a mixture of a UV absorber and polymeric inhibitor; or a mixture of a UV absorber and a metal chelating agent; or a mixture of a polymeric inhibitor and a metal chelating agent; or a mixture of a polymeric inhibitor and a fluorescent whitening agent; or a mixture of a fluorescent whitening agent and a metal chelating agent; or a mixture of a UV absorber, metal chelating agent and a polymeric inhibitor; or a mixture of fluorescent whitening agent, metal chelating agent and polymeric inhibitor.

Preferably the compositions are those wherein the compound of formula I or II is of low molecular weight or contains hydrophilic moieties especially cationic groups, is both of low molecular weight and contains hydrophilic moieties.

The instant invention also pertains to a process for preventing the loss of brightness and for enhancing resistance to yellowing of chemimechanical or thermomechanical pulp or paper which still contains lignin, which comprises Treating said pulp or paper with an effective stabilizing amount of a compound of formula I or II, preferably a compound of formula A to EE or A* to EE* as described above.

Preferably the process is that where in the compound of formula A to EE or A* to EE*, E is oxyl or hydroxyl and most preferably E is hydroxyl.

The instant invention also pertains to new compounds of formula IV, V, VI, VII or VIII

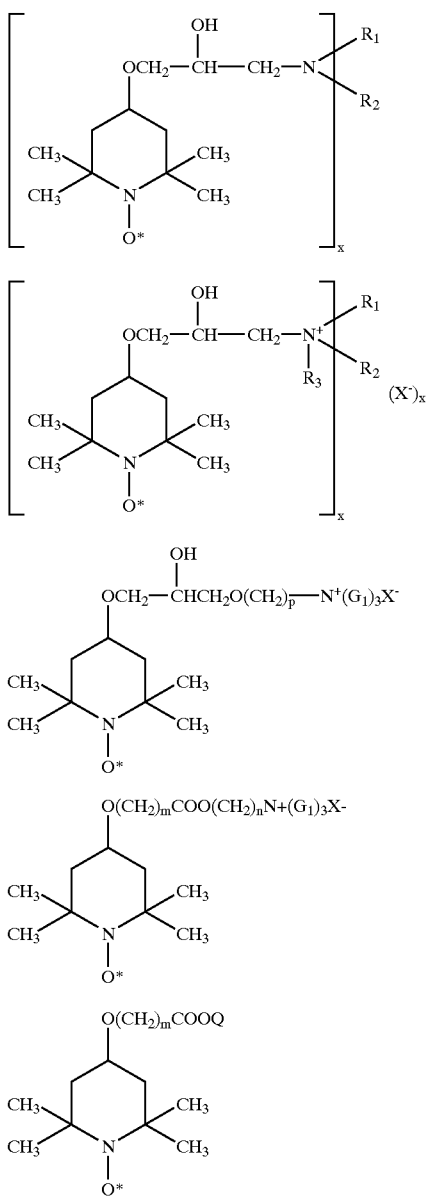

wherein n is 2 to 3, $G_1$ is hydrogen, methyl, ethyl, butyl or benzyl,

X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_kO[(CH_2)_kO]_h(CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, and Q is an alkali metal salt, ammonium or $N^+(G_1)_4$.

Preferably, in the compounds of formulas IV to VIII n is 2; $G_1$ is hydrogen or methyl; X is chloro or bromo; x is 1 or 2, $R_1$ and $R_2$ are independently alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, or $R_1$ is hydrogen; or $R_1$ and $R_2$ together are 3-oxapentamethylene; $R_3$ is hydrogen or alkyl of 1 to 2 carbon atoms, or said alkyl substituted by a hydroxyl group, p is 2, m is 1, and Q is $Na^+$, $NH_4^+$ or $N(CH_3)_4^+$.

Typical compounds falling within the structures of formulas IV to VIII and which are useful in this invention are:

(a) 1-oxyl-2,2,6,6-tetramethyl-4-(2-hydroxy-4-oxa-6-trimethylammmoniumhexyloxy)piperidine chloride;

(b) 1-oxyl-2,2,6,6-tetramethyl-4-(2-hydroxy-3-trimethylammoniumpropoxy)piperidine chloride;

(c) 1-oxyl-2,2,6,6-tetramethyl-4-{2-hydroxy-3-[di(2-hydroxyethyl)amino]propoxy}piperidine;

(d) 1-oxyl-2,2,6,6-tetramethyl-4-(2-hydroxy-3-dimethylaminopropoxy)piperidine;

(e) 1-oxyl-2,2,6,6-tetramethyl-4-(2-hydroxy-3-diethylaminopropoxy)piperidine;

(f) N,N'-dimethyl-N,N'-bis-[3-(1-oxyl-2,2,6,6-tetramethyl-piperidin-4-yloxy)-2-hydroxypropyl] hexamethylenediamine;

(g) N,N,N',N'-tetramethyl-N,N'-bis-[3-(1-oxyl-2,2,6,6-tetramethylpiperidin-4-yloxy)-2-hydroxypropyl]-hexamethylenediammonium dibromide;

(h) 1-oxyl-2,2,6,6-tetramethyl-4-[2-hydroxy-3-(N,N-dimethyl-N-propylammonium)propoxy]piperidine chloride;

(i) sodium 1-oxyl-2,2,6,6-tetramethylpiperidin-4-yloxyacetate; or (j) 1-oxyl-2,2,6,6-tetramethylpiperidin-4-yloxyacetic acid, choline ester.

The instant invention also pertains to novel hydroxylamine salts of formulae A*, D*, X*, Y*, Z*, M*, BB*, CC* and DD*,

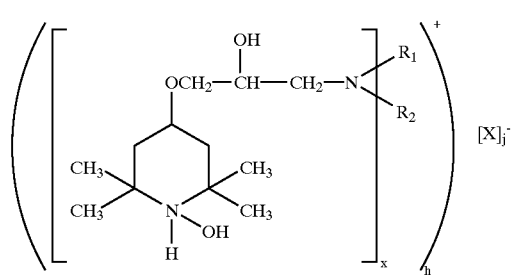
(A*)

(D*)

(X*)

(Y*)

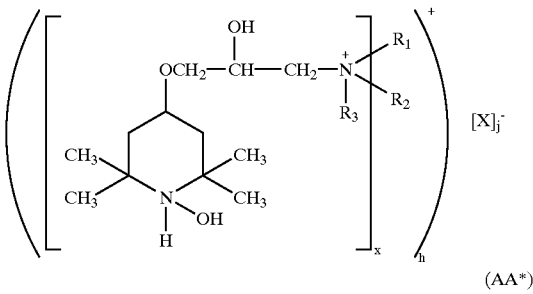
(Z*)

(AA*)

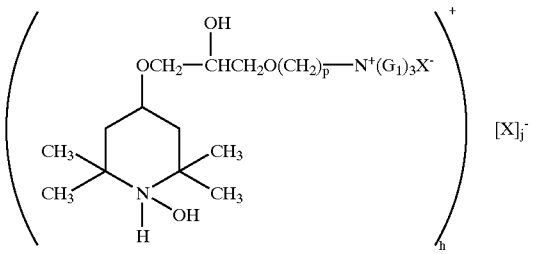
(BB*)

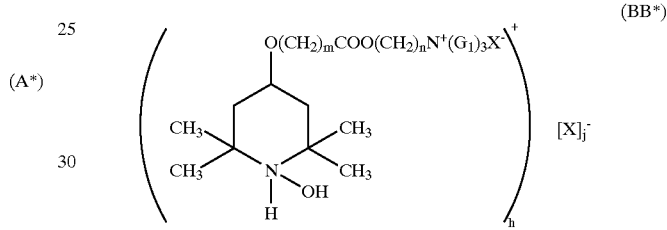
(CC*)

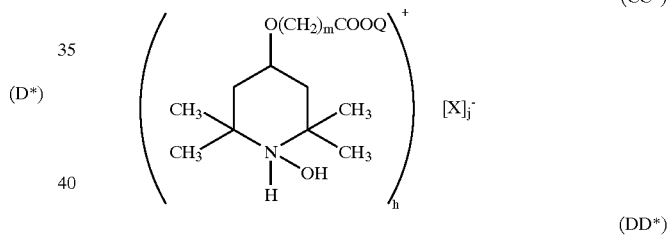
(DD*)

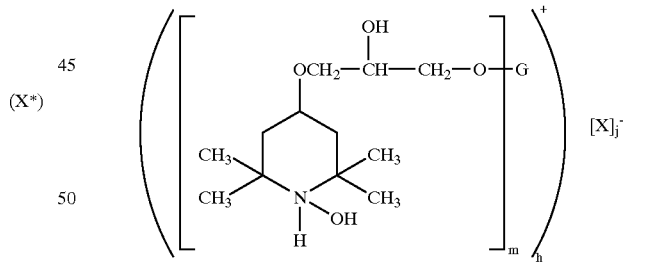

wherein

R is hydrogen, in formula A* n is 1, $R_1$ is hydrogen or alkyl of 1 to 4 carbon atoms, preferably hydrogen, in formula D* y is 1, $R_{10}$ is hydrogen or methyl, preferably hydrogen, $R_{12}$ is alkyl of 1 to 4 carbon atoms, preferably methyl, X is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, where the total charge of cations h is equal to the total charge of anions j, wherein in formulas X* to DD* n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_k$O[$(CH_2)_k$O]$_h$$(CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, and Q is an alkali metal salt, ammonium or $N^+(G_1)_4$, in formula DD and DD* m is 2 or 3, when m is 2, G is —$(CH_2CHR—O)_r CH_2CHR$—, where r is 0 to 3, and R is hydrogen or methyl, and when m is 3, G is glyceryl, with the proviso that in formula A* when $R_1$ is hydrogen, X is not chloride or bisulfate, and when in formula D* when $R_{10}$ is hydrogen and $R_{12}$ is methyl, X is not chloride or bisulfate.

Preferably, X is chloride, bisulfate, bisulfite, sulfate, nitrate, acetate, citrate or carboxylate of ethylenediaminetetraacetic acid or diethylenetriaminepentaacetic acid; most preferably, X is bisulfate or citrate.

Hydroxylamine salts of particular interest are (a) 1-hydroxy-2,2,6,6-tetramethyl-4-hydroxypiperidinium citrate;

(b) bis(1-hydroxy-2,2,6,6-tetramethyl-4-hydroxypiperidinium)citrate;

(c) tris(1-hydroxy-2,2,6,6-tetramethyl-4-hydroxypiperidinium)citrate;

(d) 1-hydroxy-2,2,6,6-tetramethyl-4-hydroxypiperidinium DTPA;

(e) bis(1-hydroxy-2,2,6,6-tetramethyl-4-hydroxypiperidinium)DTPA;

(f) tris(1-hydroxy-2,2,6,6-tetramethyl-4-hydroxypiperidinium)DTPA;

(g) tetrakis(1-hydroxy-2,2,6,6-tetramethyl-4-hydroxypiperidinium)DTPA;

(h) pentakis(1-hydroxy-2,2,6,6-tetramethyl-4-hydroxypiperidinium)DTPA;

(i) 1-hydroxy-2,2,6,6-tetramethyl-4-hydroxypiperidinium EDTA;

(j) bis(1-hydroxy-2,2,6,6-tetramethyl-4-hydroxypiperidinium)EDTA;

(k) tris(1-hydroxy-2,2,6,6-tetramethyl-4-hydroxypiperidinium)EDTA;

(l) tetrakis(1-hydroxy-2,2,6,6-tetramethyl-4-hydroxypiperidinium)EDTA;

(m) 1-hydroxy-2,2,6,6-tetramethyl-4-oxo-piperidinium citrate;

(n) bis(1-hydroxy-2,2,6,6-tetramethyl-4-oxo-piperidinium)citrate;

(o) tris(1-hydroxy-2,2,6,6-tetramethyl-4-oxo-piperidinium)citrate;

(p) 1-hydroxy-2,2,6,6-tetramethyl-4-oxo-piperidinium DTPA;

(q) bis(1-hydroxy-2,2,6,6-tetramethyl-4-oxo-piperidinium)DTPA;

(r) tris(1-hydroxy-2,2,6,6-tetramethyl-4-oxo-piperidinium)DTPA;

(s) tetrakis(1-hydroxy-2,2,6,6-tetramethyl-4-oxo-piperidinium)DTPA;

(t) pentakis(1-hydroxy-2,2,6,6-tetramethyl-4-oxo-piperidinium)DTPA;

(u) 1-hydroxy-2,2,6,6-tetramethyl-4-oxo-piperidinium EDTA;

(v) bis(1-hydroxy-2,2,6,6-tetramethyl-4-oxo-piperidinium)EDTA;

(w) tris(1-hydroxy-2,2,6,6-tetramethyl-4-oxo-piperidinium)EDTA;

(x) tetrakis(1-hydroxy-2,2,6,6-tetramethyl-4-oxo-piperidinium)EDTA;

(y) 1-hydroxy-2,2,6,6-tetramethyl-4-acetamidopiperidinium citrate;

(z) bis(1-hydroxy-2,2,6,6-tetramethyl-4-acetamidopiperidinium)citrate;

(aa) tris(1-hydroxy-2,2,6,6-tetramethyl-4-acetamidopiperidinium)citrate;

(bb) 1-hydroxy-2,2,6,6-tetramethyl-4-acetamidopiperidinium DTPA;

(cc) bis(1-hydroxy-2,2,6,6-tetramethyl-4-acetamidopiperidinium)DTPA;

(dd) tris(1-hydroxy-2,2,6,6-tetramethyl-4-acetamidopiperidinium)DTPA;

(ee) tetrakis(1-hydroxy-2,2,6,6-tetramethyl-4-acetamidopiperidinium)DTPA;

(ff) pentakis(1-hydroxy-2,2,6,6-tetramethyl-4-acetamidopiperidinium)DTPA;

(gg) 1-hydroxy-2,2,6,6-tetramethyl-4-acetamidopiperidinium EDTA;

(hh) bis(1-hydroxy-2,2,6,6-tetramethyl-4-acetamidopiperidinium)EDTA;

(ii) tris(1-hydroxy-2,2,6,6-tetramethyl-4-acetamidopiperidinium)EDTA;

(jj) tetrakis(1-hydroxy-2,2,6,6-tetramethyl-4-hydroxypiperidinium)EDTA;

(kk) 1-hydroxy-2,2,6,6-tetramethyl-4-acetoxypiperidinium citrate;

(II) bis(1-hydroxy-2,2,6,6-tetramethyl-4-acetoxypiperidinium)citrate;

(mm) tris(1-hydroxy-2,2,6,6-tetramethyl-4-acetoxypiperidinium)citrate;

(nn) 1-hydroxy-2,2,6,6-tetramethyl-4-acetoxypiperidinium DTPA;

(oo) bis(1-hydroxy-2,2,6,6-tetramethyl-4-acetoxypiperidinium)DTPA;

(pp) tris(1-hydroxy-2,2,6,6-tetramethyl-4-acetoxypiperidinium)DTPA;

(qq) tetrakis(1-hydroxy-2,2,6,6-tetramethyl-4-acetoxypiperidinium)DTPA;

(rr) pentakis(1-hydroxy-2,2,6,6-tetramethyl-4-acetoxypiperidinium)DTPA;

(ss) 1-hydroxy-2,2,6,6-tetramethyl-4-acetoxypiperidinium EDTA;

(tt) bis(1-hydroxy-2,2,6,6-tetramethyl-4-acetoxypiperidinium)EDTA;

(uu) tris(1-hydroxy-2,2,6,6-tetramethyl-4-acetoxypiperidinium)EDTA or (vv) tetrakis(1-hydroxy-2,2,6,6-tetramethyl-4-acetoxypiperidinium)EDTA.

Nitroxides, hydroxylamines and their salts alone or in combination with UV absorbers are also effective in improving the resistance to yellowing of mechanical pulps which have been modified by acylation, alkylation, treatment with sodium borohydride or hydrogenated.

The intermediates needed to make the instant compounds are largely items of commerce.

The effective stabilizing amounts of the hindered amine is 0.001 to 5% by weight based on the pulp or paper. Preferably, the effective stabilizing amount is 0.005 to 2% by weight; preferably 0.01 to 1% by weight.

When a coadditive is also present, the effective amount of the coadditives is also 0.001 to 5% by weight based on the pulp or paper; preferably 0.005 to 2% by weight; most preferably 0.01 to 2% by weight.

The instant inhibitor additive system can be added to pulp or paper at a number of places during the manufacturing or processing operations. These include a. on a pulp slurry in the latency chest;

b. on a pulp slurry in or after the bleaching stage in a storage, blending or transfer chest;

c. on pulp during or after bleaching, washing and dewatering followed by cylinder or flash drying;

d. before or after the cleaners;

e. before or after the fan pump to the paper machine headbox;

f. to the paper machine white water;

g. to the silo or save all;

h. in the press section using a size press, coater or spray bar;

i. in the drying section using a size press, coater or spray bar;

j. on the calender using a wafer box;

k. on paper in an off-machine coater or size press; and/or.

l. in the curl control unit.

Clearly, the precise location where the stabilizer additives should be added will depend on the specific equipment involved, the exact process conditions being used and the like. In some cases, the additives may be added at one or more locations for most effectiveness.

At these various locations, the instant inhibitor additive system can also be added with a carrier or additive typically used in paper making, such as retention aids, sizing aids and solutions, starches, precipitated calcium carbonate, ground calcium carbonate, or other clays or fillers, and brightening additives.

The following examples are for illustrative purposes only and are not to be construed to limit the instant invention in any manner whatsoever.

Handsheet Treatment

All additives are applied by syringe-injecting the appropriate weight % of additive combination in either an aqueous solution when the additive is water soluble, or a solution in 1:1 (ethanol/dioxane) onto bleached thermomechanical pulp (BTMP) brightness squares (4 cm×4 cm). The clamped sheets are allowed to air dry for one day.

The brightness of the handsheets is recorded before and after treatment by light exposure.

Accelerated testing is carried out by subjecting the treated sheets to accelerated light induced yellowing in a fan-cooled light box containing eight fluorescent lamps with a spectral maximum output at 5700 Å with a total output approximately 43 times greater than normal office fluorescent lamps. The lamps are only about ten inches away from the handsheets being illuminated.

Ambient testing is carried out by placing the treated handsheets on a desk under normal cool-white fluorescent office lights at a nominal distance of six feet.

In both case ISO brightness is tracked as a function of photolysis time and converted to post color number (PC number) in the usual manner. (Giertz, Svensk Papperstidn, (1945) 48 (13), 317)

Post color (PC) number is defined as follows:

$PC=[(k/s)_{after}-(k/s)_{before}]\times 100$ $k/s=(1-R_{inf})^2/2R_{inf}$ where k and s are the absorption and scattering coefficients, respectively, and $R_{inf}$ is the value of ISO brightness.

The relationship between $R_{inf}$ and the chromophore concentration is non-linear, whereas, the PC number is roughly linearly related to the concentration of the chromophore in the sample.

Low PC numbers are desired as they indicate less yellowing.

When using the ambient test conditions untreated BTMP handsheets are compared to Kraft handsheets, after 60 days the BTMP handsheets have a PC number which is about 10 while the Kraft paper has a PC number which is 0.388742. The Kraft handsheets are clearly less yellow than untreated BTMP handsheets after exposure to ambient light.

The incident light flux for the accelerated yellowing experiments (Examples 1–4) is 43 times greater than normal office fluorescent lamps as measured by the A. W. Speery SLM-110 digital light power meter. The brightness of the handsheets is tracked and compared to that of untreated sheets exposed in the same manner. The treated sheets exhibit significant resistance to yellowing as seen below.

Materials Used in the Examples

Compound A is 1-hydroxy-2,2,6,6-tetramethyl-4-hydroxypiperidine;

Compound B is 1-oxyl-2,2,6,6-tetramethyl-4-hydroxypiperidine;

Compound C is 1-oxyl-2,2,6,6-tetramethyl-4-acetamidopiperidine;

Compound D is 1-oxyl-2,2,6,6-tetramethylpiperidine TEMPO;

Compound E is bis(1-oxyl-2,2,6,6-tetramethylpiperidin-4-yl)sebacate;

Compound F is 1-hydroxy-2,2,6,6-tetramethyl-4-hydroxypiperidinium chloride;

Compound G is 1-hydroxy-2,2,6,6-tetramethyl-4-hydroxypiperidinium bisulfate;

Compound H is bis(1-hydroxy-2,2,6,6-tetramethyl-4-hydroxypiperidinium)sulfate;

Compound I is 1-hydroxy-2,2,6,6-tetramethyl-4-hydroxypiperidinium acetate;

Compound J is pentakis(1-hydroxy-2,2,6,6-tetramethyl-4-hydroxypiperidinium)diethylenetriaminepentaacetic acid;

Compound K is 3-(4-benzyloxy-2,2,6,6-tetramethyl-piperidin-1-yloxy)-propionic acid methyl ester;

Compound L is 3-(4-{4-[1-(2-methoxycarbonyl-ethoxy)-2,2,6,6-tetramethyl-piperidin-4-yloxymethyl]-benzyloxy}-2,2,6,6-tetramethyl-piperidin-1-yloxy)-propionic acid methyl ester;

Compound M is 2,2-diethyl-malonic acid bis-(1-butylcarbamoyloxy-2,2,6,6-tetramethyl-piperidin-4-yl) ester;

Compound N is acetic acid 4-hydroxy-2,2,6,6-tetramethyl-piperidin-1-yl ester;

Compound O is benzoic acid 1-butoxycarbonyloxy-2,2,6,6-tetramethyl-piperidin-4-yl ester;

Compound P is 2,2,6,6-tetramethyl-1-(1-phenyl-ethoxy)-piperidin-4-ol;

Compound Q is 2,4-dihydroxybenzophenone;

Compound R is 12-hydroxy-3,6,9-trioxadodecyl-3-tert-butyl-4-hydroxy-5-(2H-benzotriazol-2-yl)-hydrocinnamate (Tinuvin® 1130);

Compound S is, 3-(2H-benzotriazol-2-yl)-4-hydroxy-5-(1-methylpropyl)-benzenesulfonic acid monosodium salt (Cibafast® W);

Compound T is 1-oxyl-2,2,6,6-tetramethyl-4-(2,3-dihydroxypropoxy)piperidine;

Compound U is 1-oxyl-2,2,6,6-tetramethyl-4-(carboxymethoxy)piperidine;

Compound V is 3-oxyl-1,2,2,4,4-pentamethyl-3,4-dihydro-2.H.-imidazol-1-ium methylsulfate;

Compound W is 3-(3-benzotriazol-2-yl-5-.tert.-butyl-4-hydroxy-phenyl)-propionic acid;

Compound X is polyethylene glycol of molecular weight 300 (PEO);

Compound Y is 4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers) (Tinuvin® 400);

Compound Z is 2,2'-dihydroxy-4,4'-dimethoxy-5,5'-disulfobenzophenone, disodium salt (Uvinul® 3048);

Compound AA is 2,2'-dihydroxy-4,4'-dimethoxybenzophenone (Uvinul® 3049);

Compound BB is diethylenetriamine tetraacidic acid (DTPA);

Compound CC is 5,5-dimethyl-1-pyrroline N-oxide;

Compound DD is N-tert-butyl-α-phenylnitrone;

Compound EE is 1-oxyl-2,2,6,6-tetramethyl-4-oxo-piperidine;

Compound FF is tris(1-hydroxy-2,2,6,6-tetramethyl-4-hydroxypiperidinium)citrate;

Compound GG is dithiothreitol;

Compound HH is 1-thioglycerol;

Compound II is 2,2'-oxydiethanethiol;

Compound JJ is 2,2,6,6-tetramethyl-4-acetamidopiperidine;

Compound KK is UVINUL® 3000, 2,4-dihydroxybenzophenone;

Compound LL is Brightener 28; 4,4'-bis[4-anilino-6-(bis(2-hydroxyethyl)amino-s-triazin-2-yl]amino-2,2'-stilbenedisulfonic acid, disodium salt;

TMHP is 2,2,6,6-tetramethyl-4-hydroxypiperidine.

EXAMPLE 1

Accelerated Yellowing with High Intensity Lamps

A BTMP sheet is treated with 0.5%–0.1% by weight of Compound A. The sheets treated with Compound A exhibit substantial inhibition to yellowing compared to the untreated control sheet as seen by the PC numbers.

| Time in Days | Concentration | | | | | |
|---|---|---|---|---|---|---|
| | 0.5% | 0.4% | 0.3% | 0.2% | 0.1% | Blank |
| | PC Number | | | | | |
| 1.0 | 1.63 | 1.51 | 1.56 | 1.67 | 2.13 | 5.51 |
| 2.1 | 3.05 | 2.94 | 3.12 | 3.35 | 4.2 | 9.97 |
| 3.0 | 4.17 | 4.09 | 4.37 | 4.76 | 5.92 | 13.14 |
| 4.0 | s.35 | 5.26 | 5.56 | 6.01 | 6.82 | 15.85 |
| 5.0 | 6.28 | 6.35 | 6.76 | 7.24 | 8.97 | 18.07 |
| 6.1 | 7.43 | 7.52 | 7.87 | 8.54 | 10.42 | 20.4 |
| 7.0 | 8.46 | 8.66 | 9.1O | 9.88 | 12.09 | 23.63 |

Even levels as low as 0.1% by weight of Compound A show effective stabilization effects.

EXAMPLE 2

Accelerated Yellowing with High Intensity Lamps

BTMP sheets are treated with 0.50% by weight of various hydroxylamine compounds by the procedure of Example 1.

1-hydroxy-2,2,6,6-tetramethyl-1,2,3,6-tetrahydro-pyridine;

1-hydroxy-2,2,6,6-tetramethyl-4-methoxypiperidine;

1-hydroxy-2,2,6,6-tetramethyl-4-ethoxypiperidine;

1-hydroxy-2,2,6,6-tetramethyl-4-propoxypiperidine;

1-hydroxy-2,2,6,6-tetramethyl-4-(2-hydroxy-4-oxapentoxy)piperidine;

4,4'-[1,6-hexanediylbis(formylimino)]bis[2,2,6,6-tetramethyl-1-hydroxypiperdine;

2-(8-carboxyoctyl)-4,4-dimethyl-2-octyl-3-hydroxy-oxazolidine;

3,3-dimethyl-4-hydroxy-1-oxa-4-azaspiro[4.5]decane:

3-aminomethyl-2,2,5,5-tetramethyl-1-hydroxy-pyrrolidine;

3-carboxy-2,2,5,5-tetramethyl-1-hydroxypyrrolidine:

4-phenyl-2,2,5,5-tetramethyl-1-hydroxy-3-imidazoline;

4-phenyl-2,2,5,5-tetramethyl-1-hydroxy-3-imidazoline-3-oxide;

di-tert-butyl hydroxylamine.

The sheets treated with hydroxylamines exhibit substantial inhibition to yellowing compared to the untreated control sheet.

EXAMPLE 3

Accelerated Yellowing with High Intensity Lamps

BTMP sheets are treated with 0.25% by weight of Compounds B, C, D and E. The sheets treated with nitroxides exhibit substantial inhibition to yellowing compared to the untreated control sheet.

|  | Compounds | | | | |
|---|---|---|---|---|---|
| Time in Days | Blank | B | C | D | E |
|  | PC Number | | | | |
| 0 | 0 | 0 | 0 | 0 | 0 |
| 0.93 | 2.49 | 0.88 | 1.6 | 2.01 | 1.28 |
| 1.9 | 5.27 | 1.89 | 3.24 | 4.06 | 2.49 |
| 2.94 | 8.46 | 3.41 | 5.52 | 6.73 | 4.28 |
| 3.93 | 10.54 | 4.36 | 6.89 | 8.57 | 5.4 |
| 4.98 | 12.34 | 5.36 | 8.31 | 10.5 | 6.53 |
| 5.88 | 13.81 | 6.11 | 9.45 | 11.62 | 7.74 |
| 6.91 | 15.55 | 7.17 | 11.05 | 13.17 | 8.81 |
| 7.98 | 17.34 | 8.18 | 12.5 | 14.57 | 10.12 |
| 8.97 | 19.44 | 9.33 | 13.72 | 16.28 | 11.32 |
| 10.01 | 20.98 | 10.1 | 15.07 | 17.75 | 12.21 |
| 10.94 | 22.35 | 11.01 | 16.3 | 19.1 | 13.16 |

EXAMPLE 4

Accelerated Yellowing with High Intensity Lamps

BTMP sheets are treated with 0.25% by weight of Compound EE. The sheets treated with nitroxides exhibit substantial inhibition to yellowing compared to the untreated control sheet.

| Time in Days | Compound EE PC Number | Blank |
|---|---|---|
| 0 | 0 | 0 |
| 1.04 | 1.77 | 4.53 |
| 2.02 | 3.77 | 7.91 |
| 3.06 | 5.97 | 11.16 |
| 4.02 | 7.76 | 13.72 |
| 5.02 | 9.28 | 15.47 |
| 6.23 | 10.49 | 17.61 |
| 6.98 | 11.88 | 18.78 |
| 7.98 | 13.06 | 20.09 |
| 10.96 | 16.92 | 25.25 |

EXAMPLE 5

Accelerated Yellowing with High Intensity Lamps

BTMP sheets are treated with 0.25% by weight of each of the following compounds:

1-oxyl-2,2,6,6-tetramethyl-1,2,3,6-tetrahydro-pyridine;

1-oxyl-2,2,6,6-tetramethylpiperidin-4-yl-acetate;

1-oxyl-2,2,6,6-tetramethylpiperidin-4-yl-2-ethylhexanoate;

1-oxyl-2,2,6,6-tetramethylpiperidin-4-yl-stearate;

1-oxyl-2,2,6,6-tetramethylpiperidin-4-yl-benzoate;

1-oxyl-2,2,6,6-tetramethylpiperidin-4-yl-(4-tert-butyl)benzoate;

bis(1-oxyl-2,2,6,6-tetramethylpiperidin-4-yl)-succinate;

bis(1-oxyl-2,2,6,6-tetramethylpiperidin-4-yl)-adipate;

bis(1-oxyl-2,2,6,6-tetramethylpiperidin-4-yl)-n-butylmalonate;

bis(1-oxyl-2,2,6,6-tetramethylpiperidin-4-yl)-phthalate;

bis(1-oxyl-2,2,6,6-tetramethylpiperidin-4-yl)-isophthalate;

bis(1-oxyl-2,2,6,6-tetramethylpiperidin-4-yl)-terephthalate;

bis(1-oxyl-2,2,6,6-tetramethylpiperidin-4-yl)-hexahydroterephthalate;

N,N'-bis(1-oxyl-2,2,6,6-tetramethylpiperidin-4-yl)-adipinamide;

N-(1-oxyl-2,2,6,6-tetramethylpiperidin-4-yl)-caprolactam;

N-(1-oxyl-2,2,6,6-tetramethylpiperidin-4-yl)-dodecylsuccinimide;

2,4,6-tris-[N-butyl-N-(1-oxyl-2,2,6,6-tetramethylpiperidin-4-yl]-s-triazine;

4,4'-ethylenebis(1-oxyl-2,2,6,6-tetramethylpiperazin-3-one;

tris-(2,2,6,6-tetramethyl-1-oxyl-piperidin-4-yl)phosphite;

1-oxyl-2,2,6,6-tetramethyl-4-methoxypiperidine;

1-oxyl-2,2,6,6-tetramethyl-4-ethoxypiperidine;

1-oxyl-2,2,6,6-tetramethyl-4-propoxypiperidine;

1-oxyl-2,2,6,6-tetramethyl-4-carboxypiperidine;

1-oxyl-2,2,6,6-tetramethyl-4-(2-hydroxy-4-oxapentoxy)piperidine;

4,4'-[1,6-hexanediylbis(formylimino)]bis[2,2,6,6-tetramethyl-1-piperdinyloxy;

2-(8-carboxyoctyl)-4,4-dimethyl-2-octyl-3-oxazolidinyloxy;

3,3-dimethyl-1-oxa-4-azaspiro[4.5]dec-4-yloxy;
3-aminomethyl-2,2,5,5-tetramethyl-1-pyrrolidinyloxy;
3-carboxy-2,2,5,5-tetramethyl-1-pyrrolidinyloxy;
4-phenyl-2,2,5,5-tetramethyl-3-imidazolin-1-yloxy;
4-phenyl-2,2,5,5-tetramethyl-3-imidazolin-1-yloxy-3-oxide;
di-tert-butyl nitroxide.

The sheets treated with nitroxides exhibit substantial inhibition to yellowing compared to the untreated control sheet.

EXAMPLE 6

Accelerated Yellowing with High Intensity Lamps

BTMP sheets are treated with 0.50% by weight of Compounds A, F, G, H, I and J. The sheets treated with hydroxylamine salts exhibit substantial inhibition to yellowing compared to the untreated control sheet.

| Time in Days | Blank | A | F | G | H | I | J |
|---|---|---|---|---|---|---|---|
| | | | PC Numbers | | | | |
| 0 | 0 | 0 | 0 | 0 | 0 | 0 | 0 |
| 0.77 | 3.62 | 0.90 | 1.26 | 1.42 | 1.23 | 1.02 | 1.08 |
| 1.74 | 6.27 | 1.69 | 2.29 | 2.60 | 2.08 | 1.97 | 1.98 |
| 2.81 | 8.82 | 2.50 | 3.23 | 3.54 | 2.92 | 2.8 | 2.84 |
| 3.8 | 10.97 | 3.25 | 4.20 | 5.0 | 3.85 | 3.65 | 3.66 |
| 4.75 | 12.86 | 4.08 | 5.01 | 5.52 | 4.60 | 4.3 | 4.44 |
| 5.81 | 14.68 | 4.88 | 5.95 | 6.6 | 5.5 | 5.08 | 5.36 |
| 6.79 | 16.24 | 5.62 | 6.81 | 7.51 | 6.27 | 5.85 | 6.0 |
| 7.8 | 17.36 | 6.09 | 7.40 | 8.42 | 6.97 | 6.36 | 6.56 |
| 8.76 | 18.44 | 6.71 | 8.13 | 9.24 | 7.7 | 7.02 | 7.13 |
| 9.75 | 19.41 | 7.33 | 8.76 | 9.95 | 8.3 | 7.62 | 7.72 |
| 10.8 | 20.35 | 7.85 | 9.43 | 10.68 | 8.92 | 8.26 | 8.2 |
| 11.87 | 21.13 | 8.34 | 9.98 | 11.36 | 9.46 | 8.68 | 8.6 |
| 12.81 | 21.98 | 8.77 | 10.52 | 12.12 | 9.98 | 9.10 | 9.06 |

EXAMPLE 7

Accelerated Yellowing with High Intensity Lamps

BTMP sheets are treated with 0.50% by weight of Compounds K and L. The sheets treated with hindered amine hydroxylamine Compounds K and L exhibit substantial inhibition to yellowing compared to the untreated control sheet.

| Time in Days | Blank | K | L |
|---|---|---|---|
| | PC Number | | |
| 0 | 0 | 0 | 0 |
| .81 | 3.19 | 1.42 | 1.59 |
| 1.82 | 5.85 | 2.62 | 3.02 |
| 2.8 | 8.06 | 3.93 | 4.41 |
| 3.75 | 10.02 | 4.79 | 5.42 |
| 4.83 | 12.08 | 5.85 | 6.61 |
| 5.8 | 13.81 | 7.35 | 7.52 |
| 6.76 | 15.49 | 7.73 | 8.40 |
| 7.77 | 16.98 | 8.39 | 9.2 |
| 8.74 | 18.54 | 9.34 | 10.36 |
| 9.76 | 20.06 | 10.02 | 11.18 |
| 10.74 | 21.56 | 11.06 | 12.24 |

EXAMPLE 8

Accelerated Yellowing with High Intensity Lamps

BTMP sheets are treated with 0.50% by weight of Compounds M, N and O. The sheets treated with selected hydroxylamine derivatives exhibit substantial inhibition to yellowing compared to the untreated control sheet.

| Time in Days | Blank | M | N | O |
|---|---|---|---|---|
| | | PC Number | | |
| 0 | 0 | 0 | 0 | 0 |
| .82 | 3.87 | 2.06 | 2.02 | 2.05 |
| 2.72 | 8.9 | 5.28 | 4.87 | 5.13 |
| 3.76 | 10.88 | 6.53 | 6.03 | 6.42 |
| 4.76 | 15.59 | 7.72 | 7.17 | 7.62 |
| 5.76 | 14.32 | 8.92 | 8.28 | 8.77 |
| 6.77 | 16.36 | 10.42 | 9.61 | 10.24 |
| 7.81 | 18.47 | 11.97 | 10.94 | 11.7 |
| 8.79 | 20.15 | 13.14 | 12.01 | 12.86 |
| 10 | 21.9 | 14.31 | 13.08 | 13.96 |
| 10.77 | 23.5 | 15.51 | 14.02 | 15.16 |

EXAMPLE 9

Accelerated Yellowing with High Intensity Lamps

BTMP sheets are treated with 0.5% by weight of each of the following:

1-acetyl-4-hydroxy-2,2,6,6-tetramethyl-piperidine;
1-acetyl-2,2,6,6-tetramethyl-piperidin-4-one;
bis(1-acetyl-2,2,6,6-tetramethylpiperidin-4-yl)sebacate.

The sheets treated with acylated hindered amine derivatives exhibit substantial inhibition to yellowing compared to the untreated control sheet.

EXAMPLE 10

Accelerated Yellowing with High Intensity Lamps

BTMP sheets are treated with 0.50% by weight of Compound P. The sheets treated with Compound P exhibit substantial inhibition to yellowing compared to the untreated control sheet.

| Time in Days | Blank PC Number | Compound P |
|---|---|---|
| 0 | 0 | 0 |
| .81 | 3.19 | 1.66 |
| 1.82 | 5.85 | 2.68 |
| 2.8 | 8.06 | 3.76 |
| 3.75 | 10.02 | 4.64 |

-continued

| Time in Days | Blank PC Number | Compound P |
|---|---|---|
| 4.83 | 12.08 | 5.50 |
| 5.8 | 13.81 | 6.28 |
| 6.76 | 15.49 | 7.21 |
| 7.77 | 16.98 | 7.90 |
| 8.74 | 18.54 | 8.9 |
| 9.76 | 20.06 | 9.63 |
| 10.74 | 21.56 | 10.47 |

EXAMPLE 11

Accelerated Yellowing with High Intensity Lamps

BTMP sheets are treated with 0.5%–0.1% by weight of Compound A and 0.5% by weight of Compound Q. The sheets treated with a combination of hydroxylamine and benzophenone UVA exhibit substantial inhibition to yellowing compared to the treated control sheet.

| | Concentration of Compound A | | | | | |
|---|---|---|---|---|---|---|
| Time in Days | 0.50 | 0.40 | 0.30 | 0.20 | 0.10 | Blank |
| | PC Number | | | | | |
| 0 | 0 | 0 | 0 | 0 | 0 | 0 |
| 1 | 1.05 | 0.73 | 0.71 | 0.93 | 0.86 | 5.74 |
| 2.1 | 2.17 | 1.63 | 1.6 | 2.11 | 2.02 | 10.51 |
| 2.98 | 3.05 | 2.48 | 2.43 | 3.12 | 3.09 | 13.75 |
| 3.98 | 4.12 | 3.41 | 3.39 | 4.37 | 4.2 | 16.67 |
| 4.97 | 4.95 | 4.22 | 4.16 | 5.39 | 5.15 | 18.96 |
| 6.05 | 5.95 | 5.18 | 5.18 | 6.59 | 6.36 | 21.42 |

EXAMPLE 12

Accelerated Yellowing with High Intensity Lamps

BTMP sheets are treated with 0.25% by weight of Compound A and 0.5% by weight of the UVA compounds R and S. The sheets treated with a combination of hydroxylamine and benzotriazole UVA exhibit substantial inhibition to yellowing compared to the untreated control sheet and illustrate the performance enhancement when combinations of hydroxylamine and UVA are used.

| | | Compound | | |
|---|---|---|---|---|
| Time in Days | 0.25% A | 0.25% A 0.5% R | 0.25% A 0.5% S | Blank |
| | PC Number | | | |
| 0 | 0 | 0 | 0 | 0 |
| 0.77 | 0.97 | 0.21 | 0.21 | 3.74 |
| 1.85 | 1.86 | 0.48 | 0.54 | 7.25 |
| 2.78 | 2.85 | 0.8 | 0.83 | 10.43 |
| 5.84 | 6.42 | 2.23 | 2.38 | 19.5 |
| 6.93 | 7.85 | 2.93 | 3.05 | 21.69 |
| 8 | 8.82 | 3.32 | 3.38 | 23.25 |

EXAMPLE 13

Accelerated Yellowing with High Intensity Lamps

BTMP sheets are treated with 0.25% by weight of Compounds B, T, U and V and 0.5% by weight of the UVA compound S. The sheets treated with a combination of nitroxide and UVA exhibit substantial inhibition to yellowing compared to the untreated control sheet and illustrate the performance enhancement when combinations of nitroxide and UVA are used.

| Time in Days | 0.25% B 0.5% S | 0.25% T 0.5% S | 0.25% U 0.5% S | 0.25% V 0.5% S | 0.5% S | Blank |
|---|---|---|---|---|---|---|
| | PC Number | | | | | |
| 0 | 0 | 0 | 0 | 0 | 0 | 0 |
| 0.9 | 0.54 | 1.02 | 1.01 | 0.29 | 3.37 | 4.24 |
| 1.9 | 1.12 | 2.06 | 2 | 2.12 | 6.49 | 7.81 |
| 2.9 | 1.86 | 3.19 | 3.11 | 4.17 | 9.38 | 10.91 |
| 3.96 | 2.5 | 4.52 | 4.29 | 6.44 | 12.31 | 14.04 |
| 7.16 | 5.03 | 8.63 | 8.41 | 12.92 | 19.98 | 22.31 |
| 7.89 | 5.6 | 9.58 | 9.44 | 14.43 | 21.54 | 24.13 |

EXAMPLE 14

Accelerated Yellowing with High Intensity Lamps

BTMP sheets are treated with 0.25% by weight of Compounds B, T, U and V and 0.5% by weight of the benzophenone UVA compounds:

(2-hydroxy-4-octyloxy-phenyl)-phenyl-methanone;

(2-hydroxy-4-methoxy-phenyl)-phenyl-methanone;

(4-dodecyloxy-2-hydroxy-phenyl)-phenyl-methanone;

(2-hydroxy-4-methoxy-phenyl)-(2-hydroxy-phenyl)-methanone;

bis-(2-hydroxy-4-methoxy-phenyl)-methanone;

bis-(2,4-dihydroxy-phenyl)-methanone;

[3-(3-benzoyl-2-hydroxy-6-methoxy-benzyl)-2-hydroxy-4-methoxy-phenyl]-phenyl-methanone;

2-hydroxy-4-methoxybenzophenone-5-sulfonic acid;

2,2'-dihydroxy-4,4'-dimethoxybenzophenone-5,5'-disodium sulfonate.

The sheets treated with a combination of nitroxide and UVA exhibit substantial inhibition to yellowing compared to the untreated control sheet and illustrate the performance enhancement when combinations of nitroxide and UVA are used.

EXAMPLE 15

Accelerated Yellowing with High Intensity Lamps

BTMP sheets are treated with 0.25% by weight of Compounds B, T, U and V and 0.5% by weight of the UVA compounds:

(a) 5-chloro-2-(2-hydroxy-3,5-di-tert-butylphenyl)-2H-benzotriazole;

(b) 2-(2-hydroxy-3,5-di-tert-butylphenyl)-2H-benzotriazole;

(c) 2-(2-hydroxy-3,5-di-tert-amylphenyl)-2H-benzotriazole;

(d) 2-(2-hydroxy-3,5-di-α-cumylphenyl)-2H-benzotriazole;

(e) 2-(2-hydroxy-3-α-cumyl-5-tert-octylphenyl)-2H-benzotriazole;

(f) 2-(2-hydroxy-5-tert-octylphenyl)-2H-benzotriazole;

(g) 3-(2H-benzotriazol-2-yl)-4-hydroxy-5-(1-methylpropyl)-benzenesulfonic acid monosodium salt;

(h) 3-tert-butyl-4-hydroxy-5-(2H-benzotriazol-2-yl)-hydrocinnamic acid and sodium salt;
(i) 12-hydroxy-3,6,9-trioxadodecyl 3-tert-butyl-4-hydroxy-5-(2H-benzotriazol-2-yl)-hydrocinnamate;
(j) octyl 3-tert-butyl-4-hydroxy-5-(2H-benzotriazol-2-yl)-hydrocinnamate;
(k) 4,6-bis(2,4-dimethylphenyl)-2-(4-(3-dodecyloxy*-2-hydroxypropoxy)-2-hydroxy phenyl)-s-triazine (*is mixture of $C_{12-14}$oxy isomers);
(l) 4,6-bis(2,4-dimethylphenyl)-2-(4-octyloxy-2-hydroxyphenyl)-s-triazine;
(m) 2,4-dihydroxybenzophenone;
(n) 2,2',4,4'-tetrahydroxy-5,5'-disulfobenzophenone, disodium salt;
(o) 2-hydroxy-4-octyloxybenzophenone;
(p) 2-hydroxy-4-dodecyloxybenzophenone;
(q) 2,4-dihydroxybenzophenone;
(r) 2,2',4,4'-tetrahydroxybenzophenone;
(s) 4-aminobenzoic acid;
(t) 2,3-dihydroxypropyl-4-aminobenzoic acid;
(u) 3-(4-imidazolyl)acrylic acid;
(v) 2-phenyl-5-benzimidazole sulfonic acid;
(w) N,N,N-trimethyl-α-(2-oxo-3-bornylidene)-p-toluidinium methyl sulfate;
(x) 5-benzoyl-4-hydroxy-2-methoxybenzenesulfonic acid, sodium salt;
(y) 3-(4-benzoyl-3-hydroxyphenoxy)-2-hydroxy-N,N,N-trimethyl-1-propanaminium chloride;
(z) 3-[4-(2H- benzotriazol-2-yl)-3-hydroxyphenoxy]-2-hydroxy-N,N,N-trimethyl-1-propanaminium, chloride;
(aa) 2-(2-hydroxy-5-methylphenyl)-2H-benzotriazole.

The sheets treated with a combination of nitroxide and UVA exhibit substantial inhibition to yellowing compared to the untreated control sheet and illustrate the performance enhancement when combinations of nitroxide and UVA are used.

EXAMPLE 16

Accelerated Yellowing with High Intensity Lamps

BTMP sheets are treated with 0.25% by weight of Compounds B, T, U and V and 0.5% by weight of the triazine UVA compounds:

4,6-bis(2,4-dimethylphenyl)-2-(4-(3-dodecyloxy*-2-hydroxypropoxy)-2-hydroxyphenyl)-s-triazine (*mixture of $C_{12-14}$oxy isomers) (Tinuvin 400);

4,6-bis(2,4-dimethylphenyl)-2-(2-hydroxy-4-octyloxyphenyl)-s-triazine;

2,4,6-tris(4-(3-dodecyloxy*-2-hydroxypropoxy)-2-hydroxyphenyl)-s-triazine (*mixture of $C_{12-14}$oxy isomers);

2,4-bis(4-(3-dodecyloxy*-2-hydroxypropoxy)-2-hydroxyphenyl)-6-(2,4-dimethylphenyl)-s-triazine (*mixture of $C_{12-14}$oxy isomers).

The sheets treated with a combination of nitroxide and UVA exhibit substantial inhibition to yellowing compared to the untreated control sheet and illustrate the performance enhancement when combinations of nitroxide and UVA are used.

EXAMPLE 17

Accelerated Yellowing with High Intensity Lamps

BTMP sheets are treated with 0.25% by weight of Compounds B, T, U and V and 0.5% by weight of the cinnamate UVA compounds:

2-cyano-3,3-diphenyl-2-propenoic acid ethyl ester;
2-cyano-3,3-diphenyl-2-propenoic acid 2-ethylhexyl ester;
3-(4-methoxyphenyl)-2-propenoic acid 2-ethylhexyl ester.

The sheets treated with a combination of nitroxide and UVA exhibit substantial inhibition to yellowing compared to the untreated control sheet and illustrate the performance enhancement when combinations of nitroxide and UVA are used

EXAMPLE 18

Accelerated Yellowing with High Intensity Lamps

BTMP sheets are treated with 0.25% by weight of Compounds B, T, U and V and 0.5% by weight of the oxalanilide UVA compounds:

N-(2-ethoxyphenyl)-N'-(4-isododecylphenyl)-ethanediamide;

N-(2-ethoxyphenyl)-N'-(2-ethylphenyl)-ethanediamide.

The sheets treated with a combination of nitroxide and UVA exhibit substantial inhibition to yellowing compared to the untreated control sheet and illustrate the performance enhancement when combinations of nitroxide and UVA are used.

EXAMPLE 19

Accelerated Yellowing with High Intensity Lamps

BTMP sheets are treated with 0.25% by weight of Compounds B, T, U and V and 0.5% by weight of the salicylate UVA compounds:

2-hydroxy-benzoic acid phenyl ester;
2-hydroxy-benzoic acid 4-(1,1-dimethylethyl)phenyl ester;
2-hydroxy-benzoic acid 2-ethylhexyl ester;
2-hydroxy-benzoic acid 4-isopropylbenzyl ester;
2-hydroxy-benzoic acid 3,3,5-trimethylcyclohexyl ester.

The sheets treated with a combination of nitroxide and UVA exhibit substantial inhibition to yellowing compared to the untreated control sheet and illustrate the performance enhancement when combinations of nitroxide and UVA are used.

EXAMPLE 20

Accelerated Yellowing with High Intensity Lamps

BTMP sheets are treated with 0.25% by weight of Compounds B, T, U and V and 0.5% by weight of the formamidine UVA compounds:

4-[[(methylphenylamino)methylene]amino]-benzoic acid, ethyl ester;

4-[[(ethylphenylamino)methylene]amino]-benzoic acid, ethyl ester.

The sheets treated with a combination of nitroxide and UVA exhibit substantial inhibition to yellowing compared to the untreated control sheet and illustrate the performance enhancement when combinations of nitroxide and UVA are used.

EXAMPLE 21

Accelerated Yellowing with High Intensity Lamps

BTMP sheets are treated with 0.25% by weight of Compounds B, T, U and V and 0.5% by weight of the 4-hydroxybenzoate UVA compounds:

3,5-bis(1,1-dimethylethyl)-4-hydroxy-benzoic acid hexadecyl ester;

3,5-bis(1,1-dimethylethyl)-4-hydroxy-benzoic acid 2,4-bis(1,1-dimethylethyl)phenyl ester.

The sheets treated with a combination of nitroxide and UVA exhibit substantial inhibition to yellowing compared to the untreated control sheet and illustrate the performance enhancement when combinations of nitroxide and UVA are used.

EXAMPLE 22

Accelerated Yellowing with High Intensity Lamps

BTMP sheets are treated with 0.25% by weight of Compounds B, T, U and V and 0.5% by weight of the 4-aminobenzoate UVA compounds:

4-aminobenzoic acid;

2,3-dihydroxypropyl-4-aminobenzoate;

2-ethylhexyl 4-dimethylaminobenzoate;

ethyl 4-[bis(2-hydroxypropyl)amino]benzoate.

The sheets treated with a combination of nitroxide and UVA exhibit substantial inhibition to yellowing compared to the untreated control sheet and illustrate the performance enhancement when combinations of nitroxide and UVA are used.

EXAMPLE 23

Accelerated Yellowing with High Intensity Lamps

BTMP sheets are treated with 0.50% by weight of Compounds A, F, G, H, I and J and 0.5% of Compound R. The sheets treated with hydroxylamine salts and UVA exhibit substantial inhibition to yellowing compared to the untreated control sheet.

| Time in Days | 0.5% G 0.5% R | 0.5% H 0.5% R | 0.5% F 0.5% R | 0.5% I 0.5% R | 0.5% J 0.5% R | 0.5% A 0.5% R | Blank |
|---|---|---|---|---|---|---|---|
| | | | PC Number | | | | |
| 0 | 0 | 0 | 0 | 0 | 0 | 0 | 0 |
| 0.76 | 0.57 | −0.14 | 0.06 | 0.16 | −0.18 | −0.55 | 3.51 |
| 1.85 | 0.96 | 0.02 | 0.32 | 0.33 | 0 | −0.49 | 6.43 |
| 2.81 | 1.55 | 0.17 | 0.63 | 0.57 | 0.25 | −0.33 | 8.77 |
| 3.76 | 1.94 | 0.38 | 0.9 | 0.81 | 0.48 | −0.21 | 10.89 |
| 4.82 | 2.52 | 0.57 | 1.24 | 1.01 | 0.66 | −0.06 | 12.99 |
| 5.8 | 2.89 | 0.68 | 1.49 | 1.17 | 0.87 | 0.05 | 14.7 |
| 6.82 | 3.27 | 0.81 | 1.64 | 1.38 | 1.06 | 0.14 | 16.03 |
| 7.77 | 3.84 | 1.05 | 2 | 1.59 | 1.29 | 0.3 | 17.33 |
| 8.76 | 4.05 | 1.16 | 2.17 | 1.75 | 1.42 | 0.43 | 18.22 |
| 9.81 | 4.77 | 1.38 | 2.46 | 1.98 | 1.67 | 0.57 | 19.27 |
| 10.88 | 5.11 | 1.53 | 2.69 | 2.27 | 1.86 | 0.69 | 20.18 |
| 11.82 | 5.51 | 1.7 | 2.97 | 2.45 | 2.08 | 0.84 | 21.03 |
| 12.78 | 5.77 | 1.89 | 3.13 | 2.7 | 2.25 | 0.92 | 22.03 |

EXAMPLE 24

Accelerated Yellowing with High Intensity Lamps

BTMP sheets are treated with 0.50% by weight of Compounds K and L and 0.5% by weight of Compound S. The sheets treated with Compounds K and L and a UVA exhibit substantial inhibition to yellowing compared to the untreated control sheet.

| Time in Days | 0.5% K 0.5% S | 0.5% L 0.5% S PC Number | 0.5% S | Blank |
|---|---|---|---|---|
| 0 | 0 | 0 | 0 | 0 |
| 0.81 | 0 | 0.04 | 0.29 | 3.03 |
| 1.82 | 0.51 | 0.87 | 0.89 | 5.78 |
| 2.8 | 1.08 | 1.1 | 1.47 | 8.11 |
| 3.75 | 1.56 | 1.65 | 2.14 | 10.21 |
| 4.83 | 2.04 | 2.25 | 2.83 | 12.33 |
| 5.8 | 2.64 | 2.76 | 3.56 | 14.13 |
| 6.76 | 2.98 | 3.23 | 4.18 | 15.6 |
| 7.77 | 3.54 | 3.82 | 4.93 | 17.45 |
| 8.74 | 3.97 | 4.45 | 5.7 | 18.98 |
| 9.75 | 4.6 | 5.18 | 6.5 | 30.34 |
| 10.74 | 5.07 | 5.85 | 7.39 | 21.91 |

EXAMPLE 25

Accelerated Yellowing with High Intensity Lamps

BTMP sheets are treated with 0.50% by weight of Compounds M, N and O and 0.5% by weight of the UVA Compound W. The sheets treated with selected hydroxylamine derivatives and the UVA exhibit substantial inhibition to yellowing compared to the untreated control sheet.

| Time in Days | 0.5% M 0.5% W | 0.5% N 0.5% W | 0.5% O 0.5% W | 0.5% W | Blank |
|---|---|---|---|---|---|
| | | | PC Number | | |
| 0 | 0 | 0 | 0 | 0 | 0 |
| .82 | 0.59 | 0.46 | 0.51 | .79 | 3.87 |
| 2.72 | 1.84 | 1.46 | 1.77 | 2.25 | 8.9 |
| 3.76 | 2.43 | 1.91 | 2.46 | 2.90 | 10.88 |
| 4.76 | 3.09 | 2.34 | 3.12 | 3.52 | 12.59 |
| 5.76 | 3.84 | 2.9 | 3.87 | 4.32 | 14.32 |
| 6.77 | 4.75 | 3.59 | 4.72 | 5.12 | 16.36 |
| 7.81 | 5.7 | 4.37 | 5.68 | 6.09 | 18.47 |
| 8.79 | 6.55 | 4.98 | 6.46 | 6.86 | 20.15 |
| 10.0 | 7.43 | 5.45 | 7.37 | 7.7 | 21.9 |
| 10.77 | 8.28 | 6.19 | 8.28 | 8.64 | 23.5 |

EXAMPLE 26

Accelerated Yellowing with High Intensity Lamps

BTMP sheets are treated with 0.50% by weight of Compound P and 0.5% Compound S. The sheets treated with Compound P in combination with a UVA exhibit substantial inhibition to yellowing compared to the untreated control sheet.

| Time in Days | 0.5% P 0.5% S | 0.5% S | Blank |
|---|---|---|---|
| | PC Number | | |
| 0 | 0 | 0 | 0 |
| 0.81 | 0.06 | 0.29 | 3.03 |
| 1.82 | 0.46 | 0.89 | 5.78 |
| 2.8 | 0.95 | 1.47 | 8.11 |
| 3.75 | 1.37 | 2.14 | 10.21 |
| 4.83 | 1.74 | 2.53 | 12.33 |
| 5.8 | 2.13 | 3.56 | 14.13 |
| 6.76 | 2.5 | 4.18 | 15.6 |

-continued

| Time in Days | 0.5% P 0.5% S | 0.5% S | Blank |
|---|---|---|---|
| 7.77 | 2.95 | 4.93 | 17.45 |
| 8.74 | 3.42 | 5.7 | 18.98 |

EXAMPLE 27

Accelerated Yellowing with High Intensity Lamps

BTMP sheets are treated with and 0.5% Compound S and 0.5% by weight of:

1-acetyl-4-hydroxy-2,2,6,6-tetramethyl-piperidine;
1-acetyl-2,2,6,6-tetramethyl-piperidin-4-one;
bis(1-acetyl-2,2,6,6-tetramethylpiperidin-4-yl)sebacate.

The sheets treated with acylated hindered amine derivatives in combination with a UVA exhibit substantial inhibition to yellowing compared to the untreated control sheet.

EXAMPLE 28

Accelerated Yellowing with High Intensity Lamps

BTMP sheets are treated with 0.25% by weight of Compound A, 0.5% Compound W and 0.5% of Compound X. The sheets treated with hydroxylamine, UVA and PEO exhibit substantial inhibition to yellowing compared to the untreated control sheet.

| Time in Days | 0.25% A | 0.25% A 0.5% W | 0.25% A 0.5% W 0.5% X | Blank |
|---|---|---|---|---|
| | | PC Number | | |
| 0 | 0 | 0 | 0 | 0 |
| 0.77 | 0.97 | 0.06 | 0.03 | 3.74 |
| 1.85 | 1.86 | 0.28 | 0.27 | 7.25 |
| 2.78 | 2.85 | 0.49 | 0.46 | 10.43 |
| 5.84 | 6.42 | 1.54 | 1.48 | 19.5 |
| 6.93 | 7.85 | 2 | 1.98 | 21.69 |
| 5 | 8.82 | 2.34 | 2.26 | 23.25 |

EXAMPLE 29

Accelerated Yellowing with High Intensity Lamps

BTMP sheets are treated with 0.25% by weight of Compound A, 0.5% Compound Y, Z and M and 0.5% of Compound X. The sheets treated with hydroxylamine, UVA and PEO exhibit substantial inhibition to yellowing compared to the untreated control sheet.

| Time in Days | 0.25% A | 0.25% A 0.5% Y | 0.25% A 0.5% Y 0.5% X | 0.25% A 0.5% Z | 0.25% A 0.5% Z 0.5% X | 0.25% A 0.5% AA | 0.25% A 0.5% AA 0.5% X | Blank |
|---|---|---|---|---|---|---|---|---|
| | | | PC Number | | | | | |
| 0 | 0 | 0 | 0 | 0 | 0 | 0 | 0 | 0 |
| 0.84 | 1.22 | 0.34 | 0.27 | 1.11 | 1.09 | 0.33 | 0.22 | 4 |
| 1.77 | 1.94 | 0.64 | 0.45 | 1.32 | 1.54 | 0.53 | 0.43 | 7.73 |
| 4.88 | 5.48 | 2.41 | 1.86 | 3.87 | 4.9 | 2.39 | 1.67 | 18.19 |
| 5.92 | 6.9 | 3.11 | 2.46 | 4.82 | 5.82 | 3.01 | 2.09 | 21.03 |
| 6.99 | 7.64 | 3.64 | 2.81 | 5.34 | 6.51 | 3.48 | 2.41 | 22.93 |

EXAMPLE 30

Accelerated Yellowing with High Intensity Lamps

BTMP sheets are treated with 0.5% by weight of Compound G, 0.25% by weight of Compound W and 0.25% by weight of Compound BB. The sheets treated with hydroxylamine, UVA and metal chelating agent exhibit substantial inhibition to yellowing compared to the untreated control sheet.

| Time in Days | 0.5% G 0.25% W 0.25% BB | 0.5% G 0.25% BB | 0.5% G 0.25% W | 0.5% G | 0.25% BB | Blank |
|---|---|---|---|---|---|---|
| | | | PC Number | | | |
| 0 | 0 | 0 | 0 | 0 | 0 | 0 |
| 0.83 | 0.13 | 0.69 | 0.23 | 0.76 | 3.6 | 3.68 |
| 1.79 | 0.37 | 1.26 | 0.48 | 1.33 | 6.17 | 6.19 |
| 2.77 | 0.58 | 1.82 | 0.72 | 1.87 | 8.41 | 8.45 |
| 3.81 | 0.84 | 2.44 | 1.01 | 2.46 | 10.48 | 10.49 |
| 4.9 | 1.14 | 3.02 | 1.35 | 2.99 | 12.36 | 12.19 |
| 5.83 | 1.37 | 3.53 | 1.62 | 3.51 | 14.05 | 13.82 |
| 6.8 | 1.62 | 4.1 | 1.87 | 4.07 | 15.82 | 15.39 |
| 7.77 | 1.93 | 4.67 | 2.23 | 4.69 | 17.31 | 16.59 |

EXAMPLE 31

Accelerated Yellowing with High Intensity Lamps

BTMP sheets are treated with 0.25% by weight of Compound B, 0.5% by weight of Compound Q and 1.0% by weight of Compound CC or DD. The results show the effectiveness of nitrones alone, nitrones with a UVA, nitrones with a nitroxide and especially nitrone with a UVA and a nitroxide in inhibition to yellowing compared to the untreated control sheet.

| Time in Days | 0.5% Q 0.25% B 1% CC | 0.5% Q 0.25% B 1% DD | 0.5% Q 1% CC | 0.5% Q 1% DD | 0.5% Q | 0.25% B 1% CC | 0.25% B 1% DD | 1% CC | 1% DD | Blank |
|---|---|---|---|---|---|---|---|---|---|---|
| | | | | | PC Number | | | | | |
| 0 | 0 | 0 | 0 | 0 | 0 | 0 | 0 | 0 | 0 | 0 |
| 0.74 | −1.25 | 0.13 | −0.43 | 0.25 | 0.55 | −0.43 | 0.85 | 0.28 | 2.14 | 3.22 |
| 1.74 | −0.92 | 0.45 | −0.16 | 0.72 | 1.19 | 0.28 | 2.49 | 1.82 | 4.78 | 7.24 |
| 2.82 | −0.59 | 0.84 | 0.25 | 1.26 | 1.82 | 0.83 | 3.83 | 3.69 | 6.68 | 9.77 |
| 3.83 | −0.41 | 1.33 | 0.93 | 1.86 | 2.63 | 1.63 | 5.09 | 5.88 | 8.34 | 12.42 |
| 4.76 | −0.19 | 1.75 | 1.7 | 2.56 | 3.53 | 2.53 | 6.13 | 7.8 | 9.8 | 14.78 |
| 5.75 | −0.01 | 2.08 | 2.54 | 3.13 | 4.41 | 3.3 | 6.87 | 9.63 | 11.14 | 16.89 |
| 6.77 | 0.19 | 2.51 | 3.35 | 3.77 | 5.36 | 3.96 | 7.67 | 11.25 | 12.33 | 19.13 |
| 7.75 | 0.44 | 2.91 | 4.14 | 4.36 | 6.13 | 4.56 | 8.23 | 12.39 | 13.16 | 20.09 |
| 8.77 | 0.63 | 3.22 | 5.07 | 4.87 | 6.94 | 5.27 | 8.84 | 13.87 | 14 | 21.84 |

EXAMPLE 32

Accelerated Yellowing with High Intensity Lamps

BTMP sheets are treated with 0.5% by weight of Compound Q and 0.25% by weight of Compounds D, B, C, E and A. The results show the superiority of hydroxylamines over nitroxides in maintaining a high brightness of the paper upon application and during exposure.

| Time in Days | 0.5% Q 0.25% D | 0.5% Q 0.25% B | 0.5% Q 0.25% C | 0.5% Q 0.25% E | 0.5% Q 0.25% A | 0.5% Q | Blank |
|---|---|---|---|---|---|---|---|
| | | | ISO Brightness | | | | |
| 0 | 78.83 | 76.96 | 76.75 | 78.24 | 79.85 | 79.75 | 78.6 |
| 0.75 | 77.45 | 77.53 | 77.15 | 76.21 | 78.91 | 75.36 | 68.43 |
| 1.74 | 75.77 | 77.16 | 76.66 | 74.36 | 78.48 | 72.22 | 62.89 |
| 2.74 | 73.61 | 76.59 | 75.89 | 72.1 | 77.7 | 68.93 | 58.54 |
| 3.75 | 71.95 | 75.96 | 75.21 | 70.14 | 77.12 | 66.09 | 55.41 |
| 6.81 | 65.96 | 72.86 | 72.02 | 64.11 | 74.09 | 58.58 | 49.29 |

EXAMPLE 33

Accelerated Yellowing with High Intensity Lamps

Additives are added with a sizing treatment on 100% BTMP paper coated with 2 g/m$^2$/side using a Pilot Liquid Application System from Bonnier Technology Group Inc. (LAS System). It consists of a hydrophilic roll, soft metering roll, soft backing roll, and sizing pan. A film of sizing solution is drawn through the metering nip onto the hydrophilic roll. The paper gets sized when it runs between the hydrophilic roll and the backing roll.

Starch Based Coating Formulation:

| Commercial name | Chemical Nature | Parts |
|---|---|---|
| Penford ® Gum 280 | Hydroxyethylated starch | 80 |
| Acronal ® S728 | N-Butylacrylate & styrene copolymer dispersion | 20 |

| Time in Days | Blank | Sizing only | Sizing 0.36% G 0.84% S | Sizing 0.24% G 0.55% S |
|---|---|---|---|---|
| | | PC Number | | |
| 0 | 0 | 0 | 0 | 0 |
| 1.01 | 4.69 | 4.45 | 0.59 | 0.95 |

-continued

| | | | | |
|---|---|---|---|---|
| 1.85 | 6.78 | 6.51 | 0.79 | 1.53 |
| 2.9 | 8.95 | 8.98 | 1.04 | 1.91 |
| 4.1 | 11.61 | 10.68 | 1.41 | 2.51 |
| 4.8 | 13.29 | 12.12 | 1.66 | 2.84 |
| 5.81 | 14.75 | 13.98 | 1.89 | 3.23 |

-continued

| | | | | |
|---|---|---|---|---|
| 6.77 | 16.1& | 15.26 | 2.04 | 3.66 |
| 7.82 | 17.16 | 16.27 | 2.42 | 3.85 |
| 8.78 | 18.17 | 17.19 | 2.45 | 4.22 |
| 9.89 | 19.28 | 18.19 | 2.66 | 4.42 |
| 10.92 | 21.11 | 19.45 | 3.02 | 4.97 |
| 11.81 | 20.8 | 20.31 | 3.18 | 5.37 |
| 12.81 | 21.98 | 21.18 | 3.55 | 5.58 |
| 13.79 | 22.68 | 22.16 | 3.65 | 5.99 |

Total solids content of 20%, pH around 7.0

EXAMPLE 34

Accelerated Yellowing with High Intensity Lamps

Additives are added with a pigmented sizing treatment on 100% BTMP paper coated with 2 g/m$^2$/side using a Pilot Liquid Application System from Bonnier Technology Group Inc. (LAS System). It consists of a hydrophilic roll, soft metering roll, soft backing roll, and sizing pan. A film of sizing solution is drawn through the metering nip onto the hydrophilic roll. The paper gets sized when it runs between the hydrophilic roll and the backing roll.

100% BTMP paper coated with 4 g/m$^2$/side pigments based coating formulation:

| Commercial name | Chemical Nature | Parts |
|---|---|---|
| Covercarb ® | Ultrafine ground calcium carbonate | 80 |
| Astraplate ® | Delaminated clay | 20 |
| Penford ® Gum 280 | Hydroxyethylated starch | 6 |
| Acronal ® S728 | N-Butylacrylate & styrene copolymer dispersion | 12 |
| Sterocoll ® AL | Anionic water-in-oil emulsion of an acrylamide-acrylic copolymer | 0.1 |
| AZCOTE ® 5800M | Ammonium zirconium carbonate solution | 0.5 |

Total solids content of 57%, pH around 8.0

| Time in Days | Blank | Coating only | Coating 0.13% G 0.4% S | Coating 0.4% G 0.74% S | Coating 0.19% G 0.48% S |
|---|---|---|---|---|---|
| | | | PC Number | | |
| 0 | 0 | 0 | 0 | 0 | 0 |
| 1 | 4.46 | 3.66 | 0.65 | 0.16 | 0.7 |
| 1.83 | 7.16 | 5.15 | 1.03 | 0.31 | 1.15 |
| 2.91 | 8.54 | 6.7 | 1.21 | 0.43 | 1.41 |
| 4.11 | 11.04 | 8.47 | 1.53 | 0.59 | 1.61 |
| 4.8 | 13.08 | 10.55 | 2.1 | 0.59 | 1.96 |
| 5.82 | 14.25 | 11.19 | 2.02 | 0.8 | 2.16 |
| 6.78 | 16.01 | 12.44 | 2.39 | 0.92 | 2.54 |
| 7.83 | 17.45 | 13.67 | 2.61 | 1.02 | 2.7 |
| 8.8 | 18.09 | 14.08 | 2.68 | 0.98 | 2.86 |
| 9.9 | 18.9 | 14.88 | 2.95 | 1.09 | 3.02 |
| 10.94 | 20.19 | 15.67 | 3.12 | 1.21 | 3.28 |
| 11.81 | 21.38 | 16.68 | 3.59 | 1.31 | 3.57 |
| 12.82 | 22.25 | 17.57 | 3.58 | 1.46 | 3.75 |
| 13.8 | 23.26 | 18.21 | 3.83 | 1.59 | 4.27 |

EXAMPLE 35

Using the accelerated test method, BTMP handsheets containing various combinations of 0.25% by weight of a hindered amine, 0.5% by weight of an s-triazine UV absorber and/or 0.5% by weight of a polymeric additives are compared for efficacy in preventing yellowing. The data are presented on the table below.

Table for Example 35

| Square Names Days | A | B | C | D | E | F | G | H | I | J | K |
|---|---|---|---|---|---|---|---|---|---|---|---|
| | | | | | | PC Numbers | | | | | |
| 1.14 | 2.56 | 1.937 | 2.557 | .1627 | .2688 | .6753 | 2.754 | 1.833 | 2.188 | 1.927 | 5.319 |
| 1.97 | 4.40 | 3.214 | 4.042 | .4481 | .5323 | 1.249 | 4.484 | 2.987 | 3.643 | 3.219 | 8.064 |
| 2.98 | 6.20 | 4.546 | 5.752 | .7997 | .9261 | 1.873 | 6.326 | 4.360 | 5.338 | 4.778 | 10.99 |
| 4.06 | 9.04 | 6.210 | 7.590 | 1.287 | 1.460 | 2.742 | 8.403 | 5.855 | 6.964 | 6.352 | 13.95 |
| 5.03 | 11.50 | 8.252 | 9.841 | 2.087 | 2.228 | 3.957 | 10.64 | 7.498 | 9.008 | 8.229 | 17.20 |
| 5.98 | 12.74 | 9.404 | 11.19 | 2.466 | 2.582 | 4.593 | 12.16 | 8.572 | 10.13 | 9.295 | 19.28 |
| 6.96 | 14.25 | 10.54 | 12.58 | 2.747 | 2.889 | 5.203 | 13.25 | 9.360 | 11.04 | 10.18 | 21.01 |
| 7.98 | 16.48 | 12.23 | 14.65 | 3.541 | 3.792 | 6.425 | 15.24 | 11.07 | 12.66 | 11.74 | 23.52 |

A contains the UV absorber TINUVIN ® 400; Compound Y.
B contains the UV absorber TINUVIN ® 400 and the polymer PEO.
C contains the UV absorber TINUVIN ® 400 and the polymer PTHF.
D contains the hindered amine nitroxide Compound B, the UV absorber TINUVIN ® 400 and the polymer PEO.
E contains the hindered amine nitroxide Compound B, the UV absorber TINUVIN ® 400 and the polymer PTHF.
F contains the hindered amine nitroxide Compound B and the UV absorber TINUVIN ®0 400.
G contains the hindered amine nitroxide Compound JJ and the UV absorber TINUVIN ® 400.
H contains the hindered amine nitroxide Compound B.
I contains the hindered amine TEMPO.
J contains the hindered amine TEMPO.
K is the control containing no stabilizer additives.

As inspection of the data on the table attests, in best to poorest order D≅E>F>H>J>B>I>C>G>A>>K. These data show that the combination of a nitroxide, a UV absorber and a polymer coadditive provides the best protection against yellowing after 8 days exposure.

EXAMPLE 36

Using the accelerated test method, BTMP handsheets containing various combinations of 0.25% by weight of a hindered amine, 0.5% by weight of a benzophenone UV absorber and/or 0.5% by weight of a polymeric additives are compared for efficacy in preventing yellowing. The data are presented on the table below.

Table for Example 36

| Square Names Days | A | B | C | D | E | F | G | H | I |
|---|---|---|---|---|---|---|---|---|---|
| | | | | | PC Numbers | | | | |
| .822 | 1.89 | 1.545 | 1.784 | .0633 | .0881 | .0211 | 1.574 | .9791 | 3.826 |
| 1.87 | 3.41 | 2.733 | 3.241 | .3018 | .2650 | .1786 | 2.911 | 2.048 | 6.978 |
| 2.91 | 5.00 | 4.254 | 4.939 | .6705 | .5656 | .4648 | 4.489 | 3.249 | 10.19 |
| 3.87 | 6.96 | 6.038 | 6.875 | 1.371 | 1.183 | 1.100 | 6.319 | 4.770 | 13.68 |
| 4.83 | 8.59 | 7.534 | 8.702 | 1.808 | 1.484 | 1.334 | 7.759 | 5.903 | 16.43 |
| 5.81 | 9.93 | 8.690 | 9.944 | 2.031 | 1.658 | 1.483 | 8.810 | 6.785 | 18.26 |
| 6.83 | 11.80 | 10.37 | 11.67 | 2.704 | 2.217 | 2.079 | 10.34 | 7.968 | 21.39 |
| 7.82 | 13.59 | 11.99 | 13.49 | 3.288 | 2.653 | 2.559 | 11.53 | 9.169 | 23.91 |

A contains the UV absorber UVINUL ® 3000.
B contains the UV absorber UVINUL ® 3000 and the polymer PEO.
C contains the UV absorber UVINUL ® 3000 and the polymer PTHF.
D contains the hindered amine nitroxide Compound B, the UV absorber UVINUL ® 3000 and the polymer PEO.
E contains the hindered amine nitroxide Compound B, the UV absorber UVINUL ® 3000 and the polymer PTHF.
F contains the hindered amine nitroxide Compound B and the UV absorber UVINUL ® 3000.
G contains the hindered amine Compound JJ and the UV absorber UVINUL ® 3000.
H contains the hindered amine nitroxide Compound B.
J is the control containing no stabilizer additives.

As inspection of the data on the table attests, in best to poorest order F>E>D>H>G>B>C≅A>>I. These data show that the combination of a nitroxide and a benzophenone UV absorber coadditive provides the best protection against yellowing after 8 days exposure.

EXAMPLE 37

Using the accelerated test method, BTMP handsheets containing various combinations of 0.25% by weight of a hindered amine, 0.5% by weight of a benzophenone UV absorber and/or 0.5% by weight of a polymeric additives are compared for efficacy in preventing yellowing. The data are presented on the table below.

Table for Example 37

| Square Names Days | A | B | C | D | E | F | G |
|---|---|---|---|---|---|---|---|
| | | | | PC Numbers | | | |
| 1.01 | 3.60 | 3.621 | 1.383 | 1.764 | 3.454 | 1.221 | 5.048 |
| 2.09 | 6.42 | 6.027 | 2.412 | 3.200 | 5.842 | 2.501 | 8.506 |
| 3.05 | 9.03 | 8.646 | 3.845 | 5.012 | 8.433 | 4.123 | 12.04 |
| 4.01 | 11.60 | 11.21 | 4.957 | 6.360 | 10.54 | 5.245 | 15.26 |
| 4.98 | 13.19 | 13.01 | 4.412 | 7.396 | 11.92 | 6.115 | 17.50 |
| 6.01 | 15.49 | 15.26 | 6.252 | 9.151 | 14.34 | 7.611 | 20.59 |
| 7.00 | 17.75 | 17.67 | 7.653 | 10.83 | 16.64 | 8.926 | 23.32 |

A contains the UV absorber UVINUL ® 3048; Compound Z.
B contains the UV absorber UVINUL ® 3048 and the polymer PEO.
C contains the hindered amine nitroxide Compound F, the UV absorber UVINUL ® 3048 and the polymer PEO.
D contains the hindered amine nitroxide Compound B and the UV absorber UVINUL ® 3048.
E contains the hindered amine Compound JJ and the UV absorber UVINUL ® 3048.
F contains the hindered amine nitroxide Compound B.
G is the control containing no stabilizer additives.

As inspection of the data on the table attests, in best to poorest order C>F>D>E>B≅A>>G. These data show that the combination of a nitroxide, a benzophenone UV absorber and polymer coadditive provides the best protection against yellowing after 7 days exposure.

The tables in Examples 38 to 48 all show PC Numbers.

EXAMPLE 38

Using the accelerated test method, BTMP handsheets containing various combinations of 1% by weight of a hindered amine, 0.5% by weight of a benzotriazole UV absorber and/or 0.5% by weight of a polymeric additives are compared for efficacy in preventing yellowing. The data are presented on the table below.

Table for Example 38

| Days | A | B | C | D | E | F | G | H |
|---|---|---|---|---|---|---|---|---|
| 0 | 0 | 0 | 0 | 0 | 0 | 0 | 0 | 0 |
| 1.17 | 1.62 | 0.91 | 1.13 | 1.4 | 2.26 | 2.85 | 3.35 | 3.42 |
| 2 | 3 | 1.81 | 2.18 | 2.24 | 3.69 | 4.42 | 5.07 | 5.26 |
| 2.98 | 4.23 | 2.62 | 3.15 | 3.14 | 5.21 | 5.9 | 6.75 | 7.22 |
| 4 | 5.67 | 3.58 | 4.32 | 4.44 | 7.26 | 7.81 | 9.09 | 9.87 |
| 5.01 | 6.73 | 4.28 | 5.2 | 5.13 | 8.84 | 9.08 | 10.48 | 11.72 |
| 5.99 | 7.73 | 5.01 | 5.98 | 6.08 | 10.64 | 10.49 | 12.11 | 13.69 |
| 6.94 | 8.75 | 5.74 | 6.79 | 6.75 | 11.91 | 11.42 | 13.29 | 14.95 |
| 7.98 | 9.62 | 6.46 | 7.55 | 7.48 | 13.25 | 12.44 | 14.36 | 16.48 |
| 8.99 | 10.27 | 6.99 | 8.14 | 8.2 | 14.63 | 13.54 | 15.66 | 18.25 |
| 9.98 | 10.6 | 7.36 | 8.56 | 9.03 | 16.1 | 14.56 | 16.81 | 19.97 |
| 11.01 | 11.34 | 7.96 | 9.27 | 9.93 | 17.85 | 15.9 | 18.37 | 21.84 |
| 12.01 | 13.48 | 9.17 | 10.27 | 10.57 | 19.04 | 16.65 | 19.19 | 23.03 |

A contains the hindered amine TMHP, the UV absorber TINUVIN ® 1130 and the polymer PEO.
B contains the hindered amine TMHP, the UV absorber TINUVIN ® 1130 and the polymer PTHF.
C contains the hindered amine TMHP and the UV absorber TINUVIN ® 1130.
D contains the hindered amine Compound G and the UV absorber TINUVIN ® 1130.
E contains the UV absorber TINUVIN ® 1130.
F contains the hindered amine TMHP.
G contains the hindered amine Compound JJ.
H is the control containing no stabilizer additives.

As inspection of the data on the table attests, in best to poorest order D>B>C>F>A>E>G>H. These data show that the combination of a hindered amine and a benzotrizole UV absorber coadditive provides the best protection against yellowing after 12 days exposure.

EXAMPLE 39

Using the ambient test method, BTMP handsheets containing 1%, 0.6% or 0.1% by weight of the hindered amine nitroxide Compound F, 2% by weight of the benzotriazole UV absorber TINUVIN® 328 and 1% by weight of the polymer PEO are compared for efficacy in yellowing. The data are presented on the table below.

TABLE FOR EXAMPLE 39

| Days | p51a | p51b | p51c | p51d | p51e |
|---|---|---|---|---|---|
| 0 | 0.00 | 0.00 | 0.00 | 0.00 | 0.00 |
| 1 | 0.10 | −0.08 | −0.37 | −0.24 | −0.21 |
| 5 | 0.54 | −0.18 | −0.84 | −0.64 | −0.54 |
| 7 | 1.07 | −0.04 | −0.67 | −0.47 | −0.30 |
| 8 | 1.00 | −0.12 | −0.83 | −0.63 | −0.42 |
| 9 | 1.37 | −0.04 | −0.73 | −0.50 | −0.32 |
| 11 | 1.70 | −0.10 | −0.97 | −0.67 | −0.44 |
| 13 | 2.05 | −0.08 | −0.93 | −0.61 | −0.40 |
| 15 | 2.33 | −0.13 | −1.09 | −0.73 | −0.46 |
| 29 | 4.29 | −0.02 | −1.12 | −0.67 | −0.20 |
| 40 | 5.86 | 0.00 | −1.16 | −0.69 | −0.13 |
| 55 | 7.52 | 0.03 | −1.12 | −0.60 | 0.18 |
| 59 | 7.88 | 0.02 | −1.16 | −0.60 | 0.22 |
| 66 | 8.83 | 0.05 | −1.12 | −0.55 | 0.39 |
| 69 | 9.05 | 0.01 | −1.21 | −0.67 | 0.35 |
| 73 | 9.56 | 0.09 | −1.10 | −0.53 | 0.49 |
| 80 | 10.48 | 0.14 | −1.01 | −0.44 | 0.64 |
| 87 | 10.91 | 0.10 | −1.12 | −0.56 | 0.55 |
| 94 | 12.11 | 0.28 | −0.91 | −0.37 | 0.83 |
| 111 | 13.38 | 0.32 | −0.86 | −0.29 | 1.01 |
| 122 | 14.71 | 0.52 | −0.67 | −0.10 | 1.32 |
| 129 | 14.60 | 0.37 | −0.79 | −0.19 | 1.38 |
| 136 | 15.92 | 0.50 | −0.60 | 0.17 | 1.77 |
| 143 | 16.20 | 0.58 | −0.47 | 0.28 | 1.99 |
| 150 | 16.68 | 0.52 | −0.52 | 0.26 | 2.06 |
| 157 | 17.40 | 0.61 | −0.40 | 0.34 | 2.16 |
| 164 | 18.08 | 0.67 | −0.31 | 0.40 | 2.41 |
| 171 | 19.54 | 0.75 | −0.13 | 0.58 | 2.82 |
| 178 | 19.98 | 0.89 | −0.09 | 0.63 | 3.01 |
| 185 | 20.39 | 0.90 | −0.07 | 0.69 | 3.23 |
| 188 | 20.70 | 0.83 | −0.02 | 0.70 | 3.39 |
| 191 | 21.64 | 0.92 | −0.12 | 0.66 | 3.41 |
| 199 | 22.11 | 0.85 | −0.10 | 0.70 | 3.52 |
| 206 | 22.94 | 0.97 | −0.02 | 0.75 | 3.71 |
| 213 | 23.59 | 0.91 | 0.03 | 0.82 | 3.82 |
| 220 | 24.34 | 0.95 | −0.02 | 0.81 | 3.90 |

A is the control containing no stabilizer additives.
B is a control which is a Kraft handsheet.
C contains 1% of the nitroxide.
D contains 0.6% of the nitroxide.
E contains 0.1% of the nitroxide.

As inspection of the data on the table attests, in best to poorest order C≅D≅B>E>>>A. These data show that the nitroxide provides resistance to yellowing particularly at the 0.6 and 1% by weight levels that makes the color after 220 days of exposure essentially equal to that obtained with Kraft paper. Even at the 0.1% level, the nitroxide provides very good resistance to yellowing.

EXAMPLE 40

Using the accelerated test method; the ambient test method; and dark aging, BTMP handsheets containing 0.25%, 0.2%, 0.15%, 0.1% or 0.05% by weight of the hindered amine nitroxide Compound F are compared for efficacy in preventing yellowing. The data are presented on the three tables below respectively.

| Time | a | b | c | d | e | f |
|---|---|---|---|---|---|---|
| Accelerated Test Method | | | | | | |
| 0.00 | 0.00 | 0.00 | 0.00 | 0.00 | 0.00 | 0.00 |
| 24.33 | 2.27 | 2.55 | 3.16 | 3.46 | 3.68 | 5.18 |
| 48.50 | 4.17 | 4.52 | 5.46 | 6.05 | 6.29 | 8.60 |
| 73.25 | 5.71 | 6.18 | 7.46 | 8.05 | 8.62 | 11.65 |
| 97.00 | 7.42 | 7.94 | 9.39 | 10.34 | 10.97 | 14.68 |
| 121.50 | 9.00 | 9.57 | 11.42 | 12.57 | 13.17 | 17.34 |
| 144.50 | 10.56 | 11.28 | 13.32 | 14.53 | 15.36 | 20.05 |
| 168.25 | 12.04 | 12.84 | 15.08 | 16.52 | 17.39 | 22.57 |
| Ambient Test Method | | | | | | |
| 0.00 | 0.00 | 0.00 | 0.00 | 0.00 | 0.00 | 0.00 |
| 3.02 | 0.39 | 0.21 | 0.39 | 0.49 | 0.44 | 0.80 |
| 10.01 | 1.00 | 0.63 | 1.01 | 1.23 | 1.27 | 2.04 |
| 17.00 | 1.33 | 0.90 | 1.44 | 1.78 | 1.82 | 3.01 |
| 31.03 | 1.97 | 1.44 | 2.43 | 2.88 | 3.09 | 5.04 |
| 38.06 | 2.71 | 1.98 | 3.18 | 3.73 | 4.04 | 6.34 |
| 45.15 | 3.24 | 2.50 | 3.84 | 4.48 | 4.80 | 7.33 |
| 52.15 | 3.59 | 2.77 | 4.22 | 4.94 | 5.37 | 8.00 |
| 55.02 | 3.60 | 2.72 | 4.22 | 4.99 | 5.49 | 8.21 |
| 62.02 | 4.31 | 3.28 | 5.04 | 5.91 | 6.36 | 9.28 |
| 66.00 | 4.49 | 3.38 | 5.27 | 6.03 | 6.63 | 9.78 |
| Dark Aging Test Method | | | | | | |
| 0.00 | 0.00 | 0.00 | 0.00 | 0.00 | 0.00 | 0.00 |
| 3.06 | 0.18 | 0.12 | 0.16 | 0.19 | 0.17 | 0.18 |
| 10.04 | 0.23 | 0.18 | 0.21 | 0.23 | 0.22 | |
| 21.02 | 0.16 | 0.13 | 0.16 | 0.19 | 0.19 | 0.31 |
| 24.17 | 0.23 | 0.18 | 0.21 | 0.26 | 0.25 | 0.41 |
| 38.16 | 0.16 | 0.12 | 0.15 | 0.21 | 0.23 | 0.48 |
| 45.15 | 0.21 | 0.17 | 0.21 | 0.27 | 0.28 | 0.57 |

-continued

| Time | a | b | c | d | e | f |
|---|---|---|---|---|---|---|
| 52.01 | 0.20 | 0.15 | 0.19 | 0.25 | 0.26 | 0.58 |
| 62.96 | 0.20 | 0.15 | 0.21 | 0.27 | 0.28 | 0.67 |

A contains 0.25% of the nitroxide.
B contains 0.2% of the nitroxide.
C contains 0.15% of the nitroxide.
D contains 0.1% of the nitroxide.
E contains 0.05% of the nitroxide.
F is a control containing no stabilizer additive.

During accelerated photoaging, inspection of the data on the table shows in best to poorest order A>B>C>D>E>F. These data show that the nitroxide provides resistance to yellowing after 168 hours of accelerated photoaging.

During ambient photoaging, inspection of the data on the table shows in best to poorest order B>A>C>D>E>>F. These data show that the nitroxide provides resistance to yellowing after 66 days of ambient photoaging.

During dark aging, inspection of the data on the table shows in best to poorest order B>C>A>D>E>>F. These data show that the nitroxide provides resistance to yellowing after 63 days of dark aging.

EXAMPLE 41

Using the accelerated test method; the ambient test method; and dark aging, BTMP handsheets containing 0.25% by weight of the hindered amine nitroxide Compound F and 1%, 0.5%, 0.25%, 0.2% or 0.1% by weight of the benzotriazole UV absorber TINUVIN® 1130 are compared for efficacy in preventing yellowing. The data are presented on the three tables below respectively.

| Time | a | b | c | d | e | f |
|---|---|---|---|---|---|---|
| 0.00 | 0.00 | 0.00 | 0.00 | 0.00 | 0.00 | 0.00 |
| 24.50 | 0.28 | 0.53 | 1.14 | 1.30 | 1.88 | 5.39 |
| 49.25 | 0.57 | 0.93 | 1.96 | 2.35 | 3.38 | 8.92 |
| 72.55 | 0.86 | 1.46 | 2.84 | 3.44 | 4.83 | 12.23 |
| 97.50 | 1.20 | 1.92 | 3.66 | 4.57 | 6.35 | 15.14 |
| 120.50 | 1.66 | 2.54 | 4.72 | 5.87 | 7.97 | 18.18 |
| 144.25 | 2.02 | 3.06 | 5.56 | 6.98 | 9.39 | 20.82 |
| 168.50 | 2.57 | 3.73 | 6.71 | 8.34 | 11.05 | 23.47 |
| Ambient Test Method | | | | | | |
| 0.00 | 0.00 | 0.00 | 0.00 | 0.00 | 0.00 | 0.00 |
| 2.02 | 0.09 | −0.03 | 0.03 | −0.02 | 0.00 | 0.41 |
| 9.01 | 0.42 | 0.26 | 0.42 | 0.36 | 0.49 | 1.75 |
| 16.00 | 0.48 | 0.22 | 0.45 | 0.51 | 0.72 | 2.75 |
| 23.02 | 0.58 | 0.38 | 0.73 | 0.79 | 1.05 | 3.90 |
| 30.05 | 0.64 | 0.43 | 0.95 | 0.99 | 1.31 | 4.79 |
| 37.07 | 0.94 | 0.71 | 1.34 | 1.41 | 1.84 | 6.17 |
| 44.15 | 1.11 | 0.96 | 1.72 | 1.76 | 2.27 | 7.26 |
| 51.15 | 1.20 | 1.04 | 1.87 | 1.94 | 2.55 | 7.98 |
| 54.03 | 1.31 | 1.09 | 1.95 | 1.96 | 2.54 | 8.27 |
| 61.02 | 1.49 | 1.29 | 2.35 | 2.35 | 3.04 | 9.29 |
| 64.98 | 1.44 | 1.33 | 2.43 | 2.38 | 3.14 | 9.73 |
| Dark Aging Test Method | | | | | | |
| 0.00 | 0.00 | 0.00 | 0.00 | 0.00 | 0.00 | 0.00 |
| 2.06 | 0.05 | 0.02 | −0.01 | −0.01 | 0.00 | 0.02 |
| 9.04 | 0.12 | 0.10 | 0.05 | 0.06 | 0.08 | 0.15 |
| 20.02 | 0.05 | 0.01 | −0.03 | −0.03 | 0.00 | 0.13 |
| 23.17 | 0.15 | 0.07 | 0.03 | 0.06 | 0.05 | 0.21 |
| 30.17 | 0.06 | 0.00 | −0.04 | −0.05 | −0.03 | 0.20 |
| 37.17 | 0.10 | 0.00 | −0.02 | −0.04 | 0.00 | 0.26 |
| 44.15 | 0.13 | 0.08 | 0.00 | 0.03 | 0.06 | 0.33 |
| 51.06 | 0.15 | 0.03 | −0.01 | 0.00 | 0.04 | 0.37 |
| 61.96 | 0.14 | 0.01 | −0.01 | −0.01 | 0.05 | 0.43 |
| 79.06 | 0.30 | 0.07 | 0.08 | 0.01 | 0.13 | 0.51 |

A contains 1% of the UV absorber.
B contains 0.5% of the UV absorber.
C contains 0.25% of the UV absorber.
D contains 0.2% of the UV absorber.
E contains 0.1% of the UV absorber.
F is a control containing no stabilizer additive.

During accelerated photoaging, inspection of the data on the table shows in best to poorest order A>B>C>D>E>>F. These data show that the nitroxide plus UV absorber provides resistance to yellowing after 168 hours of accelerated photoaging.

During ambient photoaging, inspection of the data on the table shows in best to poorest order B>A>C>D>E>>F. These data show that the nitroxide plus UV absorber provides resistance to yellowing after 65 days of ambient photoaging.

During dark aging, inspection of the data on the table shows in best to poorest order D>B>C>E>A>F. These data show that the nitroxide plus UV absorber provides resistance to yellowing after 79 days of dark aging, but that in the dark the UV absorber is much less critical for efficacy.

EXAMPLE 42

Using the accelerated test method; the ambient test method; and dark aging, BTMP handsheets containing 0.25% by weight of the hindered amine nitroxide Compound B and 1%, 0.75%, 0.5%, 0.25% or 0.1% by weight of the polymer PTHF are compared for efficacy in preventing yellowing. The data are presented on the three tables below respectively.

| Time | a | b | c | d | e | f |
|---|---|---|---|---|---|---|
| Accelerated Test Method | | | | | | |
| 0.00 | 0.00 | 0.00 | 0.00 | 0.00 | 0.00 | 0.00 |
| 25.00 | 1.42 | 1.08 | 1.50 | 1.58 | 1.57 | 4.56 |
| 48.75 | 2.41 | 1.98 | 2.64 | 2.82 | 2.86 | 7.58 |
| 73.25 | 3.63 | 3.07 | 4.04 | 4.37 | 4.46 | 11.08 |
| 96.25 | 4.88 | 4.12 | 5.38 | 5.78 | 5.95 | 14.07 |
| 120.00 | 5.90 | 5.14 | 6.62 | 7.20 | 7.41 | 16.88 |
| 144.25 | 7.20 | 6.22 | 8.14 | 8.64 | 8.84 | 19.74 |
| Ambient Test Method | | | | | | |
| 0.00 | 0.00 | 0.00 | 0.00 | 0.00 | 0.00 | 0.00 |
| 8.00 | 0.37 | 0.24 | 0.17 | 0.41 | 0.45 | 1.66 |
| 14.99 | 0.39 | 0.32 | 0.38 | 0.56 | 0.73 | 2.74 |
| 22.01 | 0.59 | 0.55 | 0.66 | 0.96 | 1.10 | 3.90 |
| 29.02 | 0.78 | 0.74 | 0.85 | 1.25 | 1.42 | 4.88 |
| 36.07 | 1.21 | 1.13 | 1.24 | 1.50 | 2.06 | 6.21 |
| 50.14 | 1.59 | 1.44 | 1.66 | 2.33 | 2.57 | 7.93 |
| 53.01 | 1.66 | 1.51 | 1.73 | 2.37 | 2.65 | 8.16 |
| 60.01 | 2.06 | 1.76 | 2.13 | 2.90 | 3.16 | 9.22 |
| 63.97 | 2.03 | 1.81 | 2.16 | 3.05 | 3.36 | 9.73 |
| 70.99 | 2.29 | 2.07 | 2.60 | 3.55 | 3.89 | 10.75 |
| 77.97 | 2.55 | 2.27 | 2.81 | 3.85 | 4.31 | 11.64 |
| Dark Aging Test Method | | | | | | |
| 0.00 | 0.00 | 0.00 | 0.00 | 0.00 | 0.00 | 0.00 |
| 1.05 | −0.12 | −0.13 | −0.10 | −0.09 | −0.08 | −0.06 |
| 8.03 | −0.12 | −0.10 | −0.07 | −0.09 | −0.08 | 0.05 |
| 19.01 | −0.19 | −0.18 | −0.15 | −0.18 | −0.17 | 0.02 |
| 22.16 | −0.13 | −0.12 | −0.10 | −0.10 | −0.10 | 0.10 |

-continued

| Time  | a     | b     | c     | d     | e     | f    |
|-------|-------|-------|-------|-------|-------|------|
| 29.16 | −0.23 | −0.21 | −0.22 | −0.19 | −0.21 | 0.08 |
| 36.16 | −0.21 | −0.17 | −0.16 | −0.17 | −0.19 | 0.17 |
| 50.05 | −0.21 | −0.16 | −0.15 | −0.17 | −0.19 | 0.28 |

A contains 1% of the polymer PTHF.
B contains 0.75% of the polymer PTHF.
C contains 0.5% of the polymer PTHF.
D contains 0.25% of the polymer PTHF.
E contains 0.1% of the polymer PTHF
F is a control containing no stabilizer additive.

During accelerated photoaging, inspection of the data on the table shows in best to poorest order B>A>C>D>E>>F. These data show that the nitroxide plus polymer provides resistance to yellowing after 144 hours of accelerated photoaging.

During ambient photoaging, inspection of the data on the table shows in best to poorest order B>A>C>D>E>>F. These data show that the nitroxide plus polymer provides resistance to yellowing after 78 days of ambient photoaging.

During dark aging, inspection of the data on the table shows in best to poorest order A>E>D>B>C>>>F. These data show that the nitroxide plus polymer provides resistance to yellowing after 50 days of dark aging.

EXAMPLE 43

Using the accelerated test method; the ambient test method; and dark aging, BTMP handsheets containing 0.25% by weight of the hindered amine nitroxide Compound B, 1%, 0.5%, 0.25%, 0.2% or 0.1% by weight of the benzotriazole UV absorber TINUVIN® 1130 and 0.5% by weight of polymer PTHF are compared for efficacy in preventing yellowing. The data are presented on the three tables below respectively.

| Time   | a     | b     | c     | d     | e     | f     |
|--------|-------|-------|-------|-------|-------|-------|
| Accelerated Test Method ||||||| 
| 0.00   | 0.00  | 0.00  | 0.00  | 0.00  | 0.00  | 0.00  |
| 23.42  | −0.01 | 0.48  | 0.60  | 0.47  | 1.34  | 4.52  |
| 47.25  | 0.34  | 1.22  | 1.32  | 1.18  | 2.65  | 8.11  |
| 71.75  | 0.71  | 1.91  | 2.00  | 1.80  | 3.81  | 11.04 |
| 96.17  | 1.04  | 2.62  | 2.72  | 2.49  | 4.90  | 13.60 |
| 119.75 | 1.64  | 3.42  | 3.51  | 3.28  | 6.40  | 16.52 |
| 145.75 | 2.30  | 5.05  | 5.11  | 4.65  | 8.26  | 20.82 |
| 168.08 | 2.73  | 5.60  | 5.59  | 5.22  | 9.24  | 22.57 |
| Ambient Test Method ||||||| 
| 0.00   | 0.00  | 0.00  | 0.00  | 0.00  | 0.00  | 0.00  |
| 6.98   | −0.14 | 0.20  | −0.01 | 0.07  | 0.48  | 1.79  |
| 13.97  | −0.11 | 0.35  | 0.04  | 0.21  | 0.48  | 2.63  |
| 20.99  | −0.04 | 0.58  | 0.25  | 0.44  | 0.74  | 3.73  |
| 28.01  | 0.02  | 0.71  | 0.37  | 0.63  | 1.01  | 4.73  |
| 35.04  | 0.24  | 1.06  | 0.64  | 0.98  | 1.41  | 6.01  |
| 42.11  | 0.47  | 1.28  | 0.91  | 1.26  | 1.79  | 7.02  |
| 49.11  | 0.55  | 1.29  | 0.88  | 1.36  | 1.87  | 7.78  |
| 51.99  | 0.61  | 1.33  | 0.95  | 1.45  | 1.91  | 8.07  |
| 59.11  | 0.79  | 1.70  | 1.24  | 1.72  | 2.40  | 9.32  |
| 62.97  | 0.76  | 1.78  | 1.25  | 1.77  | 2.52  | 9.70  |
| 69.97  | 1.16  | 2.09  | 1.59  | 2.14  | 3.00  | 10.88 |
| 77.01  | 1.25  | 2.27  | 1.64  | 2.30  | 3.27  | 11.75 |
| Dark Aging Test Method ||||||| 
| 0.00   | 0.00  | 0.00  | 0.00  | 0.00  | 0.00  | 0.00  |
| 6.97   | 0.00  | 0.04  | 0.03  | 0.04  | 0.10  | 0.17  |
| 17.95  | −0.09 | −0.03 | −0.05 | −0.01 | 0.01  | 0.16  |

-continued

| Time  | a     | b     | c     | d     | e     | f    |
|-------|-------|-------|-------|-------|-------|------|
| 21.09 | −0.04 | −0.03 | −0.01 | 0.02  | 0.06  | 0.23 |
| 28.10 | −0.12 | −0.16 | −0.10 | −0.07 | −0.04 | 0.19 |
| 35.10 | −0.07 | −0.10 | −0.07 | −0.02 | −0.02 | 0.28 |
| 48.99 | −0.05 | −0.08 | −0.05 | −0.02 | 0.00  | 0.36 |
| 59.89 | −0.07 | −0.11 | −0.06 | −0.04 | −0.01 | 0.45 |

A contains 1% of the UV absorber.
B contains 0.5% of the UV absorber.
C contains 0.25% of the UV absorber.
D contains 0.2% of the UV absorber.
E contains 0.1% of the UV absorber.
F is a control containing no stabilizer additive.

During accelerated photoaging, inspection of the data on the table shows in best to poorest order A>D>B>C>E>>F. These data show that the nitroxide plus UV absorber plus polymer provides resistance to yellowing after 168 hours of accelerated photoaging.

During ambient photoaging, inspection of the data on the table shows in best to poorest order A>C>D=B>E>>F. These data show that the nitroxide plus UV absorber plus polymer provides resistance to yellowing after 77 days of ambient photoaging.

During dark aging, inspection of the data on the table shows in best to poorest order B>A>C>D>E>F. These data show that the nitroxide plus UV absorber plus polymer provides resistance to yellowing after 60 days of dark aging.

EXAMPLE 44

Using the accelerated test method; the ambient test method; and dark aging, BTMP handsheets containing 0.25%, 0.2%, 0.15%, 0.1% and 0.05% by weight of the hindered amine nitroxide Compound B, 0.5% by weight of the benzotriazole UV absorber TINUVIN® 1130 and 0.5% by weight of polymer PTHF are compared for efficacy in preventing yellowing. The data are presented on the three tables below respectively.

| Time   | a     | b     | c     | d     | e     | f     |
|--------|-------|-------|-------|-------|-------|-------|
| Accelerated Test Method ||||||| 
| 0.00   | 0.00  | 0.00  | 0.00  | 0.00  | 0.00  | 0.00  |
| 26.00  | 0.49  | 0.41  | 1.12  | 1.93  | 2.02  | 6.01  |
| 48.33  | 1.10  | 0.91  | 1.95  | 3.21  | 3.33  | 9.20  |
| 73.50  | 1.63  | 1.39  | 2.73  | 4.47  | 4.55  | 11.87 |
| 96.00  | 2.23  | 1.80  | 3.32  | 5.44  | 5.59  | 14.00 |
| 119.83 | 2.64  | 2.31  | 4.13  | 6.63  | 6.65  | 15.98 |
| 144.83 | 3.16  | 2.76  | 4.81  | 7.70  | 7.64  | 17.94 |
| 167.67 | 3.76  | 3.36  | 5.63  | 8.85  | 8.82  | 19.87 |
| 191.00 | 4.25  | 3.73  | 6.15  | 9.86  | 9.64  | 21.07 |
| 216.42 | 5.20  | 4.73  | 7.58  | 11.69 | 11.18 | 23.66 |
| Ambient Test Method ||||||| 
| 0.00   | 0.00  | 0.00  | 0.00  | 0.00  | 0.00  | 0.00  |
| 1.99   | −0.19 | −0.10 | −0.12 | 0.10  | 0.20  | 0.76  |
| 8.98   | −0.17 | 0.06  | 0.01  | 0.37  | 0.61  | 1.98  |
| 16.00  | −0.08 | 0.17  | 0.22  | 0.70  | 1.09  | 3.14  |
| 23.03  | 0.09  | 0.28  | 0.31  | 0.93  | 1.45  | 3.98  |
| 30.07  | 0.31  | 0.58  | 0.65  | 1.39  | 2.03  | 5.30  |
| 37.13  | 0.56  | 0.80  | 0.99  | 1.85  | 2.47  | 6.30  |
| 44.04  | 0.61  | 0.86  | 1.00  | 1.96  | 2.83  | 7.10  |
| 47.00  | 0.71  | 0.94  | 1.02  | 2.02  | 2.94  | 7.26  |
| 54.00  | 0.93  | 1.18  | 1.35  | 2.36  | 3.47  | 8.36  |
| 57.96  | 0.93  | 1.20  | 1.46  | 2.48  | 3.63  | 8.86  |
| 64.98  | 1.14  | 1.43  | 1.79  | 2.76  | 4.03  | 9.95  |
| 72.00  | 1.27  | 1.75  | 2.04  | 3.21  | 4.61  | 11.01 |

| Time | a | b | c | d | e | f |
|---|---|---|---|---|---|---|
| | Dark Aging Test Method | | | | | |
| 0.00 | 0.00 | 0.00 | 0.00 | 0.00 | 0.00 | 0.00 |
| 2.02 | 0.03 | 0.03 | 0.06 | 0.04 | 0.07 | 0.11 |
| 12.98 | −0.06 | −0.06 | 0.00 | −0.01 | 0.02 | 0.21 |
| 16.15 | −0.01 | −0.01 | 0.03 | 0.03 | 0.07 | 0.28 |
| 23.15 | −0.09 | −0.12 | −0.05 | −0.07 | 0.02 | 0.25 |
| 30.15 | −0.10 | −0.08 | −0.03 | −0.07 | 0.05 | 0.34 |
| 37.13 | −0.06 | −0.06 | −0.01 | −0.01 | 0.08 | 0.38 |
| 44.04 | −0.09 | −0.06 | −0.03 | −0.02 | 0.07 | 0.42 |
| 54.94 | −0.11 | −0.07 | −0.03 | −0.05 | 0.08 | 0.47 |
| 72.03 | 0.00 | −0.04 | 0.00 | −0.03 | 0.11 | 0.56 |

A contains 0.25% of the nitroxide.
B contains 0.2% of the nitroxide.
C contains 0.15% of the nitroxide.
D contains 0.1% of the nitroxide.
E contains 0.05% of the nitroxide.
F is a control containing no stabilizer additive.

During accelerated photoaging, inspection of the data on the table shows in best to poorest order B>A>C>D>E>>F. These data show that the nitroxide plus UV absorber plus polymer provides resistance to yellowing after 216 hours of accelerated photoaging.

During ambient photoaging, inspection of the data on the table shows in best to poorest order A>B>C>D>E>>F. These data show that the nitroxide plus UV absorber plus polymer provides resistance to yellowing after 72 days of ambient photoaging.

During dark aging, inspection of the data on the table shows in best to poorest order B>D>C>A>E>>F. These data show that the nitroxide plus UV absorber plus polymer provides resistance to yellowing after 72 days of dark aging.

EXAMPLE 45

Using the accelerated test method; the ambient test method; and dark aging, BTMP handsheets containing 0.25% by weight of the hindered amine nitroxide Compound B, 0.5% by weight of the benzotriazole UV absorber TINUVIN® 1130 and 1%, 0.75%, 0.25% or 0.1% by weight of the polymer PTHF are compared for efficacy in preventing yellowing. The data are presented on the three tables below respectively.

| Time | a | b | c | d | e |
|---|---|---|---|---|---|
| | Accelerated Test Method | | | | |
| 0.00 | 0.00 | 0.00 | 0.00 | 0.00 | 0.00 |
| 22.33 | 0.49 | 0.86 | 0.31 | 0.45 | 4.68 |
| 47.50 | 1.11 | 1.76 | 0.77 | 1.04 | 7.82 |
| 70.00 | 1.61 | 2.53 | 1.20 | 1.49 | 10.05 |
| 93.00 | 2.26 | 3.36 | 1.73 | 2.08 | 12.46 |
| 118.83 | 2.70 | 4.10 | 2.16 | 2.67 | 14.44 |
| 141.67 | 3.41 | 5.04 | 2.80 | 3.39 | 16.69 |
| 165.00 | 3.95 | 5.74 | 3.20 | 3.90 | 18.16 |
| 189.42 | 4.97 | 7.28 | 4.18 | 5.52 | 21.00 |
| 214.00 | 6.32 | 9.24 | 5.37 | 6.86 | 24.13 |
| | Ambient Test Method | | | | |
| 0.00 | 0.00 | 0.00 | 0.00 | 0.00 | 0.00 |
| 7.90 | −0.21 | 0.13 | −0.20 | −0.07 | 1.75 |
| 14.92 | −0.10 | 0.32 | −0.08 | 0.12 | 2.96 |
| 21.92 | −0.05 | 0.43 | −0.06 | 0.21 | 3.87 |
| 28.98 | 0.24 | 0.74 | 0.19 | 0.52 | 5.15 |
| 43.04 | 0.59 | 1.03 | 0.29 | 1.08 | 6.97 |
| 45.91 | 0.69 | 1.08 | 0.35 | 0.99 | 7.13 |
| 52.88 | 0.90 | 1.40 | 0.55 | 1.26 | 8.23 |
| 56.92 | 0.90 | 1.46 | 0.59 | 1.34 | 8.74 |
| 63.90 | 1.12 | 1.78 | 0.85 | 1.71 | 9.77 |
| | Dark Aging Test Method | | | | |
| 0.00 | 0.00 | 0.00 | 0.00 | 0.00 | 0.00 |
| 0.94 | 0.04 | 0.03 | 0.02 | 0.02 | 0.04 |
| 11.92 | −0.03 | −0.04 | −0.06 | −0.04 | 0.23 |
| 15.06 | 0.03 | 0.00 | −0.01 | 0.01 | 0.33 |
| 22.07 | −0.07 | −0.07 | −0.09 | −0.09 | 0.31 |
| 29.07 | −0.04 | −0.04 | −0.08 | −0.04 | 0.42 |
| 42.96 | −0.03 | 0.04 | −0.06 | −0.05 | 0.49 |
| 53.85 | −0.01 | 0.04 | −0.07 | −0.05 | 0.61 |
| 70.96 | 0.06 | 0.01 | −0.03 | −0.04 | 0.70 | a contains 1% of the polymer PTHF.
b contains 0.75% of the polymer PTHF.
c contains 0.25% of the polymer PTHF.
d contains 0.1% of the polymer PTHF.
e is a control containing no stabilizer additive.

During accelerated photoaging, inspection of the data on the table shows in best to poorest order C>A>D>B>>>E. These data show that the nitroxide plus UV absorber plus polymer provides resistance to yellowing after 214 hours of accelerated photoaging.

During ambient photoaging, inspection of the data on the table shows in best to poorest order C>A>D>B>>>E. These data show that the nitroxide plus UV absorber plus polymer provides resistance to yellowing after 64 days of ambient photoaging.

During dark aging, inspection of the data on the table shows in best to poorest order D>C>B>A>>>E. These data show that the nitroxide plus UV absprber plus polymer provides resistance to yellowing after 71 days of dark aging.

EXAMPLE 46

Using the accelerated test method; the ambient test method; and dark aging, BCTMP Aspen handsheets containing 0.25% by weight of the hindered amine nitroxide Compound B, 1%, 0.5% or 0% by weight of the benzotriazole UV absorber TINUVIN® 1130 and 1%, 0.5% or 0% by weight of the polymer PTHF are compared for efficacy in preventing yellowing. The data are presented on the three tables below respectively.

| Time | a | b | c | d | e |
|---|---|---|---|---|---|
| | Accelerated Test Method | | | | |
| 0.00 | 0.00 | 0.00 | 0.00 | 0.00 | 0.00 |
| 1.00 | 3.50 | 2.59 | 0.77 | 1.02 | 5.81 |
| 2.02 | 5.57 | 3.81 | 1.16 | 1.51 | 8.77 |
| 3.03 | 7.49 | 5.05 | 1.71 | 2.02 | 11.62 |
| 4.01 | 9.04 | 5.82 | 2.06 | 2.46 | 13.93 |
| 4.98 | 10.54 | 6.76 | 2.56 | 2.95 | 16.26 |
| 6.14 | 12.04 | 7.67 | 2.82 | 3.21 | 18.49 |
| 7.64 | 13.90 | 8.61 | 3.37 | 3.81 | 21.64 |
| 8.24 | 14.60 | 8.76 | 3.54 | 3.95 | 22.42 |
| | Ambient Test Method | | | | |
| 0.00 | 0.00 | 0.00 | 0.00 | 0.00 | 0.00 |
| 1.99 | 0.76 | 0.49 | 0.07 | 0.26 | 1.51 |
| 3.06 | 1.27 | 0.84 | 0.28 | 0.48 | 2.44 |
| 24.13 | 1.80 | 1.22 | 0.52 | 0.73 | 3.25 |
| 31.13 | 2.00 | 1.34 | 0.61 | 0.76 | 3.85 |

-continued

| Time | a | b | c | d | e |
|------|------|------|------|------|------|
| 34.02 | 1.94 | 1.33 | 0.61 | 0.79 | 3.93 |
| 41.00 | 2.16 | 1.63 | 0.84 | 0.95 | 4.63 |
| 45.00 | 2.39 | 1.66 | 0.84 | 0.96 | 4.91 |
| 52.14 | 2.81 | 1.66 | 1.04 | 1.13 | 5.57 |
| 59.02 | 3.15 | 1.84 | 1.23 | 1.22 | 6.10 |
| Dark Aging Test Method | | | | | |
| 0.00 | 0.00 | 0.00 | 0.00 | 0.00 | 0.00 |
| 9.17 | −0.04 | −0.03 | 0.01 | −0.02 | 0.01 |
| 16.16 | 0.03 | 0.01 | 0.07 | 0.04 | 0.03 |
| 23.13 | 0.09 | 0.08 | 0.12 | 0.08 | 0.10 |
| 30.06 | 0.07 | 0.03 | 0.10 | 0.03 | 0.05 |
| 40.94 | 0.06 | 0.04 | 0.11 | 0.05 | 0.05 |
| 58.04 | 0.11 | 0.28 | 0.32 | 0.28 | 0.29 | a contains no UV absorber or no polymer PTHF.
b contains no UV absorber and 1% of the polymer PTHF.
c contains 1% of the UV absorber and no polymer PTHF.
d contains 0.5% of the UV absorber and 0.5% of polymer PTHF.
e is a control containing no stabilizer additive.

During accelerated photoaging, inspection of the data on the table shows in best to poorest order C>D>B>A>>E. These data show that the nitroxide plus UV absorber plus polymer provides resistance to yellowing after 8 days of accelerated photoaging.

During ambient photoaging, inspection of the data on the table shows in best to poorest order C>D>B>A>>E. These data show that the nitroxide plus UV absorber plus polymer provides resistance to yellowing after 59 days of ambient photoaging.

During dark aging, inspection of the data on the table shows in best to poorest order A>B>D>E>C. These data show that the nitroxide plus UV absorber plus polymer provides resistance to yellowing after 71 days of dark aging.

EXAMPLE 47

Using the accelerated test method; the ambient test method; and dark aging, stone-ground wood (SGW) handsheets containing 0.25% by weight of the hindered amine nitroxide Compound B, 1%, 0.5% or 0% by weight of the benzotriazole UV absorber TINUVIN® 1130 and 1%, 0.5% or 0% by weight of the polymer PTHF are compared for efficacy in preventing yellowing. The data are presented on the three tables below respectively.

| Time | a | b | c | d | e |
|------|------|------|------|------|------|
| Accelerated Test Method | | | | | |
| 0.00 | 0.00 | 0.00 | 0.00 | 0.00 | 0.00 |
| 0.99 | 3.94 | 3.28 | 0.82 | 1.51 | 8.19 |
| 1.97 | 6.95 | 5.11 | 1.69 | 2.70 | 12.54 |
| 2.94 | 9.75 | 6.84 | 2.48 | 3.81 | 16.70 |
| 4.09 | 12.18 | 8.83 | 3.34 | 5.09 | 20.41 |
| 5.60 | 15.07 | 10.72 | 4.42 | 6.39 | 25.36 |
| 6.20 | 15.74 | 11.24 | 4.83 | 6.90 | 26.84 |
| Ambient Test Method | | | | | |
| 0.00 | 0.00 | 0.00 | 0.00 | 0.00 | 0.00 |
| 6.95 | 0.44 | 0.15 | −0.25 | −0.24 | 1.80 |
| 14.01 | 1.19 | 0.63 | 0.08 | 0.03 | 3.22 |
| 28.08 | 2.27 | 1.28 | 0.51 | 0.36 | 5.25 |
| 30.98 | 2.26 | 1.32 | 0.57 | 0.38 | 5.30 |
| 37.96 | 2.91 | 1.74 | 0.82 | 0.63 | 6.55 |
| 41.94 | 3.03 | 1.86 | 0.89 | 0.70 | 7.13 |
| 48.99 | 3.64 | 2.12 | 1.21 | 0.83 | 8.30 |
| 55.98 | 4.12 | 2.40 | 1.44 | 1.01 | 9.15 |
| Dark Aging Test Method | | | | | |
| 0.00 | 0.00 | 0.00 | 0.00 | 0.00 | 0.00 |
| 7.13 | −0.08 | −0.17 | −0.06 | −0.13 | −0.10 |
| 14.12 | −0.01 | −0.15 | −0.01 | −0.14 | −0.02 |
| 21.08 | 0.16 | 0.02 | 0.10 | 0.00 | 0.18 |
| 28.02 | 0.13 | −0.02 | 0.09 | −0.03 | 0.13 |
| 38.90 | 0.18 | 0.00 | −0.03 | −0.09 | 0.13 |
| 56.00 | 0.88 | 0.13 | 0.31 | 0.05 | 0.28 | a contains no UV absorber or no polymer PTHF.
b contains no UV absorber and 1% of the polymer PTHF.
c contains 1% of the UV absorber and no polymer PTHF.
d contains 0.5% of the UV absorber and 0.5% of polymer PTHF.
e is a control containing no stabilizer additive.

During accelerated photoaging, inspection of the data on the table shows in best to poorest order C>D>B>A>>E. These data show that the nitroxide plus UV absorber plus polymer provides resistance to yellowing after 6 days of accelerated photoaging.

During ambient photoaging, inspection of the data on the table shows in best to poorest order D>C>B>A>>E. These data show that the nitroxide plus UV absorber plus polymer provides resistance to yellowing after 56 days of ambient photoaging.

During dark aging, inspection of the data on the table shows in best to poorest order D>B>E>C>A. These data show that the nitroxide plus UV absorber plus polymer provides resistance to yellowing after 56 days of dark aging.

EXAMPLE 48

Using the accelerated test method; the ambient test method; and dark aging, BTMP paper loadings with 0.25%, 0.2%, 0.15%, 0.1% amd 0.05% by weight of hindered amine nitroxide Compound B and 0.5% by weight of Compound LL are compared for efficacy in preventing yellowing on aging. The data are presented on the three tables below respectively.

| Time | a | b | c | d | e | f | g | h |
|------|------|------|------|------|------|------|------|------|
| Accelerated Test Method | | | | | | | | |
| 0.00 | 0.00 | 0.00 | 0.00 | 0.00 | 0.00 | 0.00 | 0.00 | 0.00 |
| 24.67 | 2.94 | 2.72 | 3.19 | 3.46 | 4.29 | 4.76 | 6.70 | 6.48 |
| 48.25 | 5.79 | 5.16 | 5.68 | 6.06 | 7.46 | 8.16 | 10.98 | 10.98 |
| 71.75 | 7.60 | 7.25 | 7.93 | 8.31 | 10.03 | 11.02 | 14.43 | 14.37 |
| 97.08 | 9.13 | 8.83 | 9.60 | 10.13 | 11.85 | 13.14 | 16.98 | 17.00 |
| 120.25 | 10.76 | 10.55 | 11.21 | 11.72 | 13.58 | 15.01 | 19.31 | 19.34 |
| 168.25 | 14.63 | 14.71 | 15.52 | 15.17 | 15.52 | 18.08 | 19.76 | 25.10 | 25.36 |
| Ambient Test Method | | | | | | | | |
| 0.00 | 0.00 | 0.00 | 0.00 | 0.00 | 0.00 | 0.00 | 0.00 | 0.00 |
| 8.01 | 0.39 | 0.21 | 0.54 | 0.50 | 0.68 | 1.13 | 1.91 | 2.05 |
| 15.03 | 0.62 | 0.41 | 0.81 | 0.80 | 1.05 | 1.67 | 2.80 | 3.02 |
| 22.05 | 1.19 | 0.89 | 1.30 | 1.28 | 1.62 | 2.44 | 3.92 | 4.31 |
| 29.14 | 1.74 | 1.25 | 1.74 | 1.78 | 2.13 | 3.17 | 4.88 | 5.38 |
| 36.14 | 2.07 | 1.45 | 2.00 | 2.00 | 2.48 | 3.56 | 5.65 | 6.25 |
| 39.01 | 2.03 | 1.47 | 2.01 | 2.06 | 2.50 | 3.60 | 5.75 | 6.46 |
| 46.01 | 2.46 | 1.98 | 2.53 | 2.53 | 3.11 | 4.42 | 6.82 | 7.62 |
| 50.01 | 2.62 | 2.04 | 2.67 | 2.71 | 3.31 | 4.74 | 7.28 | 8.10 |
| 56.99 | 3.06 | 2.40 | 3.09 | 3.11 | 3.71 | 5.33 | 8.24 | 9.17 |
| 64.01 | 3.36 | 2.80 | 3.46 | 3.42 | 4.25 | 5.94 | 9.19 | 10.03 |

-continued

| Time | a | b | c | d | e | f | g | h |
|------|------|------|------|------|------|------|------|------|
| Dark Aging Test Method | | | | | | | | |
| 0.00 | 0.00 | 0.00 | 0.00 | 0.00 | 0.00 | 0.00 | 0.00 | 0.00 |
| 8.16 | 0.09 | −0.06 | 0.02 | 0.08 | 0.02 | 0.05 | 0.13 | 0.17 |
| 15.17 | −0.08 | −0.21 | −0.11 | −0.05 | −0.07 | −0.05 | 0.10 | 0.18 |
| 22.18 | −0.13 | −0.22 | −0.17 | −0.11 | −0.09 | −0.07 | 0.13 | 0.30 |
| 29.14 | 0.01 | −0.16 | 0.01 | 0.06 | 0.01 | 0.06 | 0.29 | 0.40 |
| 36.07 | 0.00 | −0.22 | −0.05 | 0.02 | −0.02 | 0.03 | 0.27 | 0.40 |
| 46.95 | −0.07 | −0.21 | −0.05 | 0.01 | −0.03 | 0.04 | 0.32 | 0.49 |

A contains 0.25% nitroxide and 0.5% brightener.
B contains 0.25% nitroxide and no brightener.
C contains 0.2% nitroxide and 0.5% brightener.
D contains 0.15% nitroxide and 0.5% brightener.
E contains 0.1% nitroxide and 0.5% brightener.
F contains 0.05% nitroxide and 0.5% brightener.
G is a control containing no nitroxide and 0.5% brightener.
H is a control containing no stabilizer additive.

During accelerated photoaging, inspection of the data on the table shows in best to poorest order A>B>C>D>E>F>>G=H. These data show that the nitroxide plus brightner provides resistance to yellowing after 168 hours of accelerated photoaging.

During ambient photoaging, inspection of the data on the table shows in best to poorest order B>A=C=D>E>F>G>H. These data show that the nitroxide plus brightner provides resistance to yellowing after 64 days of ambient photoaging.

During dark aging, inspection of the data on the table shows in best to poorest order B>C>A>E>D>F>G>H. These data show that the nitroxide plus brightner provides resistance to yellowing after 47 days of dark aging.

EXAMPLE 49

Using the dark aging method, BTMP handsheets are allowed to sit in the dark for 10 days before treatment with 0.05% by weight of nitroxide Compound B. The sheets are then dark aged for a period of 72 days. The ISO brightness data are given on the table below.

| Days | e | f |
|------|------|------|
| −10 | 78.11 | 78.22 |
| 0 | 77.94 | 77.48 |
| 2.02 | 77.71 | 77.14 |
| 12.98 | 77.89 | 76.85 |
| 16.15 | 77.72 | 76.65 |
| 23.15 | 77.87 | 76.75 |
| 30.15 | 77.8 | 76.48 |
| 37.13 | 77.68 | 76.37 |
| 44.04 | 77.74 | 76.28 |
| 54.94 | 77.7 | 76.13 |
| 72.03 | 77.6 | 75.89 | e contains 0.05% nitroxide.
f is a control containing no stabilizer additive.

The nitroxide provides the good ISO brightness values after the 72 day period of dark aging.

EXAMPLE 50

Accelerated Yellowing with High Intensity Lamps

BTMP sheets are treated with 0.5% by weight of Compound S and 0.5% by weight of Compound A and Compound FF

| Time in days | S, A | S, FF | S | A | FF | Control |
|------|------|------|------|------|------|------|
| | | | PC Number | | | |
| 0 | 0 | 0 | 0 | 0 | 0 | 0 |
| 0.78 | 0.14 | −0.23 | 1.93 | 0.7 | 0.67 | 3.26 |
| 1.75 | 0.38 | −0.32 | 3.77 | 1.12 | 1.09 | 6.19 |
| 2.75 | 0.85 | −0.19 | 5.8 | 1.93 | 1.86 | 9.16 |
| 3.77 | 1.25 | −0.14 | 7.62 | 2.51 | 2.45 | 11.6 |
| 4.77 | 1.54 | −0.22 | 9.48 | 3.19 | 3.07 | 13.8 |
| 5.75 | 1.87 | −0.07 | 10.9 | 3.74 | 3.59 | 15.83 |
| 6.78 | 2.16 | −0.13 | 11.87 | 4.22 | 4.07 | 16.97 |

Inspection of the data reveals that hydroxylamine citrate salt are more effective in inhibiting yellowing than the hydroxylamine and in combination with a UVA superior results are achieved with the citrate salt.

EXAMPLE 51

Accelerated Yellowing with High Intensity Lamps

BTMP sheets are treated with 0.25% by weight of Compound A and with 1% by weight of the sulfur containing inhibitors:

2-(2′-methoxyethoxy)-ethanethiol;
2,2′-oxydiethanethiol;
1-thioglycerol;
sodium thioglycolate;
thiolactic acid;
sodium thiolactate;
β-mercaptopropionic acid;
sodium β-mercaptopropionate;
glycol dimercaptoacetate;
glycol dimercaptopropionate;
polyethylene glycol dimercaptoacetate;
polyethylene glycol dimercaptopropionate;
pentaerythritol tetrathioglycolate;
trimethylol propane tri-(3-mercaptopropionate);
polymethylene sulfide;
disodium methylene bis thiopropionate;
3,3′-thiodipropionic acid;
dithiothreitol.

The sheets treated with a combination of hydroxylamine and sulfur containing compounds exhibit substantial inhibition to yellowing compared to the untreated control sheet and illustrate the performance enhancement when combinations of hydroxylamine and sulfur containing compounds are used.

EXAMPLE 52

Accelerated Yellowing with High Intensity Lamps

BTMP sheets are treated with 0.25% by weight of Compound FF and with 1% by weight of the sulfur containing inhibitors:

2-(2′-methoxyethoxy)-ethanethiol;
2,2′-oxydiethanethiol;
1-thioglycerol;
sodium thioglycolate;
thiolactic acid;
sodium thiolactate;

β-mercaptopropionic acid;
sodium β-mercaptopropionate;
glycol dimercaptoacetate;
glycol dimercaptopropionate;
polyethylene glycol dimercaptoacetate;
polyethylene glycol dimercaptopropionate;
pentaerythritol tetrathioglycolate;
trimethylol propane tri-(3-mercaptopropionate);
polymethylene sulfide;
disodium methylene bis thiopropionate;
3,3'-thiodipropionic acid;
dithiothreitol.

The sheets treated with a combination of hydroxylamine salt and sulfur containing compounds exhibit substantial inhibition to yellowing compared to the untreated control sheet and illustrate the performance enhancement when combinations of hydroxylamine salt and sulfur containing compounds are used.

EXAMPLE 53

Accelerated Yellowing with High Intensity Lamps

BTMP sheets are treated with 0.25% by weight of Compound B and with 1% by weight of the sulfur containing inhibitors Compounds GG, HH and II

| Time in Days | B, GG | B, HH | B, II | GG | HH | II | control |
|---|---|---|---|---|---|---|---|
| | | | | PC Number | | | |
| 0 | 0 | 0 | 0 | 0 | 0 | 0 | 0 |
| 0.92 | 1.1 | 1.25 | 1.1 | 2.92 | 3.65 | 2.55 | 3.94 |
| 1.88 | 2.4 | 2.32 | 2.09 | 5.9 | 6.45 | 4.93 | 6.91 |
| 3.9 | 5.33 | 4.36 | 3.98 | 11.88 | 11.48 | 9.81 | 12.15 |
| 5 | 7.31 | 5.59 | 5.13 | 15.56 | 14.26 | 12.86 | 14.84 |
| 5.98 | 9.37 | 6.88 | 6.32 | 18.55 | 16.58 | 15.5 | 17.13 |
| 6.95 | 11.32 | 8.06 | 7.37 | 21.3 | 18.51 | 17.75 | 18.93 |
| 7.92 | 13.34 | 9.17 | 8.55 | 24.39 | 20.74 | 20.43 | 21.43 |
| 8.88 | 15.1 | 10.34 | 9.72 | 27.33 | 22.74 | 22.9 | 23.55 |

The sheets treated with a combination of nitroxide and sulfur containing compounds exhibit substantial inhibition to yellowing compared to the untreated control sheet and illustrate the performance enhancement when combinations of nitroxides and sulfur containing compounds are used. Inspection of the data reveals that Compound HH and II are particularly effective when combined with a nitroxide.

EXAMPLE 54

Accelerated Yellowing with High Intensity Lamps

BTMP sheets are treated with 0.25% by weight of Compound A, 0.5% of Compound R and with 1% by weight of the sulfur containing inhibitors:

2-(2'-methoxyethoxy)-ethanethiol;
2,2'-oxydiethanethiol;
1-thioglycerol;
sodium thioglycolate;
thiolactic acid;
sodium thiolactate;
β-mercaptopropionic acid;
sodium β-mercaptopropionate;
glycol dimercaptoacetate;
glycol dimercaptopropionate;
polyethylene glycol dimercaptoacetate;
polyethylene glycol dimercaptopropionate;
pentaerythritol tetrathioglycolate;
trimethylol propane tri-(3-mercaptopropionate);
polymethylene sulfide;
disodium methylene bis thiopropionate;
3,3'-thiodipropionic acid;
dithiothreitol.

The sheets treated with a combination of hydroxylamine, UVA and sulfur containing compounds exhibit substantial inhibition to yellowing compared to the untreated control sheet and illustrate the performance enhancement when combinations of hydroxylamine, UVA and sulfur containing compounds are used.

EXAMPLE 56

Accelerated Yellowing with High Intensity Lamps

BTMP sheets are treated with 0.25% by weight of Compound FF, 0.5% of Compound R and with 1% by weight of the sulfur containing inhibitors:

2-(2'-methoxyethoxy)-ethanethiol;
2,2'-oxydiethanethiol;
1-thioglycerol;
sodium thioglycolate;
thiolactic acid;
sodium thiolactate;
β-mercaptopropionic acid;
sodium β-mercaptopropionate;
glycol dimercaptoacetate;
glycol dimercaptopropionate;
polyethylene glycol dimercaptoacetate;
polyethylene glycol dimercaptopropionate;
pentaerythritol tetrathioglycolate;
trimethylol propane tri-(3-mercaptopropionate);
polymethylene sulfide;
disodium methylene bis thiopropionate;
3,3'-thiodipropionic acid;
dithiothreitol.

The sheets treated with a combination of hydroxylamine salt, UVA and sulfur containing compounds exhibit substantial inhibition to yellowing compared to the untreated control sheet and illustrate the performance enhancement when combinations of hydroxylamine salt, UVA and sulfur containing compounds are used.

EXAMPLE 57

Accelerated Yellowing with High Intensity Lamps

BTMP sheets are treated with 0.25% by weight of Compound B, 0.5% of Compound R and with 1% by weight of the sulfur containing inhibitors Compounds GG, HH and II

| Time in Days | R | B | R, B, GG | R, B, HH | R, B, II | R, GG | R, HH | R, II | control |
|---|---|---|---|---|---|---|---|---|---|
| | | | | | PC Number | | | | |
| 0 | 0 | 0 | 0 | 0 | 0 | 0 | 0 | 0 | 0 |
| 0.92 | 1.62 | 1.52 | 0.97 | 0.48 | 0.5 | 1.58 | 1.92 | 1.51 | 3.94 |
| 1.88 | 3.05 | 3 | 2.08 | 1.1 | 1.2 | 3.23 | 3.56 | 3.08 | 6.91 |
| 3.9 | 5.8 | 5.99 | 4.33 | 2.14 | 2.55 | 6.65 | 6.75 | 6.35 | 12.15 |
| 5 | 7.47 | 7.58 | 5.82 | 2.99 | 3.65 | 9.12 | 8.93 | 8.63 | 14.84 |
| 5.98 | 9.07 | 9 | 7.26 | 3.82 | 4.7 | 11.17 | 10.65 | 10.59 | 17.13 |
| 6.95 | 10.28 | 10.35 | 8.43 | 4.58 | 5.78 | 12.99 | 12.25 | 12.36 | 18.93 |
| 7.92 | 11.58 | 11.72 | 10.03 | 5.38 | 6.77 | 14.95 | 14.05 | 14.36 | 21.43 |
| 8.88 | 12.9 | 12.88 | 11.21 | 6.13 | 7.89 | 17.25 | 15.97 | 16.12 | 23.55 |

The sheets treated with a combination of nitroxide, UVA and sulfur containing compounds exhibit substantial inhibition to yellowing compared to the untreated control sheet and illustrate the performance enhancement when combinations of nitroxides, UVA and sulfur containing compounds are used. Inspection of the data reveals that Compound HH and II are particularly effective when combined with a nitroxide and UVA.

EXAMPLE 58

Accelerated Yellowing with High Intensity Lamps

BTMP sheets are treated with 0.25% by weight of Compound A and with 1% by weight of the following metal salts:
$MgSO_4$
$MnSO_4$
$ZnSO_4$ The sheets treated with a combination of hydroxylamine and metal salt exhibit substantial inhibition to yellowing compared to the untreated control sheet and illustrate the performance enhancement when combinations of hydroxylamine and metal salt are used.

EXAMPLE 59

Accelerated Yellowing with High Intensity Lamps

BTMP sheets are treated with 0.25% by weight of Compound B and with 1% by weight of the following metal salts:
$MgSO_4$
$MnSO_4$
$ZnSO_4$ The sheets treated with a combination of nitroxide and metal salt exhibit substantial inhibition to yellowing compared to the untreated control sheet and illustrate the performance enhancement when combinations of nitroxide and metal salt are used.

EXAMPLE 60

Accelerated Yellowing with High Intensity Lamps

BTMP sheets are treated with 0.25% by weight of Compound A and with 1% by weight of the diene compounds:
1-methoxy-1,3-cyclohexadiene;
1-methoxy-1,4-cyclohexadiene;
2,4-hexadienoic acid;
trans, trans-2,4-hexadien-1-ol.

The sheets treated with a combination of hydroxylamine and diene compound exhibit substantial inhibition to yellowing compared to the untreated control sheet and illustrate the performance enhancement when combinations of hydroxylamine and diene compound are used.

EXAMPLE 61

Accelerated Yellowing with High Intensity Lamps

BTMP sheets are treated with 0.25% by weight of Compound B and with 1% by weight of the following diene compounds:
1-methoxy-1,3-cyclohexadiene;
1-methoxy-1,4-cyclohexadiene;
2,4-hexadienoic acid;
trans, trans-2,4-hexadien-1-ol.

The sheets treated with a combination of nitroxide and diene compound exhibit substantial inhibition to yellowing compared to the untreated control sheet and illustrate the performance enhancement when combinations of nitroxide and compounds are used.

EXAMPLE 62

Accelerated Yellowing with High Intensity Lamps

BTMP sheets are treated with 0.25% by weight of Compound FF and with 1% by weight of the following diene compounds:
1-methoxy-1,3-cyclohexadiene;
1-methoxy-1,4-cyclohexadiene;
2,4-hexadienoic acid;
trans, trans-2,4-hexadien-1-ol.

The sheets treated with a combination of hydroxylamine salt and diene compound exhibit substantial inhibition to yellowing compared to the untreated control sheet and illustrate the performance enhancement when combinations of hydroxylamine salt and compounds are used.

EXAMPLE 63

1-Oxyl-2,2,6,6-tetramethyl-4-glycidyloxypiperidine

A vigorously stirred two phase solution of 1-oxyl-2,2,6,6-tetramethyl-4-hydroxypiperidine, epichlorohydrin, tetrabutylammonium bromide in 50% aqueous sodium hydroxide and toluene is reacted together. The organic phase is dried over anhydrous magnesium sulfate and concentrated to yield the title compound as a low melting red solid after column chromatography.

EXAMPLE 64

1-Oxyl-2,2,6,6-tetramethyl-4-(2-hydroxy-4-oxa-6-trimethylammmoniumhexyloxy)piperidine Chloride The title compound is prepared by reacting the glycidyloxy compound of Example 63 with choline chloride [(2-hydroxyethyl)trimethylammonium chloride].

EXAMPLE 65

1-Oxyl-2,2,6,6-tetramethyl-4-(2-hydroxy-3-trimethylammoniumpropoxy)piperidine Chloride To 25 mL of 0.4 molar aqueous trimethylammonium hydroxide (0.01 mol) is added 2.28 g (0.01 mol) of 1-oxyl-2,2,6,6-tetramethyl4-glycidyloxypiperidine. The mixture is stirred at ambient temperature for 16 hours. The solution is then neutralized with one equivalent of hydrochloric acid, washed twice with 50 mL of ethyl acetate and concentrated under reduced pressure. The resulting red oil is purified by column chromatography yielding 1.0 g of the title compound as a red oil.

EXAMPLE 66

1-Oxyl-2,2,6,6-tetramethyl-4-{2-hydroxy-3-[di(2-hydroxyethyl)amino]propoxy}piperidine A solution of 2.28 g (0.01 mol) of 1-oxyl-2,2,6,6-tetramethyl-4-glycidyloxypiperidine and 1.05 g (0.01 mol) of diethanolamine in 25 mL of water is stirred at ambient temperature for 16 hours. The solution is then extracted with methylene chloride. The methylene chloride extract is dried over anhydrous magnesium sulfate, filter and concentrated. The crude reaction product is purified by column chromatography to afford 1.0 g of the title compound as a red oil.

EXAMPLE 67

1-Oxyl-2,2,6,6-tetramethyl-4-(2-hydroxy-3-dimethylaminopropoxy)piperidine

A mixture of 10.0 g (0.044 mol) of 1-oxyl-2,2,6,6-tetramethyl-4-glycidyloxypiperidine and 10 mL of 40% (ca. 0.091 mol) of dimethylamine (w/w) is dissolved in 100 mL of water and then stirred for 16 hours at ambient temperature. Water is then removed by vacuum distillation to leave 10 g of the title compound as a red oil.

EXAMPLE 68

1-Oxyl-2,2,6,6-tetramethyl-4-(2-hydroxy-3-diethylaminopropoxy)piperidine

The title compound is prepared according to the procedure of Example 67 when the dimethylamine is replaced with an equivalent amount of diethylamine. The product is purified by column chromatography and is isolated as a red oil.

EXAMPLE 69

N,N'-Dimethyl-N,N'-bis-[3-(1-oxyl-2,2,6,6-tetramethylpiperidin-4-yloxy)-2-hydroxypropyl]hexamethylenediamine The title compound is prepared according to the procedure of Example 66 replacing diethanolamine with an equivalent amount of N,N'dimethylhexamethylenediamine. The product is purified by column chromatography and is isolated as a red oil.

EXAMPLE 70

N,N,N',N'-Tetramethyl-N,N'-bis-[3-(1-oxyl-2,2,6,6-tetramethylpiperidin-4-yloxy)-2-hydroxypropyl]hexamethylenediammonium Dibromide A solution of 3.0 g (0.011 mol) of the compound of Example 67 and 0.89 g (0.0036 mol) of dibromohexane om 25 mL of absolute ethanol is refluxed for 16 hours. The resultant solution is concentrated under reduced pressure and the residue is washed thrice with 20 mL of ethyl acetate and then dried under vacuum. The title compound is obtained in a yield of 3.0 g as a red solid.

EXAMPLE 71

1-Oxyl-2,2,6,6-tetramethyl-4-[2-hydroxy-3-(N,N-dimethyl-N-propylammonium)propoxy]piperidine Chloride The title compound is prepared according to the procedure of Example 70 by replacing 1,6-dibromohexane with an equivalent amount of 1-bromopropane. The title compound is isolated as a red oil.

EXAMPLE 72

Ethyl 1-Oxyl-2,2,6,6-tetramethylpiperidin-4-yloxyacetate

To a solution of 3.0 g (17 mmol) of 1-oxyl-2,2,6,6-tetramethyl-4-hydroxypiperidine in 25 mL of anhydrous tetrahydrofuran is added 0.48 g (20 mmol) of sodium hydride. The reaction mixture is stirred under a blanket of nitrogen for one hour. The mixture is then chilled to 0° C. amd 2.9 g (17 mmol) of ethyl bromoacetate is added dropwise. After the addition, the reaction mixture is stirred for an additional 30 minutes during which time a precipitate forms. The mixture is filtered and the solvent is removed under reduced pressure. The title compound is isolated after column chromatography as an orange solid melting at 41–43° C.

EXAMPLE 73

1-Oxyl-2,2,6,6-tetramethylpiperidin-4-yloxyacetic Acid

To a solution of 0.2 g of sodium hydroxide in 20 mL of 1:1 water:methanol is added 1.0 g (39 mmol) of the compound of Example 72. The mixture is stirred for one hour and then carefully acidified with 1% aqueous hydrochloric acid. The resultant mixture is extracted with ethyl acetate. The organic extract is dried over anhydrous magnesium sulfate and concentrated under reduced pressure to afford the title compound as an orange solid.

EXAMPLE 74

Sodium 1-Oxyl-2,2,6,6-tetramethylpiperidin-4-yloxyacetate

To a solution of 1.0 g (4.3 mmol) of the compound of Example 73 dissolved in 20 mL of water is added 0.17 g (4.3 mmol) of sodium hydroxide. The solution is stirred for one hour and the water is then removed by vacuum distillation to afford the title compound as an orange solid.

EXAMPLE 75

1-Oxyl-2,2,6,6-tetramethylpiperidin-4-yloxyacetic Acid Choline Ester

The title compound is prepared by reacting the acid of Example 73 with choline chloride [(2-hydroxyethyl)trimethylammonium chloride].

EXAMPLE 76

1-Hydroxy-2,2,6,6-tetramethyl-4-hydroxypiperidinium Chloride 67 mL of isopropanol is cooled to 0° C. and saturated with HCl gas. This solution is added dropwise to a mechanically stirred solution of 50 g (0.29 mol) 1-oxyl-2,2,6,6-tetramethyl-4-hydroxypiperidine in 130 mL of isopropanol, maintaining a reaction temperature of about 20° C. by occasionally cooling with an ice bath. The HCl salt is vacuum filtered and washed with isopropanol, giving a pale yellow solid. 5.0 g of this crude product is recrystallized from 100 mL isopropanol affording 3 g of a white crystalline solid, mp>260° C.

Elemental Analysis:

|  | Calc. | Found |
|---|---|---|
| % C | 51.55 | 51.30 |
| % H | 9.61 | 9.70 |
| % N | 6.68 | 6.42 |
| % Cl | 16.91 | 16.83 |

EXAMPLE 77

1-Hydroxy-2,2,6,6-tetramethyl-4-hydroxypiperidinium Acetate 5.0 g (0.029 mol) 1-hydroxy-2,2,6,6-tetramethyl-4-hydroxypiperidine and 2.0 g (0.033 mol) acetic acid are recrystallized from 50 mL of isopropanol, yielding 4.0 g of the desired hydroxylamine salt as a white crystalline solid, mp 140–143° C.

Elemental Analysis:

|  | Calc. | Found |
|---|---|---|
| % C | 56.63 | 56.78 |
| % H | 9.94 | 10.13 |
| % N | 6.00 | 6.07 |

EXAMPLE 78

1-Hydroxy-2,2,6,6-tetramethyl-4-hydroxypiperidinium Bisulfate 5.0 g (0.029 mol) 1-hydroxy-2,2,6,6-tetramethyl-4-hydroxypiperidine and 3.0 g (0.031 mol) sulfuric acid are recrystallized from 50 mL of isopropanol, yielding 3.0 g of the desired hydroxylamine salt as a white crystalline solid, mp 238–241° C.

Elemental Analysis:

|  | Calc. | Found |
|---|---|---|
| % C | 39.99 | 40.06 |
| % H | 7.46 | 8.06 |
| % N | 5.18 | 5.11 |
| % S | 11.86 | 11.87 |

EXAMPLE 79

1-Hydroxy-2,2,6,6-tetramethyl-4-acetamidopiperidinium Bisulfate 2.6 ml of concentrated sulfuric acid is added dropwise to a solution of 10.0 g (46.9 mmol) 1-oxyl-2,2,6,6-tetramethyl-4-acetamidopiperidine in 50 ml isopropanol. After 48 hrs the resulting white solid is collected by filtration, washed with isopropanol and dried under vacuum, mp 198° C.

Elemental Analysis:

|  | Calc. | Found |
|---|---|---|
| % C | 42.28 | 42.23 |
| % H | 7.76 | 7.76 |
| % N | 8.97 | 8.85 |

EXAMPLE 80

Bis-(1-hydroxy-2,2,6,6-tetramethyl-4-hydroxypiperidinium) Oxalate

To a glass 0.5L reaction bottle are added 10.0 g (58 mmol) of C, 5.22 g (58 mmol) oxalic acid, 200 mg 5% Pt on C and 100 mL water. Catalytic hydrogenation is carried out at 50 psi for 30 minutes at room temperature. Catalyst is removed by vacuum filtration with Celite. Water is removed by distillation under reduced pressure, giving a colorless solid. The crude product is recrystallized from 100 mL isopropanol affording 3.5 g of the product as a white crystalline solid, mp 244° C.

Elemental Analysis:

|  | Calc. | Found |
|---|---|---|
| % C | 55.03 | 54.69 |
| % H | 9.24 | 9.49 |
| % N | 6.42 | 6.32 |

EXAMPLE 81

Tris-(1-hydroxy-2,2,6,6-tetramethyl-4-hydroxypiperidinium) Citrate

To a glass 0.5 L reaction bottle are added 20.0 g (116 mmol) of 1-oxyl-2,2,6,6-tetramethyl-4-hydroxypiperidine, 7.39 g (38.5 mmol) citric acid, 200 mg 5% Pt on C and 100 mL water. Catalytic hydrogenation is carried out at 50 psi for 30 minutes at room temperature. Catalyst is removed by filtration through a pad of Celite. The aqueous salt solution has a pH of 5.56. Removal of water yields the product as a hygroscopic glassy solid.

EXAMPLE 82

Bis-(1-hydroxy-2,2,6,6-tetramethyl-4-hydroxypiperidinium) Citrate

To a glass 0.5L reaction bottle are added 20.0 g (116 mmol) of 1-oxyl-2,2,6,6-tetramethyl-4-hydroxypiperidine, 11.12 g (58 mmol) citric acid, 200 mg 5% Pt on C and 100 mL water. Catalytic hydrogenation is carried out at 50 psi for 30 minutes at room temperature. Catalyst is removed by filtration through a pad of Celite. The aqueous salt solution has a pH of 4.39. Removal of water yields the product as a hygroscopic glassy solid.

EXAMPLE 83

1-Hydroxy-2,2,6,6-tetramethyl-4-hydroxypiperidinium Citrate

To a glass 0.5L reaction bottle are added 20.0 g (116 mmol) of 1-oxyl-2,2,6,6-tetramethyl-4-hydroxypiperidine, 22.2 g (116 mmol) citric acid, 200 mg 5% Pt on C and 100 mL water. Catalytic hydrogenation is carried out at 50 psi for 30 minutes at room temperature. Catalyst is removed by filtration through a pad of Celite. The aqueous salt solution has a pH of 3.30. Removal of water yields the product as a hygroscopic glassy solid.

EXAMPLE 84

Bis-(1-hydroxy-2,2,6,6-tetramethyl-4-hydroxypiperidinium) Sulfate

To a glass 0.5L reaction bottle are added 10.0 g (58 mmol) of 1-oxyl-2,2,6,6-tetramethyl-4-hydroxypiperidine, 2.85 g (29 mmol) sulfuric acid, 200 mg 5% Pt on C and 100 mL water. Catalytic hydrogenation is carried out at 50 psi for 30 minutes at room temperature. Catalyst is removed by filtration through a pad of Celite. Removal of water yields the product as an pale yellow solid.

What is claimed is:

1. A composition having reduced loss of brightness and enhanced resistance to yellowing which comprises
   (a) paper which still contains lignin, and
   (b) and effective stabilizing amount of a hindered amine compound of formula I

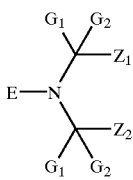

(I)

where
   $G_1$ and $G_2$ are independently alkyl of 1 to 4 carbon atoms or are together pentamethylene,
   $Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group, and
   E is oxyl.

2. A composition according to claim 1 wherein the hindered amine compound of component (b) is selected from the compounds of formulae A to EE

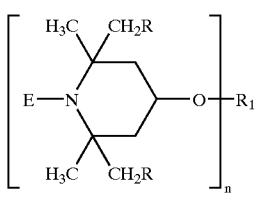

(A)

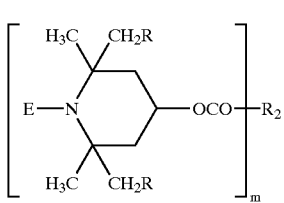

(B)

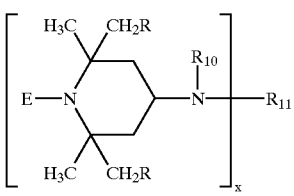

(C)

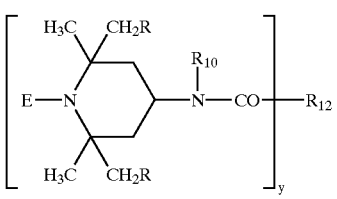

(D)

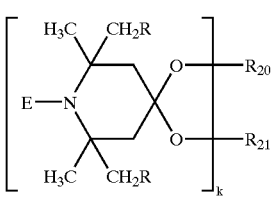

(E)

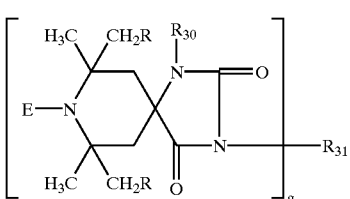

(F)

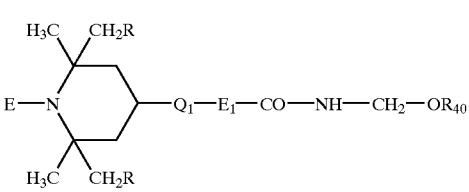

(G)

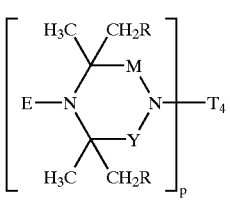

(H)

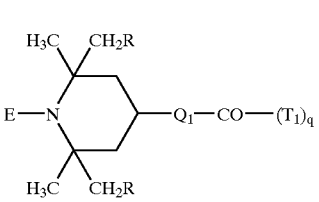

(I)

(J) 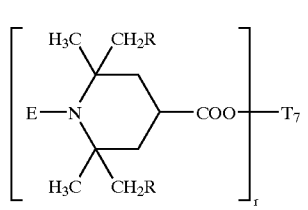
(K) 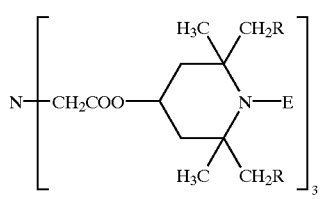
(L) 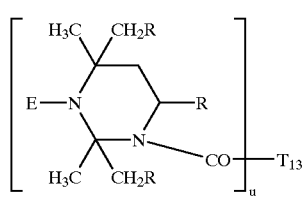
(M) 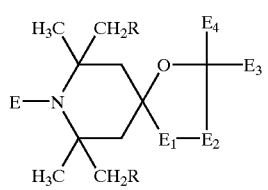
(N) 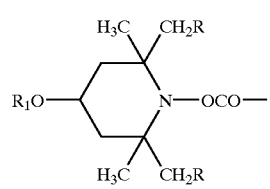 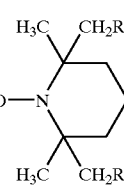
(O) 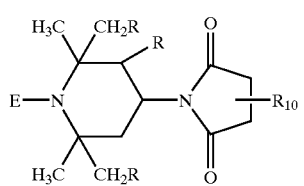
(P) 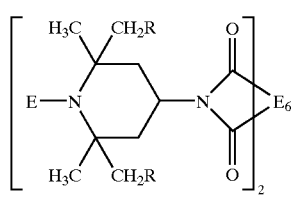
(Q) 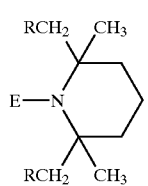
(R) 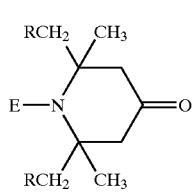
(S) 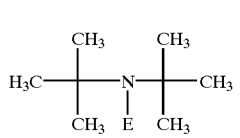
(T) 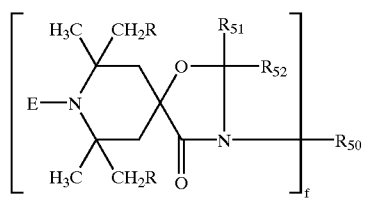
(U) 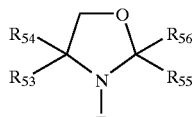
(V) 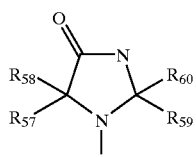
(W) 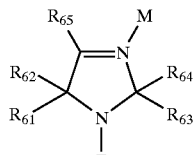
(X) 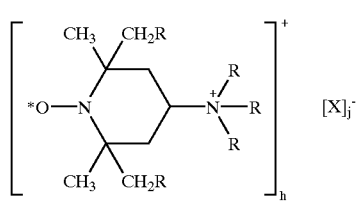
(Y) 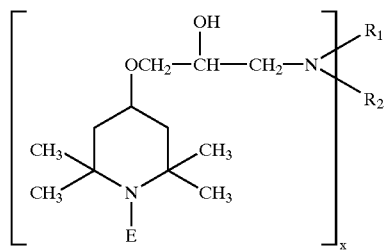

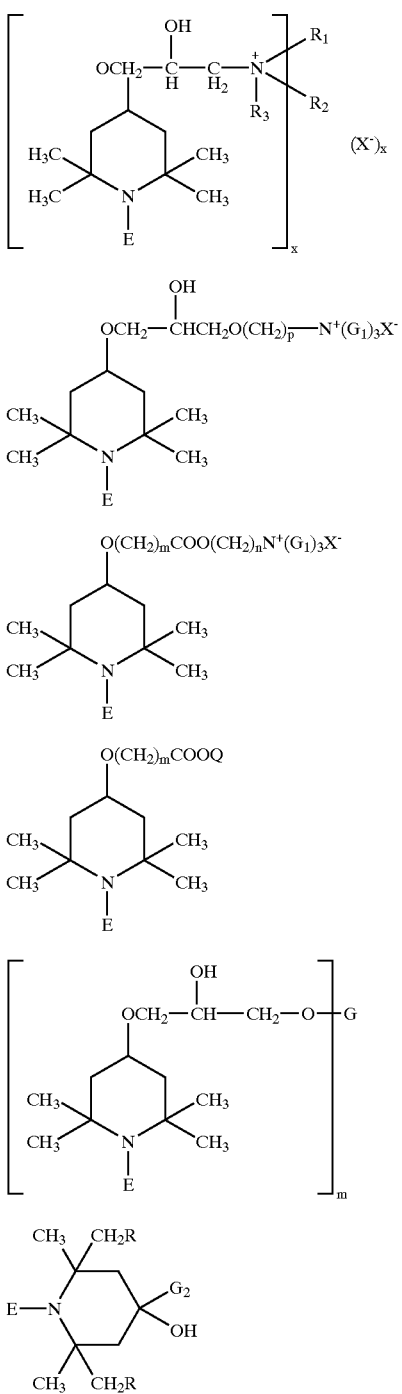

wherein
E is oxyl,
R is hydrogen or methyl, and
in formula A,
n is 1 or 2,
when n is 1,
$R_1$ is hydrogen, alkyl of 1 to 18 carbon atoms, alkenyl of 2–18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1–3 and M is a metal ion from the 1st, 2nd or 3rd group of the periodic table or is Zn, Cu, Ni or Co, or M is a group $N_{n+}(R_2)_4$ where $R_2$ is alkyl of 1 to 8 carbon atoms or benzyl, and when n is 2,
$R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula B,
m is 1 to 4,
when m is 1,
$R_2$ is alkyl of 1 to 18 carbon atoms, alkyl of 3 to 18 carbon atoms interrupted by —COO—, or $R_2$ is —CH$_2$(OCH$_2$CH$_2$)$_n$OCH$_3$ where n is 1 to 12, or $R_2$ is cycloalkyl of 5 to 12 carbon atoms, aryl of 6 to 12 carbon atoms, or said aryl substituted by one to four alkyl groups of 1 to 4 carbon atoms, or $R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —N(R$_3$)$_2$ where $R_3$ is as defined above, when m is 2,
$R_2$ is alkylene of 1 to 12 carbon atoms, alkenylene of 4 to 12 carbon atoms, xylylene, alkylene of 2 to 12 carbon atoms interrupted by —COO—, or $R_2$ is —CH$_2$(OCH$_2$CH$_2$)$_n$OCH$_2$— where n is 1 to12, or $R_2$ is cycloalkylene of 5 to 12 carbon atoms, aralkylene of 7 to 15 carbon atoms or arylene of 6 to 12 carbon atoms, or $R_2$ is —NHR$_4$NH— where $R_4$ is alkylene of 2 to 18 carbon atoms, cycloalkylene of 5 to 12 carbon atoms, aralkylene of 8 to 15 carbon atoms or arylene of 6 to 12 carbon atoms, or $R_2$ is —N(R$_3$)R$_4$N(R$_3$)— where $R_3$ and $R_4$ are as defined above, or $R_2$ is —CO— or —NH—CO—NH—, when m is 3,
$R_2$ is alkanetriyl of 3 to 8 carbon atoms or benzenetriyl, or when m is 4,
$R_2$ is alkanetetrayl of 5 to 8 carbon atoms or benzenetetrayl, in formula C,
$R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, x is 1 or 2,
when x is 1,
$R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or $R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO⁻)$_n$M$_{n+}$ where n is 1–3 and M is a metal ion from the 1st, 2nd or 3rd group of the periodic table or is Zn, Cu, Ni or Co, or M is a group N$^{n+}$(R$_2$)$_4$ where R$_2$ is hydrogen, alkyl of 1 to 8 carbon atoms or benzyl, or when x is 2, $R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula D, $R_{10}$ is as defined above, y is 1 to 4, and $R_{12}$ is defined as $R_2$ above, in formula E, k is 1 or 2, when k is 1, $R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or $R_{20}$ and $R_{21}$ together are alkylene of 2 to 8 carbon atoms or said alkylene substituted by hydroxyl, or are acyloxy-alkylene of 4 to 22 carbon atoms, or when k is 2, $R_{20}$ and $R_{21}$ are together (—CH$_2$)$_2$C(CH$_2$—)$_2$, in formula F, $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, and when g is 2, $R_{31}$ is defined as $R_1$ above when n is 2, in formula G, $Q_1$ is —NR$_{41}$— or —O—, $E_1$ is alkylene of 1 to 3 carbon atoms, or $E_1$ is —CH$_2$—CH(R$_{42}$)—O— where R$_{42}$ is hydrogen, methyl or phenyl, or $E_1$ is —(CH$_2$)$_3$—NH— or $E_1$ is a direct bond, $R_{40}$ is hydrogen or alkyl of 1 to 18 carbon atoms, and $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —CH$_2$—CH(R$_{42}$)—OH where R$_{42}$ is as defined above, in formula H, p is 1 or 2, $T_4$ is as defined for $R_{11}$ when x is 1 or 2, and M and Y are independently methylene or carbonyl, in formula I, this formula denotes a recurring structural unit of a polymer where $T_1$ is ethylene or 1,2-propylene or is the repeating structural unit derived from an alpha-olefin copolymer with an alkyl acrylate or methacrylate, where q is 2 to 100, and $Q_1$ is —N(R$_{41}$)— or —O— where R$_{41}$ is as defined above, in formula J, r is 1 or 2, and $T_7$ is as defined for $R_1$ when n is 1 or 2 in formula A, in formula L, u is 1 or 2, and $T_{13}$ is as defined for $R_1$ when n is 1 or 2 in formula A, with the proviso that $T_{13}$ is not hydrogen when u is 1, in formula M, $E_1$ and $E_2$, being different, each are —CO— or —N(E$_5$)— where $E_5$ is hydrogen, alkyl of 1 to 12 carbon atoms or alkoxycarbonylalkyl of 4 to 22 carbon atoms, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, in formula N, $R_1$ is as defined for $R_1$ in formula A when n is 1, and $G_3$ is a direct bond, alkylene of 1 to 12 carbon atoms, phenylene or —NH—G$_1$—NH— where G$_1$ is alkylene of 1 to 12 carbon atoms, in formula O, $R_{10}$ is as defined for $R_{10}$ in formula C, in formula P, $E_6$ is an aliphtic or aromatic tetravalent radical, in formula T, $R_{51}$ is hydrogen, alkyl of 1 to 18 carbon atoms, cycloalkyl of 5 to 12 carbon atoms, or aryl of 6 to 10 carbon atoms, $R_{52}$ is hydrogen or alkyl of 1 to 18 carbon atoms, or $R_{51}$ and $R_{52}$ together of alkylene of 4 to 8 carbon atoms, f is 1 or 2, when f is 1, $R_{50}$ is as defined for $R_{11}$ in formula C when x is 1, or $R_{50}$ is —(CH$_2$)$_z$COOR$_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —N(R$_{55}$)$_4$ where R$_{55}$ is hydrogen, alkyl of 1 to 12 carbon atoms or benzyl, and when f is 2, $R_{50}$ is as defined for $R_{11}$ in formula C when x is 2, in formula U, $R_{53}$, $R_{54}$, $R_{55}$ and $R_{56}$ are independently alkyl of 1 to 4 carbon atoms or are together pentamethylene, in formula V, $R_{57}$, $R_{58}$, $R_{59}$ and $R_{60}$ are independently alkyl of 1 to 4 carbon atoms or are together pentamethylene, in formula W, $R_{61}$, $R_{62}$, $R_{63}$ and $R_{64}$ are independently alkyl of 1 to 4 carbon atoms or are together pentamethylene, $R_{65}$ is alkyl of 1 to 5 carbon atoms, and M is hydrogen or oxygen, in formulae X to CC n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethyl, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_kO[(CH_2)_kO]_h(CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, and Q is an alkali metal salt, ammonium or $N^+(G_1)_4$, in formula DD m is 2 or 3, when m is 2, G is —$(CH_2CHR—O)_rCH_2CHR$—, where r is 0 to 3, and R is hydrogen or methyl, and when m is 3, G is glyceryl, and in formula EE, $G_2$ is —CN, —$CONH_2$ or —$COOG_3$ where $G_3$ is hydrogen, alkyl of 1 to 18 carbon atoms or phenyl, X is an inorganic or organic anion, and where the total charge of cations h is equal to the total charge of anions j.

3. A composition according to claim 2 where in the compounds of component (b), X is phosphate, phosphonate, carbonate, bicarbonate, nitrate, chloride, bromide, bisulfide, sulfite, bisulfate, sulfate, borate, formate, acetate, benzoate, citrate, oxalate, tartrate, acrylate, gluconate, polyacrylate, fumarate, maleate, itaconate, glycolate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an aryisulfonate.

4. A composition according to claim 2 wherein the compound of component (b) is selected from the compounds of formulas A, B, C, D, Q, R, S, X, Y and Z where E is oxyl, R is hydrogen, and in formula A, n is 1 or 2, when n is 1, $R_1$ is hydrogen, alkyl of 1 to 6 carbon atoms, alkenyl of 2–6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or $R_1$ is alkyl of 1 to 4 carbon atoms substituted by a carboxy group or by —COOZ where Z is hydrogen or alkyl of 1 to 4 carbon atoms, and when n is 2, $R_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups, in formula B, m is 1 or 2 when m is 1, $R_2$ is alkyl of 1 to 4 carbon atoms or $R_2$ is $CH_2(OCH_2CH_2)_nOCH_3$ where n is 1 to 12, or $R_2$ is phenyl, or said phenyl substituted by one to three methyl groups, $R_2$ is —$NHR_3$ where $R_3$ is alkyl of 1 to 4 carbon atoms or phenyl, or said phenyl substituted by one or two methyl groups, when m is 2, $R_2$ is alkylene of 1 to 8 carbon atoms, alkenylene of 4 to 8 carbon atoms, or $R_2$ is —$CH_2(OCH_2CH_2)_nOCH_2$— where n is 1 to 12, $R_2$ is $NHR_4NH$ where $R_4$ is of 2 to 6 carbon atoms, aralkylene of 8 to 15 carbon atoms or arylene of 6 to 12 carbon atoms, and $R_2$ is —CO— or —NHCONH, in formula C, $R_{10}$ is hydrogen or, alkanoyl of 1 to 3 carbon atoms, x is 1 or 2, when x is 1, $R_{11}$ is hydrogen, alkyl of 1 to 6 carbon atoms or glycidyl, $R_{11}$ is alkyl of 1 to 4 carbon atoms substituted by a carboxy group or by COOZ where Z is hydrogen or alkyl of 1 to 4 carbon atoms, and when x is 2, $R_{11}$ is alkylene of 1 to 6 carbon atoms, in formula D, $R_{10}$ is hydrogen, y is 1 or 2, and $R_{12}$ is defined as $R_2$ above, and in formula Y and Z, x is 1 or 2, when x is 1, $R_1$ and $R_2$ are independently alkyl of 1 to 4 carbon atoms, or $R_1$ and $R_2$ are together tetramethylene, or pentamethylene, R₂ is hydrogen or alkyl of 1 to 4 carbon atoms, said alkyl group substituted by a hydroxyl group, when x is 2, R₁ is hydrogen, alkyl of 1 to 4 carbon atoms, said alkyl substituted by a hydroxyl group, R₂ is alkylene of 2 to 6 carbon atoms, and R₃ is as defined above.

5. A composition according to claim 2 wherein the compound of component (b) is selected from the compounds of formulas A, B, C, D, Q and R where E is oxyl, R is hydrogen, and in formula A, h is 1, R₁ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or R₁ is alkyl of 1 to 4 carbon atoms substituted by —COOZ where Z is hydrogen or alkyl of 1 to 4 carbon atoms, in formula B, m is 1 or 2, R₂ is alkyl of 1 to 4 carbon atoms or R₂ is CH₂(OCH₂CH₂)$_n$OCH₃ where n is 1 to 4, and when m is 2, R₂ is alkylene of 1 to 8 carbon atoms, in formula C, R₁₀ is hydrogen or alkanoyl of 1 or 2 carbon atoms, x is 1 or 2, when x is 1, R₁₁ is hydrogen, alkyl of 1 to 4 carbon atoms or glycidyl, R₁₁ is alkyl of 1 to 4 carbon atoms substituted by COOZ where Z is hydrogen or alkyl of 1 to 4 carbon atoms, and when x is 2, R₁₁ is alkylene of 1 to 6 carbon atoms, and in formula D, R₁₀ is hydrogen, y is 1 or 2, and R₁₂ is defined as R₂ above.

6. A composition according to claim 2 wherein the compound of component (b) is (a) bis(1-oxyl-2,2-6-6-tetramethylpiperidin-4-yl) sebacate;

(d) 1-oxyl-2,2,6,6-tetramethyl-4-acetamidopiperidine;

(g) 1-oxyl-2,2,6,6-tetramethyl-4-oxo-piperidine;

(j) 1-oxyl-2,2,6,6-tetramethyl-4-methoxy-piperidine;

(m) 1-oxyl-2,2,6,6-tetramethyl-4-acetoxypiperidine;

(o) 1-oxyl-2,2,6,6-tetramethyl-4-propoxy-piperidine;

(r) 1-oxyl-2,2,6,6-tetramethyl-4-(2-hydroxy-4-oxapentoxy)piperidine; or (t) 1-oxyl-2,2,6,6-tetramethyl-4-hydroxypiperidine.

7. A composition according to claim 6 wherein the compound of component (b) is (t) 1-oxyl-2,2,6,6-tetramethyl-4-hydroxypiperidine.

8. A process for preventing the loss of brightness and for enhancing resistance to yellowing of chemimechanical or thermomechanical paper which still contains lignin, which comprises treating said paper with an effective stabilizing amount of a compound of formula A to EE according to claim 2.

9. A composition according to claim 1 wherein the effective amount of the hindered amine compound of component (b) is 0.001 to 5% by weight based on the paper.

10. A composition according to claim 9 wherein the effective amount of the hindered amine compound of component (b) is 0.005 to 2% by weight based on the paper.

11. A composition according to claim 10 wherein the effective amount of the hindered amine compound of component (b) is 0.01 to 1% by weight based on the paper.

12. A composition according to claim 1 which additionally includes an effective amount of at least one coadditive selected from the group consisting of the UV absorbers, the polymeric inhibitors, the fluorescent whitening agents and metal chelating agents.

13. A composition according to claim 12 wherein the effective amount of the coadditive is 0.001 to 5% by weight based on the paper.

14. A composition according to claim 13 wherein the effective amount of the coadditive is 0.005 to 2% by weight based on the paper.

15. A composition according to claim 14 wherein the effective amount of the coadditive is 0.01 to 2% by weight based on the paper.

16. A composition according to claim 12 which additionally includes at least one coadditive selected from the group consisting of the metal chelating agents.

17. A composition according to claim 16 wherein the chelating agents are selected from the group consisting of ethylenediaminetetraacetic acid (EDTA), diethylenetriaminepentaacetic acid (DTPA), hydroxyethylethylenediaminetriacetic acid (HEDTA), nitrilotriacetic acid (NTA) and diethylenetriaminepentamethylenephosphonic acid (DTPMPA).

18. A composition according to claim 12 which additionally includes a mixture of a UV absorber and polymeric inhibitor.

19. A composition according to claim 12 which additionally includes a mixture of a UV absorber and a fluorescent whitening agent.

20. A composition according to claim 12 which additionally includes a mixture of a UV absorber and metal chelating agent.

21. A composition according to claim 12 which additionally includes a mixture of a polymeric inhibitor and a fluorescent whitening agent.

22. A composition according to claim 12 which additionally includes a mixture of a polymeric inhibitor and a metal chelating agent.

23. A composition according to claim 12 which additionally includes a mixture of a fluorescent whitening agent and a metal chelating agent.

24. A composition according to claim 12 which additionally includes a mixture of a UV absorber, a polymeric inhibitor and a metal chelating agent.

25. A composition according to claim 12 which additionally includes a mixture of a fluorescent whitening agent, a polymeric inhibitor and a metal chelating agent.

26. A composition according to claim 12 which additionally includes at least one coadditive selected from the group consisting of the UV absorbers.

27. A composition according to claim 26 wherein the UV absorbers are selected from group consisting of the benzotriazoles, the s-triazines, the benzophenones, the α-cyanoacrylates, the oxanilides, the benzoxazinones, the benzoates and the α-alkyl cinnamates.

28. A composition according to claim 27 wherein the UV absorbers are selected from the group consisting of the benzotriazoles, the s-triazines and the benzophenones.

29. A composition according to claim 12 which additionally includes at least one coadditive selected from the group consisting of the polymeric inhibitors.

30. A composition according to claim 29 wherein the polymeric inhibitors are selected from the group consisting of poly(ethylene glycol), poly(propylene glycol), poly(butylene glycol), poly(vinyl pyrrolidone and poly(ethylene/propylene glycol).

31. A composition according to claim 12 which additionally includes at least one coadditive selected from the group consisting of the fluorescent whitening agents.

32. A composition according to claim 31 wherein the flouorescent whitening agents are selected from the group consisting of the 4,4'-bis-(triazinylamino)-stilbene-2,2'-disulfonic acids, 4,4'-bis-(triazol-2-yl)stilbene-2,2'-disulfonic acids, 4,4'-dibenzofuranyl-biphenyls, 4,4'-(diphenyl)-stilbenes, 4,4'-distyryl-biphenyls, 4-phenyl-4'-benzoxazolyl-stilbenes, stilbenyl-naphthotriazoles, 4-styryl-stilbenes, bis-benzoxazol-2-yl) derivatives, bis-(benzimidazol-2-yl) derivatives, coumarins, pyrazolines, naphthalimides, triazinyl-pyrenes, 2-styryl-benzoxazole or -naphthoxazoles, benzimidazole-benzofurans and oxanilides.

33. A process for preventing the loss of brightness and for enhancing resistance to yellowing of chemimechanical or thermomechanical paper which still contains lignin, which comprises treating said paper with an effective stabilizing amount of a compound of formula I according to claim 1.

34. A composition according to claim 1 which additionally contains a carrier or additive typically used in paper making which is selected from the group consisting of retention aids, sizing aids, starches, precipitated or ground calcium carbonate, clays, fillers and brightening additives.

* * * * *